US012272980B2

United States Patent
Muller et al.

(10) Patent No.: US 12,272,980 B2
(45) Date of Patent: *Apr. 8, 2025

(54) NEUROMODULATION APPARATUS, METHOD AND SYSTEM

(71) Applicant: Nia Therapeutics, Inc., Radnor, PA (US)

(72) Inventors: Rikky Muller, San Francisco, CA (US); Benjamin Johnson, Boise, ID (US); Igor Izyumin, Oakland, CA (US)

(73) Assignee: Nia Therapeutics, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/380,166

(22) Filed: Oct. 14, 2023

(65) Prior Publication Data

US 2024/0039318 A1    Feb. 1, 2024

Related U.S. Application Data

(63) Continuation of application No. 17/696,182, filed on Mar. 16, 2022, now Pat. No. 11,791,645, which is a (Continued)

(51) Int. Cl.
*A61B 5/293* (2021.01)
*A61B 5/00* (2006.01)
(Continued)

(52) U.S. Cl.
CPC ............ *H02J 7/0063* (2013.01); *A61B 5/291* (2021.01); *A61B 5/293* (2021.01); *A61B 5/4836* (2013.01);
(Continued)

(58) Field of Classification Search
None
See application file for complete search history.

(56) References Cited

U.S. PATENT DOCUMENTS

| 6,016,449 A | 1/2000 | Fischell et al. |
| 6,647,296 B2 | 11/2003 | Fischell et al. |

(Continued)

FOREIGN PATENT DOCUMENTS

| WO | WO1997037720 A1 | 10/1997 |
| WO | WO2014089553 A1 | 6/2014 |
| WO | WO2015026988 A1 | 2/2015 |

OTHER PUBLICATIONS

Notification of Transmittal of the International Preliminary Report on Patentability from the International Preliminary Examining Authority for International Application No. PCT/US2017/042043, dated Sep. 19, 2018, pp. 1-16.
(Continued)

*Primary Examiner* — Ankit D Tejani
(74) *Attorney, Agent, or Firm* — Nancy R. Gamburd; Gamburd Law Group LLC

(57) ABSTRACT

Representative methods, apparatus and systems are disclosed for providing concurrent electrical stimulation and electrical recording in a human or non-human subject, such as for neuromodulation, with the apparatus coupleable to an electrode array. A representative apparatus is typically an integrated circuit including: stimulation circuits, recording circuits, and blocking circuits responsive to control signals to block the stimulation voltage or current on an electrode from a corresponding recording circuit, while other recording circuits may simultaneously record electrical signals from other electrodes and generate recorded data. A representative stimulation circuit may include current sources; a first multiplexer for current source selection; a second multiplexer for electrode selection; a switchable voltage offset circuit; a switchable grounding circuit; and a stimulation controller providing control signals to provide the electrical stimulation, such as biphasic or monophasic
(Continued)

stimulation, and bipolar or unipolar stimulation. Off-chip communication, control, along with power and voltage level control, are also provided.

19 Claims, 31 Drawing Sheets

Related U.S. Application Data continuation of application No. 16/317,538, filed as application No. PCT/US2017/042043 on Jul. 14, 2017, now Pat. No. 11,305,122.

(60) Provisional application No. 62/510,380, filed on May 24, 2017, provisional application No. 62/362,770, filed on Jul. 15, 2016.

(51) Int. Cl.

| | |
|---|---|
| *A61B 5/291* | (2021.01) |
| *A61N 1/36* | (2006.01) |
| *A61N 1/372* | (2006.01) |
| *H02J 1/08* | (2006.01) |
| *H02J 7/00* | (2006.01) |
| H02J 50/20 | (2016.01) |

(52) U.S. Cl.
CPC ........ *A61B 5/6868* (2013.01); *A61N 1/36125* (2013.01); *A61N 1/36139* (2013.01); *A61N 1/36157* (2013.01); *A61N 1/36167* (2013.01); *A61N 1/37223* (2013.01); *H02J 1/082* (2020.01); *H02J 7/00* (2013.01); A61B 5/4094 (2013.01); H02J 7/0025 (2020.01); H02J 50/20 (2016.02); H02J 2207/20 (2020.01)

(56) References Cited

U.S. PATENT DOCUMENTS

| | | | |
|---|---|---|---|
| 8,354,881 | B2 | 1/2013 | Denison |
| 11,791,645 | B2* | 10/2023 | Muller .................. A61B 5/6868 607/59 |
| 2006/0271128 | A1 | 11/2006 | Keuninckx |
| 2007/0179537 | A1 | 8/2007 | Rissman et al. |
| 2007/0249956 | A1 | 10/2007 | Carlson et al. |
| 2009/0079265 | A1 | 3/2009 | Seligman |
| 2009/0228069 | A1 | 9/2009 | Dai et al. |
| 2011/0054583 | A1 | 3/2011 | Litt et al. |
| 2012/0029377 | A1 | 2/2012 | Polak |
| 2016/0045747 | A1 | 2/2016 | Jiang et al. |

OTHER PUBLICATIONS

Notification of Transmittal of the International Search Report and Written Opinion of the International Searching Authority, or the Declaration for International Application No. PCT/US2017/042043, dated Nov. 27, 2017, pp. 1-18.
European Search Report, European Patent Application No. 17828508. 6, dated Oct. 2, 2019, pp. 1-11.
Communication pursuant to Article 94(3) EPC, European Patent Application No. 17828508.6, dated Nov. 3, 2020, pp. 1-3.
Avestruz, A.-T. et al. A 5 µ W/channel spectral analysis IC for chronic bidirectional brain-machine interfaces. IEEE J. Solid-State Circuits 43, pp. 3006-3024 (2008).
Bagheri, A. et al. Massively-parallel neuromonitoring and neurostimulation rodent headset with nanotextured flexible microelectrodes. IEEE Trans. Biomed. Circuits Syst. 7, pp. 601-609 (2013.
Brown, E. A. et al. Stimulus artifact elimination in a multi-electrode system. IEEE Trans. Biomed. Circuits Syst. 2, pp. 10-21 (2008).

Chen, W. M. et al. A fully integrated 8-channel closed-loop neural-prosthetic cmos soc for realtime epileptic seizure control. IEEE J. Solid-State Circuits 49, pp. 232-247 (2014).
Greenwald, E., Chen, C., Thakor, N., Maier, C. & Cauwenberghs, G. A CMOS neurostimulator with on-chip DAC calibration and charge balancing. in 2013 IEEE Biomedical Circuits and Systems Conference (BioCAS), pp. 89-92 (IEEE, 2013). doi:10.1109/BioCAS. 2013.6679646.
Heer, F. et al. Single-chip microelectronic system to interface with living cells. Biosens. Bioelectron. 22, pp. 2546-2553 (2007).
Liu, X. et al. The PennBMBI: a general purpose wireless brain-machine-brain interface system for unrestrained animals. In 2014 IEEE International Symposium on Circuits and Systems, pp. 650-653 (IEEE, 2014).
Lo, Y-K. et al. A 176-channel 0.5cm3 0.7g wireless implant for motor function recovery after spinal cord injury. IEEE Int. Solid-State Circuits Conference, 2016, pp. 382-384.
Mendrela, A. E. et al. A bidirectional neural interface circuit with active stimulation artifact cancellation and cross-channel common-mode noise suppression. IEEE J. Solid-State Circuits 51, pp. 955-965 (2016).
Moin, A. et al. Powering and communication for OMNI: a distributed and modular closed-loop neuromodulation device. In 38th Annual International Conference of the IEEE Engineering in Medicine and Biology Society, pp. 4471-4474 (IEEE, 2016).
Muller, R. et al. A Miniaturized 64-channel, 225uW Electrocorticographic Wireless Neural Sensor. Proc. of the IEEE Int. Solid-State Circuits Conference, 24.1, 2014, p. 3.
Muller, R. et al. A Minimally Invasive 64-channel Wireless uECoG Implant. IEEE Journal of Solid-State Circuits, 50(1), pp. 1-16 (2015).
Noorsal, E. et al. A Neural Stimulator Frontend With High-Voltage Compliance and Programmable Pulse Shape for Epiretinal Implants. IEEE J. Solid-State Circuits 47, pp. 244-256 (2012).
Pepin, E., Uehlin, J., Micheletti, D., Perlmutter, S. I. & Rudell, J. C. A high-voltage compliant, electrode-invariant neural stimulator front-end in 65nm bulk-CMOS. in ESSCIRC Conference 2016: 42nd European Solid-State Circuits Conference, pp. 229-232 (IEEE, 2016). doi:10.1109/ESSCIRC.2016.7598284.
Rhew, H. G. et al. A fully self-contained logarithmic closed-loop deep brain stimulation SoC with wireless telemetry and wireless power management. IEEE J. Solid-State Circuits 49, pp. 2213-2227 (2014).
Rouse, A. G. et al. A chronic generalized bi-directional brain-machine interface. J. Neural Eng. 8, 36018, pp. 1-20 (2011).
Salam, M. T., Perez Velazquez, J. L. & Genov, R. Seizure suppression efficacy of closed-loop versus open-loop deep brain stimulation in a rodent model of epilepsy. IEEE. Trans. Neural Syst. Rehabil. Eng. 24, pp. 710-719 (2016).
Shulyzki, R. et al. 320-Channel active probe for high-resolution neuromonitoring and responsive neurostimulation IEEE Trans. Biomed. Circuits Syst. 9, pp. 34-49 (2015).
Sit, J.-J. & Sarpeshkar, R. A Low-Power Blocking-Capacitor-Free Charge-Balanced Electrode-Stimulator Chip With Less Than 6 nA DC Error for 1-mA Full-Scale Stimulation. IEEE Trans. Biomed. Circuits Syst. 1, pp. 172-183 (2007).
Stanslaski, S. et al. Design and validation of a fully implantable, chronic, closed-loop neuromodulation device with concurrent sensing and stimulation. IEEE. Trans. Neural Syst. Rehabil. Eng. 20, pp. 410-421 (2012).
Viswam, V. et al. 2048 Action Potential Recording Channels With 2.4 µVrms Noise and Stimulation Artifact Suppression. 2016 IEEE Biomed. Circuits Syst. Conf., pp. 136-139 (2016). doi:10.1109/ BioCAS.2016.7833750.
Zanos, S., Richardson, A. G., Shupe, L., Miles, F. P. & Fetz, E. E. The neurochip-2: an autonomous head-fixed computer for recording and stimulating in freely behaving monkeys. IEEE. Trans. Neural Syst. Rehabil. Eng. 19, pp. 427-435 (2011).
Olsson, III, Roy H. et al., "Band-Tunable and Multiplexed Integrated Circuits for Simultaneous Recording and Stimulation With Microelectrode Arrays", IEEE Transactions on Biomedical Engineering, vol. 52, No. 7, Jul. 2005, pp. 1303-1311.

(56) References Cited

OTHER PUBLICATIONS

Thorson, Rune et al., "Battery Powered Neuromuscular Stimulator Circuit for Use During a Simultaneous Recording of Myoelectrical Signals", Medical Engineering and Physics 31 (2009), pp. 1032-1037.

\* cited by examiner

BIPOLAR: USES TWO ELECTRODES
MONOPHASIC: CS ACTIVE FOR FIRST PULSE

BIPOLAR: USES TWO ELECTRODES
BIPHASIC: CS ACTIVE FOR BOTH PULSES

UNIPOLAR: USES THE COUNTER
MONOPHASIC: CS ACTIVE FOR FIRST PULSE

UNIPOLAR: USES THE COUNTER
BIPHASIC: CS ACTIVE FOR BOTH PULSES

AC-COUPLED DATA RECEIVER

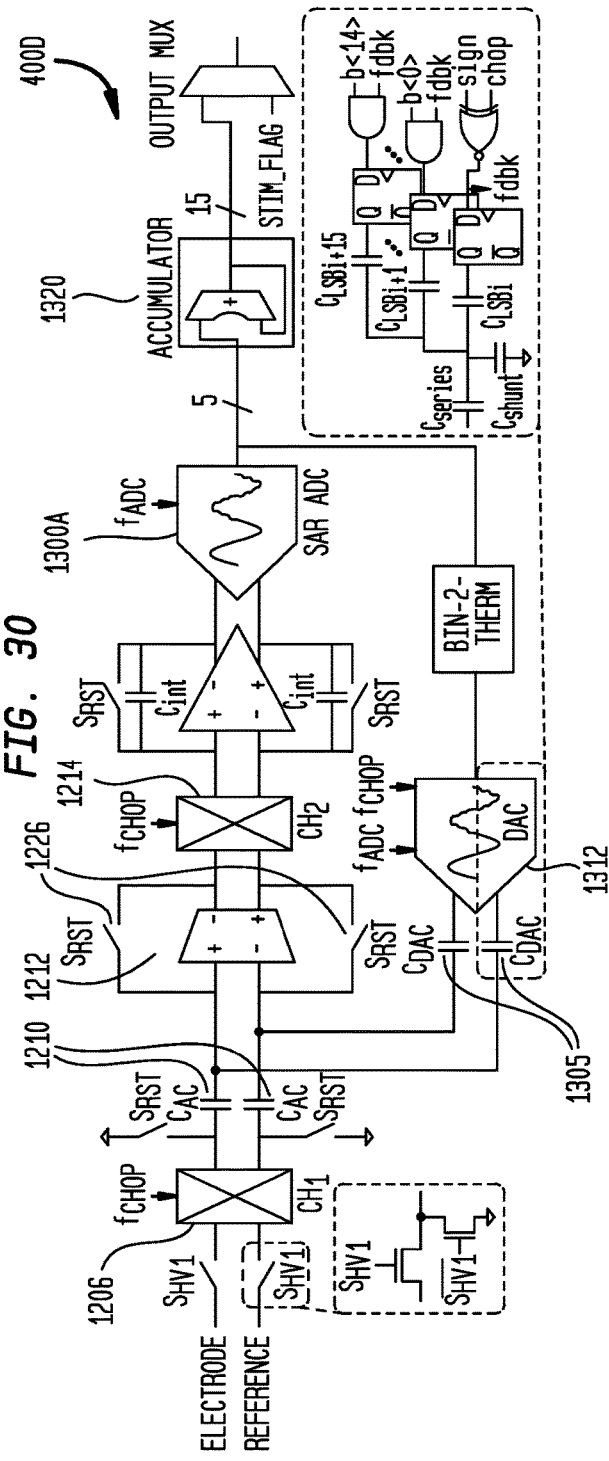
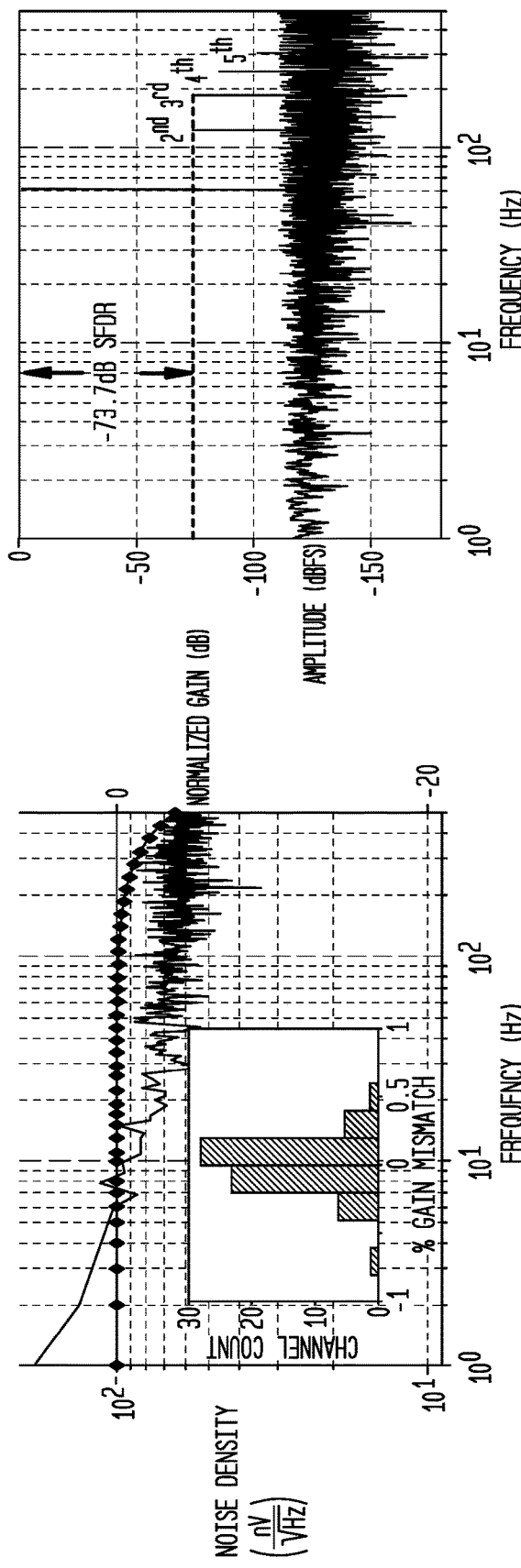
FIG. 30

STIMULATOR WAVEFORM RECONFIGURATION

FIG. 33

| | | [3] | [4] | [5] | THIS WORK |
|---|---|---|---|---|---|
| SYSTEM | Recording Channels | 4 | 256 | 16 | 64 |
| | Stim. Channels/No. of Stimulator | 2 + 8/ 2 + 8[a] | 64/64 | 160/40 | 64/4 |
| | Impedance Meas. Channels | 0 | 0 | 48 | 64 |
| | Data Rate Tx/Rx (Mbps) | 0.8/0.1 (RF) | 20/-- (Wireline) | 2/2 (RF) | 2/2 (Wireline) |
| | Power Supply | 915 MHz RF or 5V Battery | 3V_DC | 2 MHz RF | 3V_AC, 20MHz or 3V Battery |
| | Technology (nm) | 180 | 350 | 180 HV | 180 HV |
| | Die Size (mm²) | 4 | 12.8 | 25.1 | 11.52 |
| | Tot. Power Dissipation (mW) | 0.47 | 13.5 | -- | 0.7 |
| RECORDING | Power/Channel (µW) | 61.2 | 52 | 5.4 | 8 |
| | Supply Voltage (V) | 1.8 | 3.3 | ±1.8 | 1 |
| | Input-Referred Noise (nV/rtHz) | 81 | 82 | 92 | 71 |
| | NEF/PEF | 9.3./157 | 8.9/261 | 6.2/138 | 7.8/60.8[b] |
| | ADC Res./ENOB (bits) | 8/5.6 | 8/5.1 | --/8.5 | 15/10.2 |
| | Input Range (mVptp) | 1.2 | 1 | -- | 100/400[c] |
| | Dynamic Range (dB) | 35.5 | 32.9 | -- | 90 |
| | THD | 1.7% (1.2mVptp) | 0.8% (1mVptp) | -- | 0.7% (100mVptp) |
| STIMULATION | Max Current (mA) | 4.2/0.12 (6 bit) | 0.25 (--) | 0.5 (7 bit) | 5.04 (8 bit)[d] |
| | Supply Voltage (V) | 5 | 3.3 | ±6/±12 | 3/6/9/12 |
| | Frequency (Hz) | 15.4 | -- | Up to 20k | 15-255 (8 bit) |
| | Pulse Width (us) | 1000 | 150-230 | 10-800 | 15-500 (6 bit) |
| | Charge Cancellation | No | No | Yes | Yes |
| | Stimulation Recovery Time | Not simultaneous | N/A | Distant | 1ms |
| | Type | Biphasic | Mono&Biphasic | Biphasic only | Mono&Biphasic |

[a] 2 high-current stimulators and 8 low-current stimulators  [b] Includes ADC
[c] Input range expandable to 400mVptp  [d] All 4 stimulators can be combined for total Istim= 20.16mA

NEUROMODULATION APPARATUS, METHOD AND SYSTEM

CROSS-REFERENCE TO RELATED APPLICATIONS

This application is a continuation of and claims the benefit of and priority to U.S. patent application Ser. No. 17/696,182, filed Mar. 16, 2022, inventors Rikky Muller et al., titled "Neuromodulation Apparatus, Method and System", which is a continuation of and claims the benefit of and priority to U.S. patent application Ser. No. 16/317,538, filed Jan. 12, 2019 and issued Apr. 19, 2022 as U.S. Pat. No. 11,305,122 B2, inventors Rikky Muller et al., titled "Neuromodulation Apparatus, Method and System", which is a U.S. national phase under 35 U.S.C. Section 371 and claims the benefit of and priority to International Application No. PCT/US2017/042043 filed Jul. 14, 2017, titled "Neuromodulation Apparatus, Method and System", which is a nonprovisional of and claims the benefit of and priority to U.S. Provisional Patent Application No. 62/362,770, filed Jul. 15, 2016, inventors Rikky Muller et al., titled "Neuromodulation Apparatus, Method and System", and further is a nonprovisional of and claims the benefit of and priority to U.S. Provisional Patent Application No. 62/510,380, filed May 24, 2017, inventors Rikky Muller et al., titled "An Implantable 700 Microwatt 64-Channel Neuromodulation IC for Simultaneous Recording and Stimulation with Rapid Artifact Recovery", which are commonly assigned herewith, and all of which are hereby incorporated herein by reference in their entireties with the same full force and effect as if set forth in their entireties herein.

STATEMENT REGARDING FEDERALLY SPONSORED RESEARCH OR DEVELOPMENT

This invention was made with government support under grant No. W911NF-14-2-0043 awarded by the Department of Defense (DOD-DARPA). The government has certain rights in this invention.

FIELD OF THE INVENTION

The present invention, in general, relates to neuromodulation, and more particularly, relates to an apparatus, method and system for neuromodulation stimulation and neural recording.

BACKGROUND OF THE INVENTION

A variety of medical devices are utilized for chronic (e.g., long-term) delivery of electrical stimulation to patients suffering from conditions such as chronic pain, depression, tremors, Parkinson's disease, epilepsy, and neuroscientific research, for example and without limitation. Electrical stimulation generators are used for chronic delivery of electrical stimulation therapies such as neurostimulation, spinal cord stimulation, muscle stimulation, or stimulation to selected organs, also for example.

These devices typically provide therapy continuously or periodically according to a treatment plan and program specified by a physician or other clinician. Such a treatment plan and program generally will specify various stimulation parameters and values for each such parameter, such as various electrical parameters of a stimulation waveform, typically comprised of one or more electrical pulses which are to be delivered at selected locations within the subject, such as pulse width, pulse frequency, voltage and/or current amplitudes, electrode polarity (anode or cathode), selected electrode and/or stimulation location.

There is an ongoing need, however, for a new apparatus, method and/or system which is capable of providing closed-looped feedback in a singular device or system. Such an apparatus, method and/or system should provide both electrical sensing to record various electrical patterns (such as cortical signals) in real time, and to provide concurrent or nearly concurrent stimulation to selected areas in response to these sensed signals. Such an apparatus, method and/or system should provide for comparatively rapid feedback, to provide increased control in real-time over stimulation and changes in stimulation based upon the recorded data of changing patient or subject conditions, such as real-time neural electrical stimulation immediately following data acquisition from real-time neural electrical recording.

SUMMARY OF THE INVENTION

Concurrent sensing and stimulation remains a great challenge in realizing true closed-loop operation since stimulation can saturate amplifiers and create large, long-lasting artifacts that corrupt the signal. Most prior art systems must stimulate and record at different times or in separate brain regions. To enable true closed-loop operation, the recording and stimulation subsystems of the present disclosure have been co-designed to minimize interference and rapidly recover from stimulation artifacts as high as about 100 mV.

As discussed in greater detail below, a blocking circuit is utilized to block the recording circuitry on a given electrode when there is stimulation occurring on that given electrode, for any of the electrodes providing stimulation. In a representative embodiment, recording (which may be continuous) can be occurring on any or all other electrodes which are not concurrently providing stimulation. One of the truly novel features of the representative apparatus, system and method is that these recording and stimulation circuits are very compatible, such that there is a minimal or negligible artifact on the recording side. In representative embodiments, also as discussed in greater detail below, this is accomplished by implementing the following: (1) comparatively good charge balance in the stimulator; (2) a common voltage reference between recording and stimulation; (3) a comparatively large linear input voltage range on the recording side; and (4) comparatively fast recovery of the recording circuits, either through reset or broadband input. This results in an artifact that only lasts as long as the stimulation pulse itself and the recording circuits can recover immediately thereafter.

As discussed in greater detail below, the representative apparatus, system and method not only provide electrical sensing to record various electrical patterns (such as cortical signals) in real time, but also provide concurrent or nearly concurrent stimulation to selected areas in response to these sensed signals and further based upon selected stimulation programs, along with the amount and type of stimulation, determined by medical and other clinical professionals, enabling closed-looped feedback in a singular device and/or system. The representative apparatus, system and method provide for comparatively rapid feedback, to provide increased control in real-time over stimulation and changes in stimulation based upon the recorded data of changing patient or subject conditions, such as real-time neural electrical stimulation immediately following data acquisition from real-time neural electrical recording. In addition, representative apparatus, system and method embodiments enable rapid configuration and reconfiguration of stimulation waveforms.

Additional features and advantages of the representative apparatus, system and method are also discussed in greater detail below. For example, the representative apparatus, system and method are compatible with multiple types of electrodes, a variable number of electrodes, and electrodes in multiple different locations, further enabling a plurality of different spatial patterns of stimulation, each of which may have a different amount, type and pattern of stimulation. For example and without limitation, the representative apparatus, system and method may detect and record a cortical electrical pattern indicative of a likelihood of seizure activity, transmit this information for data processing, receive corresponding commands and stimulation parameters, and in response, generate corresponding cortical stimulations which prevent an otherwise ensuing seizure in an individual.

The representative apparatus and system are also modular and distributed, providing communication through a central hub (or router) which enable stimulation and recording in multiple, different and distributed locations throughout the body of a subject individual, while enabling centralized control over such stimulation. The representative apparatus and system are also scalable, capable of adding (or removing) modules (such as neuromodulation integrated circuits ("NMICs")) within the same system. The representative apparatus, system and method embodiments further provide for digital communication between and among the various components, enabling a significant number of communication channels with error correction and various other monitoring and safety protocols.

The representative apparatus, system and method embodiments also enable significant flexibility in stimulation. For example, representative embodiments provide for a wide variety of available voltage levels, e.g., ranging from 1 V to 12 V, enabling selection of and combining or mixing of comparatively high-voltage (HV) and low-voltage (LV) devices for stimulation of selected electrodes using a plurality of current sources coupled to the selected voltage level. An adaptive voltage supply also enables power conservation and provides additional voltage headroom. An AC-coupled interface further enables implantable operation.

Other notable advantages include the generation of an offset voltage during a second phase of a biphasic stimulation, eliminating the need for comparatively large negative voltages from charge transfer, and further improving the matching between phases.

A representative apparatus embodiment for concurrent electrical stimulation and electrical recording in a human or non-human (i.e., any animal) subject is disclosed, with the apparatus coupleable to an electrode array comprising a plurality of electrodes. Such a representative apparatus embodiment may comprise: a plurality of stimulation circuits selectively coupleable to the plurality of electrodes, each stimulation circuit responsive to a control signal of a first plurality of control signals to provide a stimulation voltage or current on a selected electrode of the plurality of electrodes; a plurality of recording circuits, each recording circuit to generate corresponding recorded data; and a plurality of blocking circuits, each blocking circuit coupled to a corresponding recording circuit of the plurality of recording circuits and further coupleable to a corresponding electrode of the plurality of electrodes, each blocking circuit responsive to a corresponding control signal of a second plurality of control signals to block the stimulation voltage or current on the selected electrode from the corresponding recording circuit.

As mentioned above, for example, a blocking circuit is utilized to block the recording circuitry on a given electrode when there is stimulation occurring on that given electrode, for any of the electrodes providing stimulation. In a representative embodiment, recording may be occurring on any or all other electrodes which are not concurrently providing stimulation.

In a representative embodiment, each recording circuit may further comprise: a reset circuit responsive to a corresponding control signal of a third plurality of control signals to provide a ground potential to an input of the corresponding recording circuit.

For example, when a stimulation circuit is providing a stimulation voltage or current to one or more selected electrodes of a first plurality of electrodes, each recording circuit is coupled to a corresponding electrode of a second plurality of electrodes of the electrode array to generate the corresponding recorded data, wherein the second plurality of electrodes is different from the first plurality of electrodes.

In a representative embodiment, each recording circuit may further comprise: an amplifier; and an analog-to-digital converter having a digitally-controlled reset circuit, such as an incremental, Successive Approximation Register ("SAR" 1300A), or equivalent analog-to-digital converter (e.g., delta-sigma, such as a differential incremental delta-sigma analog-to-digital converter 1300). In a representative embodiment, each recording circuit may further comprise an accumulator coupled to the SAR or other analog-to-digital converter. For example, when a stimulation circuit is providing a stimulation voltage or current to one or more selected electrodes of a first plurality of electrodes, each SAR or other analog-to-digital converter of each recording circuit is coupled to simultaneously receive a first voltage level from a corresponding electrode of a second plurality of electrodes of the electrode array and to receive a second voltage level from a reference electrode of the electrode array, and convert the difference of the first and second voltage levels to digital, differential voltage data, wherein the second plurality of electrodes is different from the first plurality of electrodes.

In a representative embodiment, the accumulator is adapted to accumulate a plurality of samples of the differential digital voltage data, and to output the accumulated differential digital voltage data as the corresponding recorded data, the corresponding recorded data further having an indicator bit. Also in a representative embodiment, the indicator bit indicates whether the corresponding recorded data is from a stimulation event, or from a recording event, or from impedance measurement.

In a representative embodiment, each recording circuit may further comprise: a current source coupled to the corresponding electrode of the plurality of electrodes, the current source providing a current to the corresponding electrode to generate the first voltage level for an impedance measurement In a representative embodiment, each stimulation circuit may comprise: a variable current source to generate a selectable, variable current to provide the stimulation voltage or current on the selected electrode. In a representative embodiment, each stimulation circuit may further comprise: a first multiplexer coupled to each variable current source, the first multiplexer comprising a first plurality of switches; and a second multiplexer coupled to the first multiplexer, the second multiplexer comprising a second plurality of switches, each switch of the second multiplexer coupleable to a corresponding electrode of the plurality of electrodes.

Also in a representative embodiment, each stimulation circuit may further comprise: a switchable voltage offset circuit coupleable to the corresponding electrode of the plurality of electrodes; and a switchable grounding circuit coupleable to the corresponding electrode of the plurality of electrodes.

In a representative embodiment, each stimulation circuit may further comprise: a stimulation controller to generate the first and second pluralities of control signals to implement at least one type of stimulation selected from the group consisting of: bipolar and biphasic, bipolar and monophasic, unipolar and biphasic, unipolar and monophasic, and combinations thereof. In a representative embodiment, each stimulation circuit may further comprise: an H bridge circuit adapted to control the direction of current flow between a plurality of electrodes to facilitate at least one type of stimulation using a single current source or plurality of current sources.

A representative apparatus embodiment may further comprise: a transceiver circuit; and a serial interface circuit, the serial interface circuit and a transmitter circuit of the transceiver circuit adapted to transmit the corresponding recorded data, the serial interface circuit and a receiver circuit of the transceiver circuit adapted to receive a plurality of commands and a plurality of stimulation patterns.

A representative apparatus embodiment may further comprise: a memory circuit storing a plurality of stimulation parameters, wherein the plurality of stimulation parameters comprise one or more parameters selected from the group consisting of: a pulse amplitude, a pulse duration, a pulse sequence, one or more selected electrodes, a stimulation pattern, and combinations thereof. In a representative embodiment, the stimulation controller may be adapted to determine a validity of the plurality of stimulation parameters.

A representative apparatus embodiment may further comprise: a plurality of programmable power converters to generate a corresponding plurality of voltage levels. A representative apparatus embodiment may further comprise: a system controller coupled to the plurality of programmable power converters, the system controller adapted to generate a third plurality of control signals to select one or more voltage level of the plurality of voltage levels and provide the selected one or more voltage levels to stimulation circuit and to the recording circuit.

A representative apparatus embodiment may further comprise: one or more circuits adapted to detect at least one fault or error condition, the at least one fault or error condition selected from the group consisting of: a loss of a clock signal, an insufficient stimulation current level, a data error, a parameter error, a compliance error, and combinations thereof.

A representative apparatus embodiment may further comprise: an alternating current (AC) to direct current (DC) power converter coupleable to receive an AC differential power input and convert the AC differential power input to a direct voltage or direct current. A representative apparatus embodiment also may further comprise: a clock recovery circuit coupled to receive the AC differential power input and convert the AC differential power input to a clock signal.

The representative apparatus may be embodied as an integrated circuit having a hermetically sealed package, the integrated circuit coupled to one or more separate capacitors external to the integrated circuit and located within the package.

A representative system for concurrent electrical stimulation and electrical recording in an animal subject is also disclosed. A representative system embodiment may comprise: one or more implantable electrode arrays; a first system controller and power supply to provide a plurality of stimulation parameters and a plurality of commands in response to received recorded data; and one or more implantable apparatuses coupled to the first system controller and power supply, each implantable apparatus coupled to a corresponding implantable electrode array comprising a plurality of electrodes, each implantable apparatus comprising: a plurality of stimulation circuits selectively coupleable to the plurality of electrodes, each stimulation circuit responsive to a control signal of a first plurality of control signals to provide a stimulation voltage or current on a selected electrode of the plurality of electrodes; a plurality of recording circuits, each recording circuit to generate corresponding recorded data; a transceiver circuit coupled to the plurality of stimulation circuits and to the plurality of recording circuits, the transceiver circuit adapted to transmit the corresponding recorded data to the first system controller and power supply and to receive the plurality of stimulation parameters and the plurality of commands from the first system controller and power supply for closed-loop feedback; and a plurality of blocking circuits, each blocking circuit coupled to a corresponding recording circuit of the plurality of recording circuits and further coupleable to a corresponding electrode of the plurality of electrodes, each blocking circuit responsive to a corresponding control signal of a second plurality of control signals to block the stimulation voltage or current on the selected electrode from the corresponding recording circuit.

Another representative apparatus embodiment for concurrent electrical stimulation and electrical recording in a human or non-human (i.e., any animal) subject is disclosed, with the apparatus coupleable to an electrode array comprising a plurality of electrodes. In a representative embodiment, the apparatus may comprise: a plurality of current sources; a first multiplexer coupled to the plurality of current sources, the first multiplexer comprising a first plurality of switches; a second multiplexer coupled to the first multiplexer, the second multiplexer comprising a second plurality of switches, each switch of the second multiplexer coupleable to a corresponding electrode of the plurality of electrodes; a switchable voltage offset circuit coupleable to the corresponding electrode of the plurality of electrodes; a switchable grounding circuit coupleable to the corresponding electrode of the plurality of electrodes; and a stimulation controller coupled to the plurality of current sources, the first multiplexer, the second multiplexer, the switchable voltage offset circuit, and the switchable grounding circuit, the stimulation controller adapted to generate a first plurality of control signals to provide the electrical stimulation to one or more selected electrodes of a first plurality of electrodes of the electrode array.

A representative apparatus embodiment may further comprise: a recorder circuit coupleable to the plurality of electrodes. For example, during electrical stimulation to the one or more selected electrodes of a first plurality of electrodes, the recorder circuit is adapted to record a plurality of electrical signals from a second plurality of electrodes of the electrode array and generate recorded data, the second plurality of electrodes different from the first plurality of electrodes.

Such a representative apparatus embodiment may further comprise: a switchable blocking circuit coupled to the recorder circuit and further coupleable to the plurality of electrodes; wherein the stimulation controller is further adapted to generate one or more control signals to the switchable blocking circuit, of the first plurality of control signals, to couple the recording circuit to the second plurality of electrodes or to uncouple the recording circuit from the first plurality of electrodes.

Such a representative apparatus embodiment may further comprise: a first programmable power converter coupled to the plurality of current sources, the first programmable power converter comprising a voltage ladder providing a first plurality of voltage levels for a corresponding plurality of voltage rails, the plurality of voltage levels having a range of 3V to 12V, for example. In a representative embodiment, the first programmable power converter may further comprise: a first plurality of capacitors; a third plurality of switches coupled to the first plurality of capacitors; and a switched discharge control circuit.

Such a representative apparatus embodiment may further comprise: a system controller coupled to the first programmable power converter, the system controller adapted to generate a second plurality of control signals to select a voltage level of the plurality of voltage levels and provide the selected voltage level to one or more current sources of the plurality of current sources.

Such a representative apparatus embodiment may further comprise: a second programmable power converter providing a second plurality of voltage levels from a 3V voltage rail, the second plurality of voltage levels having a range of 1V to 2V, for example. In a representative embodiment, the second programmable power converter may further comprise: a second plurality of capacitors; and a fourth plurality of switches coupled to the second plurality of capacitors.

In a representative embodiment, the stimulation controller may be adapted to generate the plurality of control signals to implement at least one type of stimulation selected from the group consisting of: bipolar and biphasic, bipolar and monophasic, unipolar and biphasic, unipolar and monophasic, and combinations thereof.

A representative apparatus embodiment may further comprise: a plurality of digital-to-analog converters, each digital-to-analog converter coupled to a corresponding current source of the plurality of current sources, and further coupled to the stimulation controller; wherein the stimulation controller is adapted to generate a first control signal to the first multiplexer, of the first plurality of control signals, to select a current source of the plurality of current sources for stimulation, and further to generate a second control signal to each digital-to-analog converter, of the first plurality of control signals, to control a current level of the selected current source of the plurality of current sources.

For example, in a representative embodiment, the stimulation controller may be adapted to generate a third control signal to the second multiplexer, of the first plurality of control signals, to select a first electrode for a first stimulation phase, of the plurality of electrodes. Also for example, in a representative embodiment, the stimulation controller may be adapted to generate a fourth control signal to a corresponding switchable grounding circuit, of the first plurality of control signals, to select a second electrode, of the plurality of electrodes, for a ground or current return path during the first stimulation phase of the first electrode. Also for example, in a representative embodiment, the stimulation controller may be adapted to generate a fifth control signal to a corresponding switchable voltage offset circuit coupleable to the first electrode, of the first plurality of control signals, to provide a voltage offset to the first electrode during a second stimulation phase. Also for example, in a representative embodiment, the stimulation controller may be adapted to generate a sixth control signal to the second multiplexer, of the first plurality of control signals, to select the second electrode for the second stimulation phase. Also for example, in a representative embodiment, the stimulation controller may be adapted to generate a plurality of seventh control signal to one or more corresponding switchable grounding circuits coupleable to a third plurality of electrodes, to concurrently select the third plurality of electrodes for ground or current return paths following the second stimulation phase.

In a representative embodiment, the stimulation controller may comprise: at least one configuration validity logic circuit; at least one cycle count logic circuit; a plurality of finite state machines coupled to a plurality of combinational logic gates; at least one voltage level shifter circuit; and at least one decoder circuit.

In a representative embodiment, the first multiplexer comprises a plurality of comparatively low voltage transistors, and wherein the second multiplexer comprises a plurality of comparatively high voltage transistors.

A representative method embodiment for concurrent electrical stimulation and electrical recording in a human subject using an electrode array comprising a plurality of electrodes is also disclosed. A representative method embodiment may comprise: selecting a stimulation pattern having a plurality of stimulation parameters; selecting a current source of a plurality of current sources; selecting one or more electrodes of a first plurality of electrodes of the electrode array; providing the electrical stimulation to one or more selected electrodes of the first plurality of electrodes; and recording a plurality of electrical signals from a second plurality of electrodes of the electrode array and generating recorded data, the second plurality of electrodes different from the first plurality of electrodes.

A representative method embodiment may further comprise: selecting a voltage or current level for each electrode of the stimulation pattern.

A representative method embodiment may further comprise: selecting one or more pulse durations for each electrode of the stimulation pattern.

A representative method embodiment may further comprise: generating a control signal to a switchable grounding circuit, of the first plurality of control signals, to provide a ground or return current path to a second electrode of the first plurality of electrodes.

A representative method embodiment may further comprise: blocking the electrical stimulation from recording circuitry on the one or more selected electrodes of the first plurality of electrodes.

Also in a representative embodiment, the method may further comprise: transmitting the recorded data to a centralized system controller; and receiving a plurality of commands and a plurality of stimulation patterns or stimulation parameters from the centralized system controller to provide closed-loop control. A representative method embodiment may further comprise: checking a validity of the received stimulation parameters. A representative method embodiment may further comprise: storing a plurality of stimulation parameters in a memory circuit.

A representative method embodiment may further comprise: providing a plurality of voltage levels. A representative apparatus embodiment may further comprise: generating one or more control signals to select a voltage level of the plurality of voltage levels and provide the selected voltage level to one or more current sources of a plurality of current sources.

A representative method embodiment may further comprise: detecting at least one fault or error condition, the at least one fault or error condition selected from the group consisting of: a loss of a clock signal, an insufficient stimulation current level, a data error, a parameter error, a compliance error, and combinations thereof. For example, a representative method embodiment may further comprise: in response to the detection of at least one fault or error condition, completing a current stimulation cycle and inhibiting further stimulation subsequent to the current stimulation cycle.

For example, a representative method embodiment may further comprise: selecting the first electrode for a first stimulation phase, of the first plurality of electrodes. Also for example, in a representative embodiment, the representative method embodiment may further comprise: selecting a second electrode, of the first plurality of electrodes, for a ground or current return path during the first stimulation phase of the first electrode. Also for example, in a representative embodiment, the representative method embodiment may further comprise: providing a voltage offset to the first electrode during a second stimulation phase. Also for example, in a representative embodiment, the representative method embodiment may further comprise: selecting the second electrode for the second stimulation phase. Also for example, in a representative embodiment, the representative method embodiment may further comprise: selecting a third plurality of electrodes for ground or current return paths following the second stimulation phase.

A representative method embodiment may further comprise: receiving an alternating current (AC) differential power input; and converting the radio-frequency differential power input to a direct voltage or direct current. A representative method embodiment may further comprise: converting the AC differential power input to a clock signal.

Another representative system embodiment for concurrent electrical stimulation and electrical recording in a human or non-human (i.e., any animal) subject is disclosed, with the representative system comprising: a first system controller and power supply to provide closed-loop feedback in response to received recorded data; and an implantable apparatus coupleable to the first system controller and power supply and to an implantable electrode array comprising a plurality of electrodes, the implantable apparatus comprising: a plurality of current sources; a first multiplexer coupled to the plurality of current sources, the first multiplexer comprising a first plurality of switches; a second multiplexer coupled to the first multiplexer, the second multiplexer comprising a second plurality of switches, each switch of the second multiplexer coupleable to a corresponding electrode of the plurality of electrodes; a switchable voltage offset circuit coupleable to the corresponding electrode of the plurality of electrodes; a switchable grounding circuit coupleable to the corresponding electrode of the plurality of electrodes; and a stimulation controller coupled to the plurality of current sources, the first multiplexer, the second multiplexer, the switchable voltage offset circuit, and the switchable grounding circuit, the stimulation controller adapted to generate a first plurality of control signals to provide the electrical stimulation to one or more selected electrodes of a first plurality of electrodes of the electrode array.

A representative apparatus embodiment may further comprise: a transceiver circuit; and a serial interface circuit, the serial interface circuit and a transmitter circuit of the transceiver circuit adapted to transmit the recorded data to the first system controller and power supply, the serial interface circuit and a receiver circuit of the transceiver circuit adapted to receive a plurality of commands and a plurality of stimulation patterns from the first system controller and power supply.

Another representative apparatus embodiment is disclosed for concurrent electrical stimulation and electrical recording in a human or non-human (i.e., any animal) subject, with the apparatus coupleable to an electrode array comprising a plurality of electrodes, the apparatus comprising: a plurality of stimulation circuits selectively coupleable to the plurality of electrodes, each stimulation circuit responsive to a control signal of a first plurality of control signals to provide a stimulation voltage on a selected electrode of the plurality of electrodes; a plurality of recording circuits, each recording circuit to generate corresponding recorded data; and a plurality of blocking circuits, each blocking circuit coupled to a corresponding recording circuit of the plurality of recording circuits and further coupleable to a corresponding electrode of the plurality of electrodes, each blocking circuit responsive to a corresponding control signal of a second plurality of control signals to block the stimulation voltage on the selected electrode from the corresponding recording circuit.

In a representative embodiment, one or more stimulation circuits have charge balance. In a representative embodiment, the plurality of recording circuits and the plurality of stimulation circuits have a common voltage reference. Also in a representative embodiment, the plurality of recording circuits have a comparatively large linear input voltage range and have comparatively fast recovery, either through a reset or a broadband input.

A representative embodiment of a recording circuit having a comparatively high linear input range is disclosed, comprising: a capacitive feedback loop having an ADC to reduce signal swing at internal nodes; a Gm stage having chopper-stabilization; and a current-input loop filter that suppresses noise at harmonics of the sample rate. In a representative embodiment, a 5-bit, 1024×-oversampled SAR ADC results in a 15-bit output and a charge-redistribution DAC provides feedback at the Gm input, creating a virtual ground. In a representative embodiment, the front-end gain is $C_{AC}/(C_{DAC}V_{fsDAC})$ and is independent of temperature and manufacturing variations.

The representative embodiment of a recording circuit may further comprise $S_{RST}$ Switches which are closed during a comparatively brief reset phase to store the offset of the Gm on $C_{AC}$, minimizing chopper ripple and aiding in comparatively rapid recovery by clearing a memory of the previous sample. In a representative embodiment, sampled $kT/C_{AC}$ noise is converted into out-of-band chopper ripple, enabling comparatively small values of $C_{AC}$ and comparatively high input impedance with $Z_{in}=1/(4C_{AC}f_{CHOP})$.

Numerous other advantages and features of the present invention will become readily apparent from the following detailed description of the invention and the embodiments thereof, from the claims and from the accompanying drawings.

BRIEF DESCRIPTION OF THE DRAWINGS

The objects, features and advantages of the present invention will be more readily appreciated upon reference to the following disclosure when considered in conjunction with the accompanying drawings, wherein like reference numerals are used to identify identical components in the various views, and wherein reference numerals with alphabetic characters are utilized to identify additional types, instantiations or variations of a selected component embodiment in the various views, in which:

FIG. 30 is a block diagram illustrating representative recording circuitry of a second representative neuromodulator integrated circuit apparatus embodiment and measurements, with the noise spectrum being input-referred and SFDR spectrum normalized to full scale input.

FIG. 33 is a table illustrating comparative results.

DETAILED DESCRIPTION OF REPRESENTATIVE EMBODIMENTS

Figure 1:
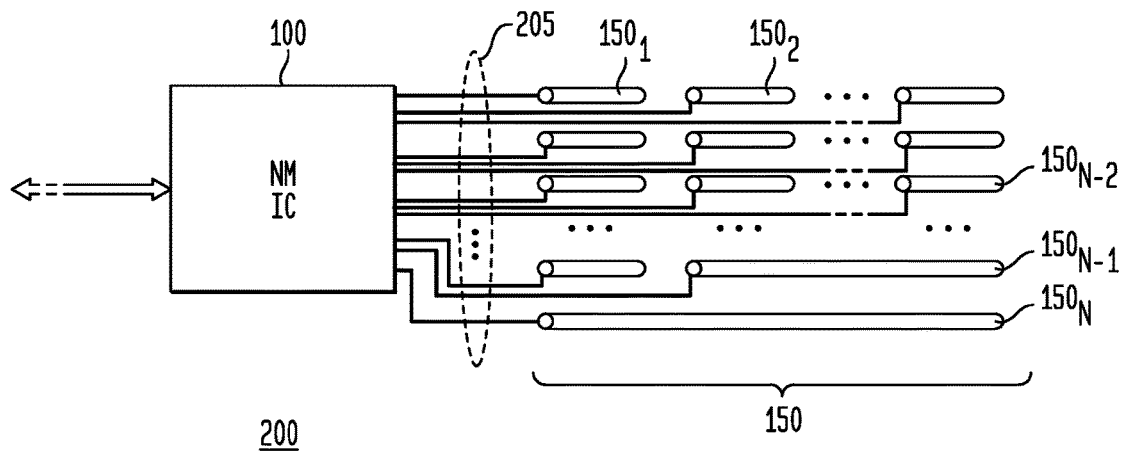
FIG. 1 is a block diagram illustrating a representative first system embodiment.

While the present invention is susceptible of embodiment in many different forms, there are shown in the drawings and will be described herein in detail specific exemplary embodiments thereof, with the understanding that the present disclosure is to be considered as an exemplification of the principles of the invention and is not intended to limit the invention to the specific embodiments illustrated. In this respect, before explaining at least one embodiment consistent with the present invention in detail, it is to be understood that the invention is not limited in its application to the details of construction and to the arrangements of components set forth above and below, illustrated in the drawings, or as described in the examples. Methods and apparatuses consistent with the present invention are capable of other embodiments and of being practiced and carried out in various ways. Also, it is to be understood that the phraseology and terminology employed herein, as well as the abstract included below, are for the purposes of description and should not be regarded as limiting.

FIG. 1 is a block diagram illustrating a representative first system 200 embodiment, which also may be referred to equivalently as a neuromodulator. As illustrated in FIG. 1, a first system 200 comprises a neuromodulation integrated circuit (NMIC) 100 apparatus coupled (via wires or bus 205) to a plurality of "N" electrodes, illustrated as electrodes $150_1$, $150_2$, through $150_{N-2}$, along with a generally larger reference electrode $150_{N-1}$ and another generally larger counter electrode $150_N$, collectively referred to as an electrode array 150 or otherwise as a plurality of electrodes 150. The electrodes 150 of the array may be any type of electrode, such as noninvasive electrodes which may be arranged or implanted on the surface of tissue (112), such as a cortical surface, or invasive, penetrating or otherwise needle-like electrodes arranged or implanted within a selected tissue (112). The electrodes 150 of the array may also have any selected size; for example, electrodes $150_1$, $150_2$, through $150_{N-2}$ may have a first size for recording and stimulation, the reference electrode $150_{N-1}$ may have a second size greater than the first size, and the counter electrode $150_N$ may have a third, larger size greater than both the first and second sizes. Significantly, both recording and stimulation may occur simultaneously or otherwise concurrently on any channel using different electrodes 150 of the array, under the control of the NMIC 100. For example, recording may occur using electrodes $150_1$, $150_2$, through $150_{10}$ and reference electrode $150_{N-1}$, while stimulation may occur simultaneously using electrodes $150_{11}$, $150_{12}$, through $150_{20}$ and counter electrode $150_N$, for example and without limitation.

Figure 2:
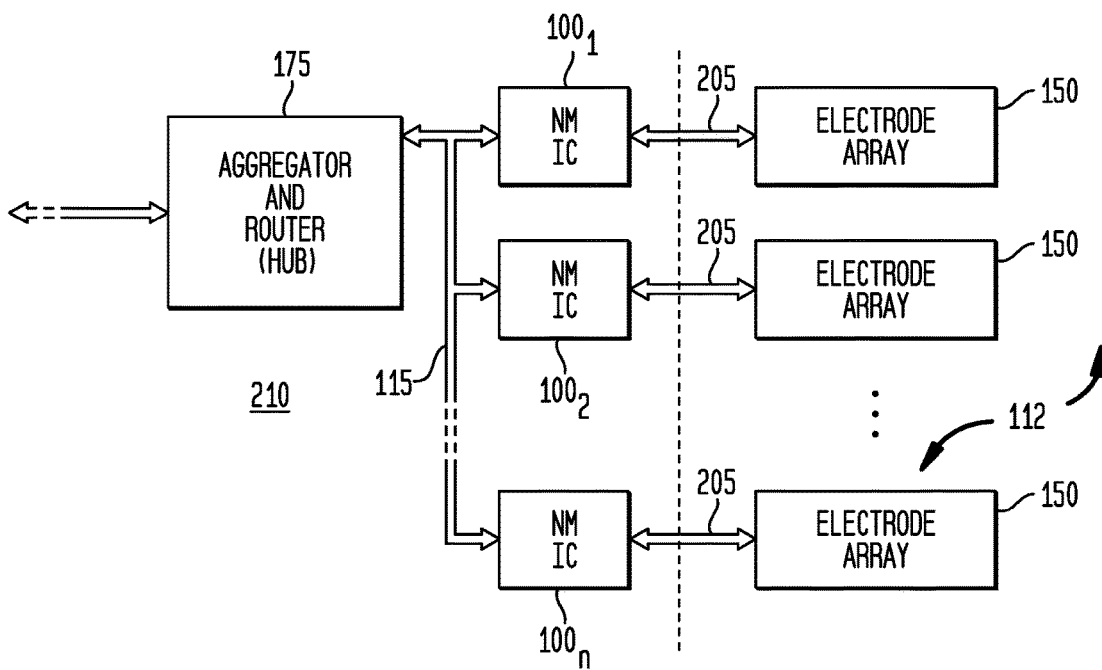
FIG. 2 is a block diagram illustrating a representative second system embodiment.

FIG. 2 is a block diagram illustrating a representative second system 210 embodiment. As illustrated in FIG. 2, a second system 210 comprises a plurality of neuromodulation integrated circuits (NMIC) 100 apparatus, illustrated as a plurality of "N" NMICs $100_1$, $100_2$, through $100_N$, correspondingly coupled to a plurality of electrode arrays 150, which are implanted in tissue 112, which may be any type of tissue (e.g., cortical, spinal, etc.). For this embodiment, each of the NMICs 100, with a corresponding electrode array 150, it generally implanted in a different area or region of the subject, such as in different locations in the subjects skull and/or brain, providing for distributed stimulation and recording. Each of the one or more NMICs 100 also may be coupled as an option to an aggregator and router (or "hub") 175, which also may be implemented as an integrated circuit. The aggregator and router (hub) 175 provides bidirectional communication to one or more NMICs 100, which may be full duplex or half duplex, and which may be wired or wireless, depending on the selected embodiment. In a representative embodiment, data communication to and from the one or more NMICs 100 is packet-based. For the second system 210, the NMIC 100 is coupled to the aggregator and router (hub) 175 through wires or bus 115. Any communication protocol may be utilized, over any number of wires, in any form, such as differential or single-ended. In a representative embodiment, five or six wires are used for each NMIC 100, with two or three wires providing digital communication (e.g., two wires for a downlink, one wire for an uplink), two wires providing differential and balanced AC power, and one ground wire.

Not separately illustrated in FIGS. 1 and 2, the NMIC 100 and/or aggregator and router (hub) 175 are also generally coupled, wirelessly or wired, to a system controller and power supply 180, discussed in greater detail below with reference to FIGS. 3-5.

Figure 3:
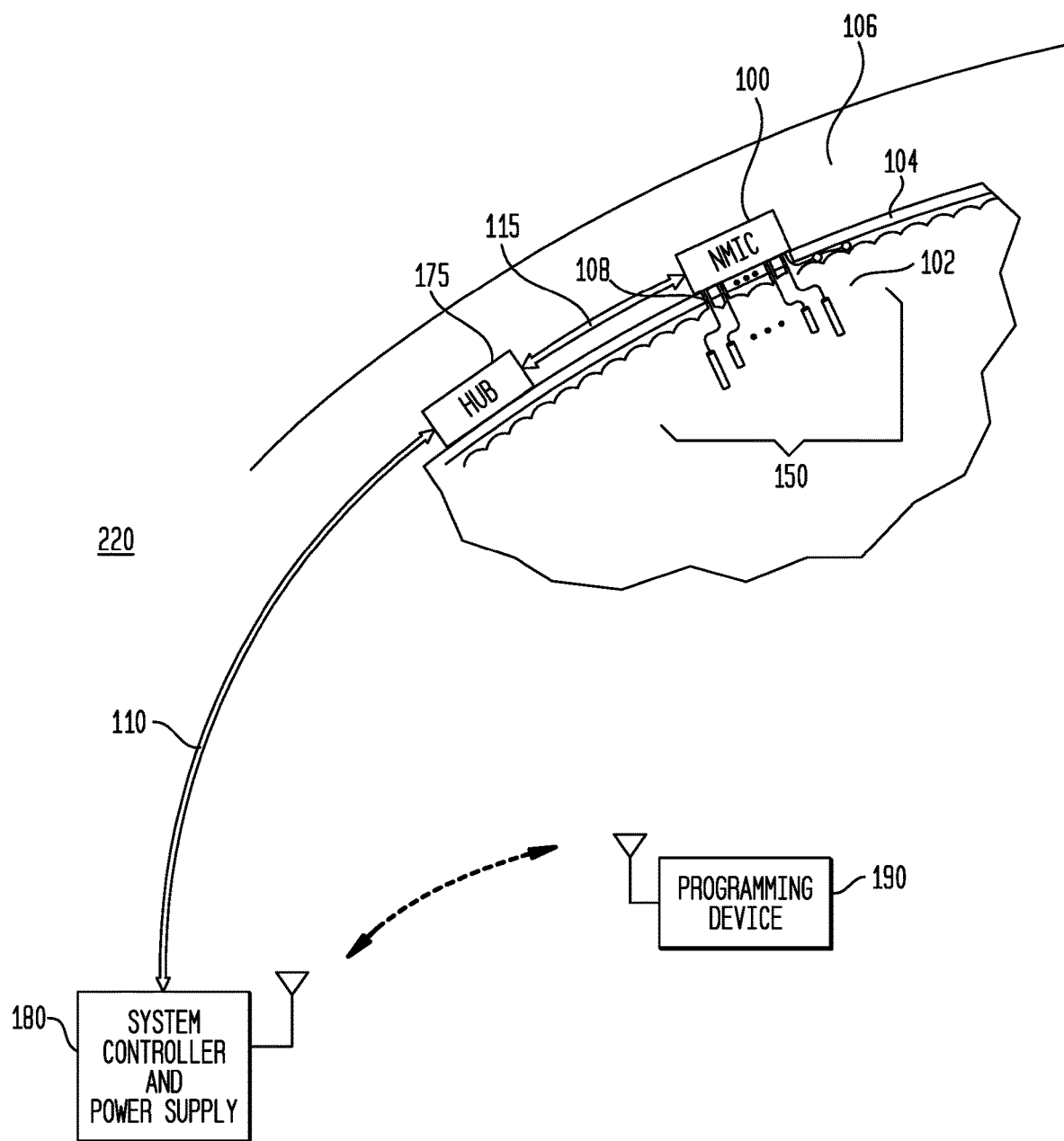
FIG. 3 is a block diagram illustrating a representative third system embodiment.

FIG. 3 is a block diagram illustrating a representative third system 220 embodiment. As illustrated in FIG. 3, a third system 220 comprises a neuromodulation integrated circuit (NMIC) 100 apparatus coupled to an electrode array 150, illustrated as a plurality of "N" electrodes $150_1$, $150_2$, through $150_N$, further coupled to an aggregator and router (hub) 175. Also as illustrated, the electrode array 150 is implanted underneath bone 104, such as a human or non-human (i.e., any animal) skull, and either or both on top of or into (animal) cortical tissue 102, such as a human or non-human (i.e., any animal) brain cortex or dura mater, or other locations as mentioned above and also discussed in greater detail below. The electrode array 150 is coupled, typically using wires or bus 205 through one or more holes 108, to the NMIC 100, which is arranged or disposed subcutaneously (underneath the skin 106) and adjacent and external to the bone 104. Alternatively, the one or more NMICs 100 may also be arranged underneath the skull or within a burr hole of the skull. The NMIC 100 is also coupled to the aggregator and router (hub) 175, which is also arranged or disposed subcutaneously (underneath the skin 106), adjacent and external to the bone 104 as illustrated, or at a more distal location. A system controller and power supply 180 is also coupled (typically via wires 110) to the aggregator and router (hub) 175, and is typically also located subcutaneously in another area of the body, such as the chest or neck area of a subject. As illustrated, the system controller and power supply 180 may communicate wirelessly to a programming device 190. Each of these components is discussed in greater detail below. Alternatively, when an aggregator and router (hub) 175 is not included, the system controller and power supply 180 may be coupled (wired or wirelessly) directly to one or more NMICs 100, as illustrated in FIG. 5.

Figure 4:
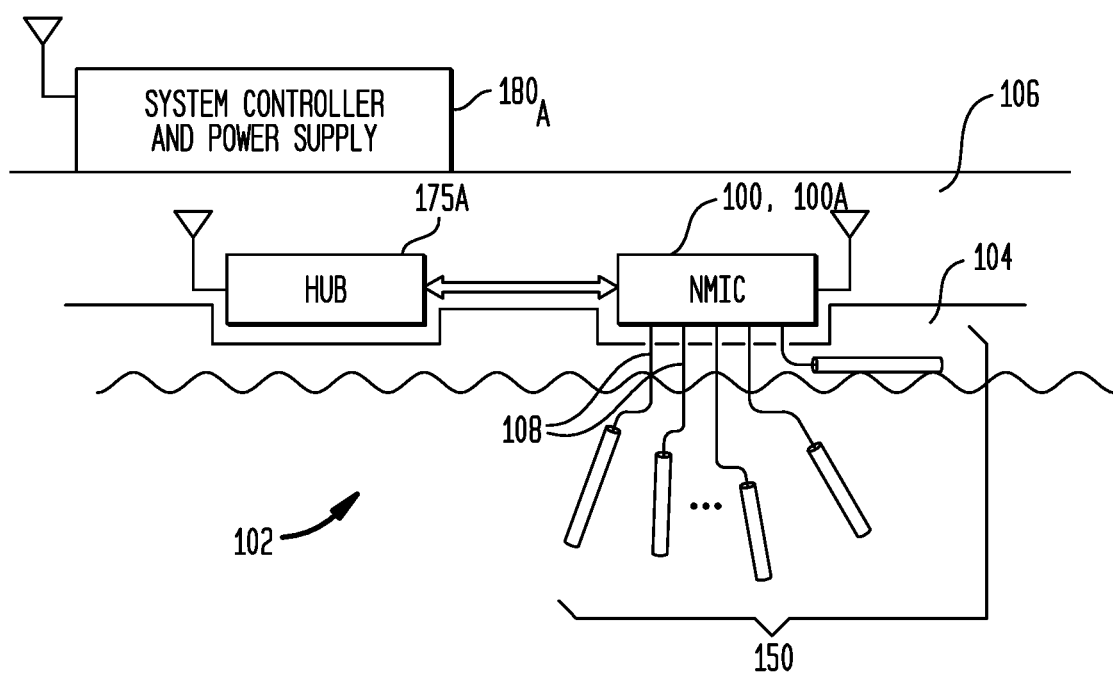
FIG. 4 is a block diagram illustrating a representative fourth system embodiment.

FIG. 4 is a block diagram illustrating a representative fourth system 230 embodiment. As illustrated in FIG. 4, a fourth system 230 also comprises a neuromodulation integrated circuit (NMIC) 100 apparatus coupled to an electrode array 150, illustrated as a plurality of "N" electrodes $150_1$, $150_2$, through $150_N$, further coupled to an aggregator and router (hub) 175. Also as illustrated, the electrode array 150 is implanted underneath bone 104, such as a human or non-human (i.e., any animal) skull, and either or both on top of or into (animal) cortical tissue 102, such as a human or non-human (i.e., any animal) brain cortex or dura mater, or other locations as discussed in greater detail below. The electrode array 150 is coupled, typically using wires or bus 205 through one or more holes 108, to the NMIC 100, which is arranged or disposed subcutaneously (underneath the skin 106) and adjacent and external to the bone 104. Alternatively, the one or more NMICs 100 may also be arranged underneath the skull or within a burr hole of the skull. The NMIC 100 is also coupled to the aggregator and router (hub) 175, which is also arranged or disposed subcutaneously (underneath the skin 106), adjacent and external to the bone 104 as illustrated, or at a more distal location. For the fourth system 230, the system controller and power supply $180_A$ is also coupled wirelessly to the aggregator and router (hub) 175, and is typically also located externally to the skin in a nearby area or another area of the body, such as externally to the subject's skull. Alternatively, when an aggregator and router (hub) 175 is not included, the system controller and power supply $180_A$ may be coupled (wired or wirelessly) directly to one or more NMICs 100, such as directly wired as illustrated in FIG. 5. Not separately illustrated in FIG. 4, the system controller and power supply $180_A$ also may communicate wirelessly to a programming device 190, which typically provides the selected stimulation program determined by medical and other clinical professionals.

Also not separately illustrated in FIGS. 3 and 4, the system controller and power supply 180 may also be combined with the aggregator and router (hub) 175.

Figure 5:
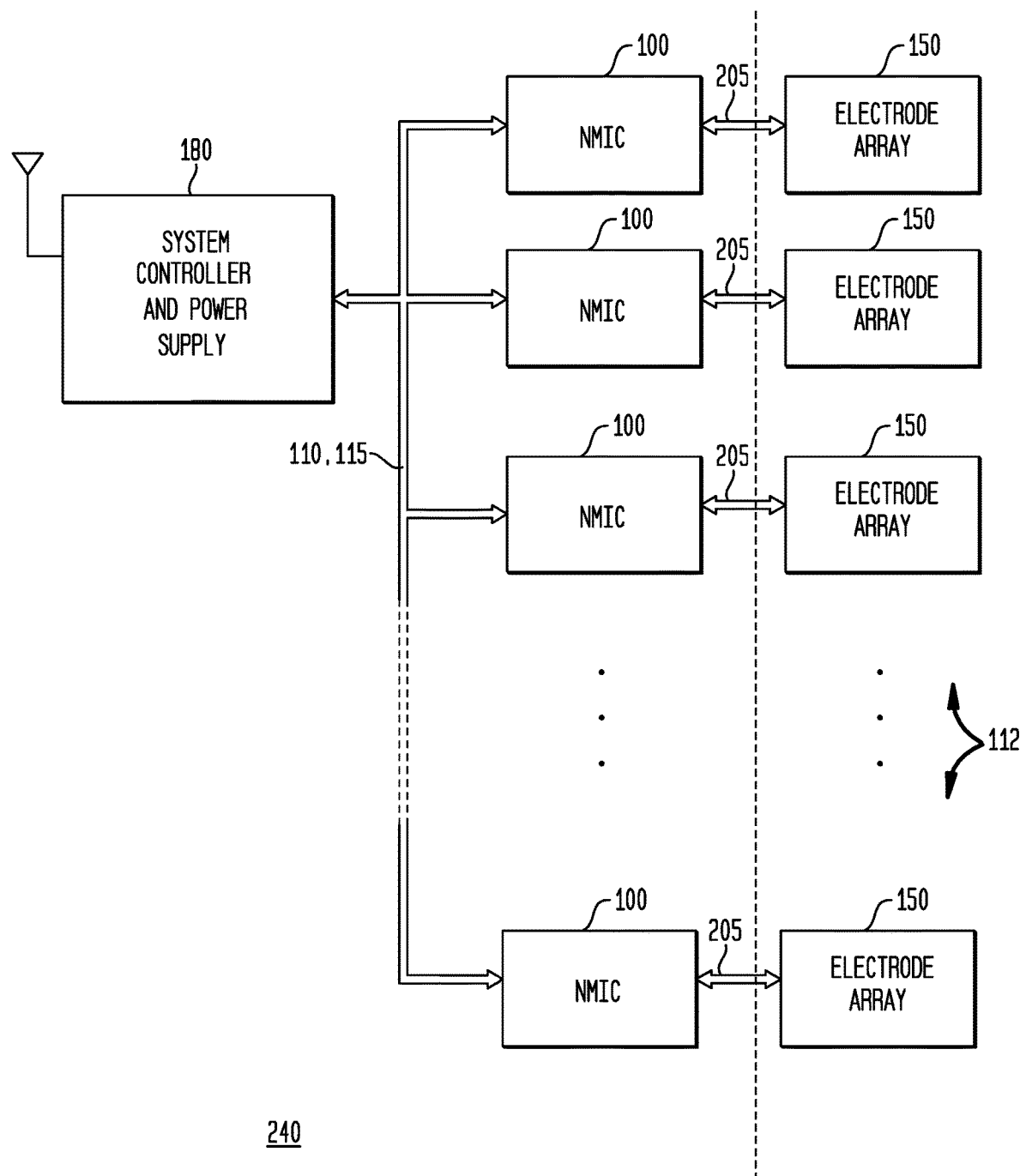
FIG. 5 is a block diagram illustrating a representative fifth system embodiment.

FIG. 5 is a block diagram illustrating a representative fifth system 240 embodiment. The representative fifth system 240 embodiment differs from the other systems 200, 210, 220 and 230 insofar as one or more NMICs 100 are coupled directly to the system controller and power supply 180, such as via hard-wired via wires or bus 110 or 115, as a network configuration. For this representative fifth system 240 embodiment, the one or more NMICs communicate directly with the system controller and power supply 180, for bidirectional communication to and from one or more NMICs 100, which may be full duplex or half duplex, and which may be wired or wireless, depending on the selected embodiment. In a representative embodiment, data communication to and from the one or more NMICs 100 is packet-based, such as using the differential AC signaling protocol and differential AC power transmission discussed in greater detail below, for example and without limitation. Any communication protocol may be utilized, over any number of wires, in any form, such as differential or single-ended. In a representative embodiment, five or six wires are also used for coupling each NMIC 100 to the system controller and power supply 180, with two or three wires providing digital communication (e.g., two wires for a downlink, one wire for an uplink), two wires providing differential and balanced AC power, and one ground wire.

This significantly low wire count is a notable advantage and improvement over prior art stimulator and/or recording circuitry, which have a much higher wire count. This reduced wire count, such as six wires per NMIC 100, also enables use of multiple NMICs 100 to have a network configuration distributed around a subject individual at different locations, while still retaining an overall low wire count to and from the system controller and power supply 180 and/or aggregator and router (hub) 175.

As illustrated in FIGS. 3-5, the NMIC 100 provides a "front end" to control both stimulation of and recording from the electrode array 150. The NMIC 100, in a representative embodiment, is arranged or disposed comparatively close to the electrode array 150, as an implant into the subject. The other components may be located more peripherally, and will provide digital communication to and from the NMIC 100.

For any of the various systems 200, 210, 220, 230 and 240, the electrode array 150 may be implanted in any suitable location, such as subcutaneously, on the surface of the dura, subdural, on the cortical surface, or subcortical, such as for brain locations, or other suitable locations, such as subcutaneous, epidural, subdural, or within the spinal cord of a subject, or other nervous system or organ locations. Other suitable locations may also be completely noninvasive and applied on the exterior of a subject's skin in any location, such as adjacent the spinal column for pain management, for example and without limitation.

The system controller and power supply 180 provides power to the aggregator and router (hub) 175 (which then provides power to the NMIC 100) and/or provides power directly to the NMIC 100. The system controller and power supply 180 generally includes a microprocessor (for data processing capability, and having corresponding software) and a memory circuit (e.g., FLASH memory) for data storage. The system controller and power supply 180 provides closed-loop control, receiving recording data from each NMIC 100 arranged within a subject (typically provided as data packets either directly as shown in FIG. 5 or via the aggregator and router (hub) 175 as shown in FIGS. 3 and 4), performing corresponding computations based on the recording data, and then generating commands or otherwise controlling the resulting stimulation provided to the subject. The system controller and power supply 180 also is configured to stream data out to the programming device 190 or another programming interface to the various systems.

The system controller and power supply 180 typically includes a power supply, such as a battery, and provides power to the aggregator and router (hub) 175 or directly to the one or more NMICs 100. Power is typically provided as AC power to the NMICs 100, to avoid DC currents, and the various systems 200, 210, 220, 230 and 240 are typically isolated from DC leakage currents. For example, in the representative embodiments, AC power is provided to the NMIC 100 (from either the aggregator and router (hub) 175 or directly from the system controller and power supply 180 as differential and balanced AC power, typically at one or more radiofrequencies ("RF"), using a pair of wires, which may also be utilized for timing (to derive a clock signal, as discussed in greater detail below). Alternatively, a timing signal may be separate, and generally at a different frequency. Also in the representative embodiments, a ground return is also typically provided, and all data communication links between the NMIC 100 (to and from either the aggregator and router (hub) 175 or the system controller and power supply 180) are capacitively coupled at each end, providing DC isolation on both sides.

When the aggregator and router (hub) 175 is implemented, in addition to communication circuitry, it typically includes an AC-to-DC (e.g., RF-to-DC) rectifier and a step down DC-DC power converter, such as those implemented and discussed below with reference to FIG. 6. In turn, the aggregator and router (hub) 175 provides power in parallel to the one or more NMICs 100.

For the data communication links between the NMIC 100, to and from either the aggregator and router (hub) 175 or the system controller and power supply 180, an uplink and a downlink are typically provided, which can be either differential or single-ended, and which may be separate wires or multiplexed. In a representative embodiment, bidirectional and differential signaling is utilized, to reduce the wire count and to reduce potential interference and other sources of noise. The communication links and protocols are discussed in greater detail below and additionally with reference to FIG. 23.

In a representative embodiment, the aggregator and router (hub) 175 may be implemented as a multiplexer, and modulates signals from the NMICs 100 transmitted to the system controller and power supply 180.

For any of the various systems 200, 210, 220, 230 and 240, one electrode array 150 and one NMIC 100 are typically provided together as a single unit within hermetically-sealed packaging, with multiple packages of each paired NMIC 100 and electrode array 150 utilized for embodiments having multiple NMICs 100 coupled to electrode arrays 150. Not separately illustrated in FIGS. 1-5, off-chip capacitors are typically provided for power storage for the NMIC 100, to provide as much as 5 mA current and up to 12 Volts (60 mW), and are typically included within this hermetically-sealed package. Also in representative embodiments, detachable wired links are provided between the one or more NMICs 100 and the aggregator and router (hub) 175 and/or the system controller and power supply 180.

For any of the various systems 200, 210, 220, 230 and 240, the system controller and power supply 180 may be combined into a singular unit. In addition, when only one NMIC 100 is utilized in a selected embodiment, the aggregator and router (hub) 175 may be omitted, with communication and power, for example, provided (wired or wirelessly) directly from the system controller and power supply 180.

Figure 6:
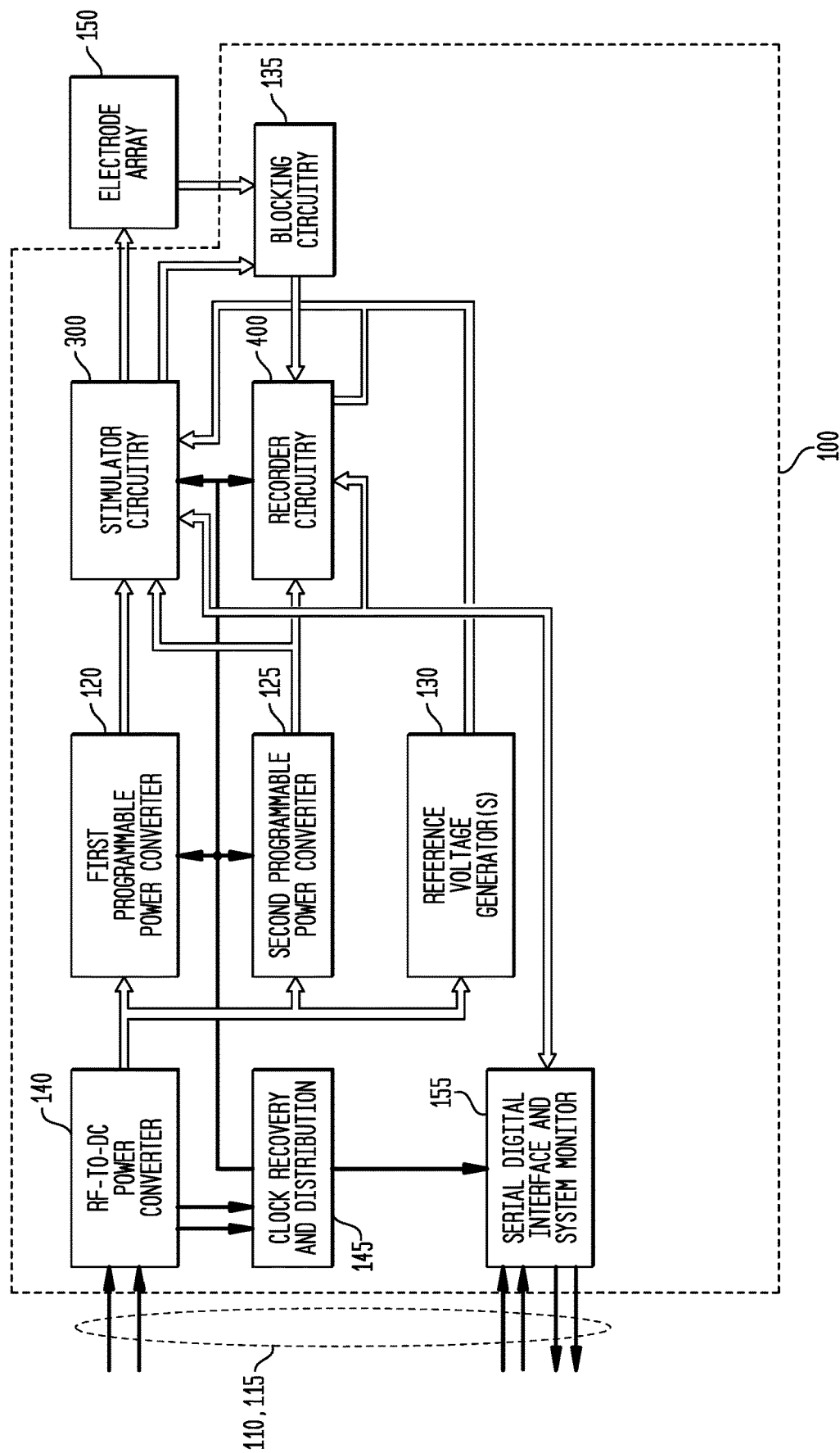
FIG. 6 is a block diagram illustrating a first representative neuromodulator integrated circuit apparatus embodiment.

FIG. 6 is a block diagram illustrating a first representative neuromodulator integrated circuit (NMIC) 100 apparatus embodiment. The representative NMIC 100 is illustrated as being coupled to an electrode array 150. As illustrated in FIG. 6, the representative NMIC 100 comprises stimulator circuitry (or stimulator) 300, recorder (or recording) circuitry 400, blocking circuitry 135 (which are illustrated separately, but may also be considered to be part of either the stimulator circuitry 300 or the recorder circuitry 400), an AC-to-DC (e.g., RF-to-DC) power converter 140, clock recovery and distribution circuitry 145, a serial digital interface and system monitor 155, a first programmable power converter 120, a second programmable power converter 125, and one or more reference voltage generator(s) 130. Each of these components is discussed in greater detail below.

As the representative NMIC 100 is described in greater detail below, numerous advantages will be readily apparent, including a stimulator 300 circuit architecture that enables use of both high and low voltage devices, with an adjustable power supply. For example and without limitation, and as discussed in greater detail below, the first programmable power converter 120 and the second programmable power converter 125 each provide variable voltage levels, for fine-grained control over stimulation, enabling use of both low and high voltage components in the same integrated circuit, with multiple voltage rails, sufficient headroom in the event of a decreased input voltage, and providing significant power savings, especially important in an implantable device having a limited power supply, such as a battery.

As discussed in greater detail below, the stimulator circuitry 300 of the representative NMIC 100 also re-uses the same current source (330) for both phases of stimulation in biphasic mode, to improve matching between the phases, across a plurality of channels. A highly inventive voltage offset is generated during the second phase, to eliminate negative voltages from charge transfer. In addition, the stimulation is centered around a ground potential, starting and returning to zero volts, without requiring any negative voltage supply or rail, making full use of the voltage headroom, and further being compatible with low-voltage recording circuitry 400.

In addition, the representative NMIC 100 provides an AC-coupled power and communication interface for safe operation of the NMIC 100 in vivo, with the clock recovery and distribution circuitry 145 deriving a clock signal from this AC power input, and with the AC-to-DC (e.g., RF-to-DC) power converter 140 generating DC power from this AC power input. For example and without limitation, this AC-coupling prevents any DC connection from the NMIC 100 to the tissue (112), such as if the insulation were to fail on any wiring (110, 115, 205), as any such DC connection could be harmful. The AC-coupled communication generates edge-triggered digital communication using the serial digital interface and system monitor 155 for robust operation and robust communication with the system controller and power supply 180, including error reporting.

The NMIC 100 also provides a tight coupling and significant integration between the stimulator circuitry 300 and the recorder circuitry 400, enabling simultaneous recording and stimulation, with a large dynamic range provided in recording to accommodate stimulation artifacts, along with integrated impedance measurements. In addition, the recorder circuitry 400 uses incremental, or delta-sigma ADC 1300 or SAR ADC 1300A or other ADC recording to support concurrent stimulation, with a resettable interface for rapid recovery from saturation and greater stability, and compatibility with receiving a blocking signal from the stimulator controller 320. The recorder circuitry 400 is DC-coupled to provide charge monitoring at the electrode 150 interface, with different gain modes to accommodate larger artifacts from stimulation events, and with a digital output also indicating a stimulation event or an impedance measurement during a sample.

Representative embodiments of the recorder circuitry 400 are discussed in greater detail below with reference to FIGS. 24-27. The recorder circuitry 400 also may be implemented as described in Patent Cooperation Treaty (PCT) Patent Application No. PCT/US2014/051959, filed Aug. 20, 2014 and published as WO 2015/026988, inventors Rikky Muller et. al. titled "Systems and Methods for Electrocorticography Signal Acquisition", and also in Patent Cooperation Treaty (PCT) Patent Application No. PCT/US2015/014905, filed Feb. 6, 2015 and published as WO 2015/120324, inventors Rikky Muller et. al. titled "Wireless High Density Micro-Electrocorticographic Device", each of which are incorporated by reference herein with the same full force and effect as if set forth in its entirety herein.

Figure 7:
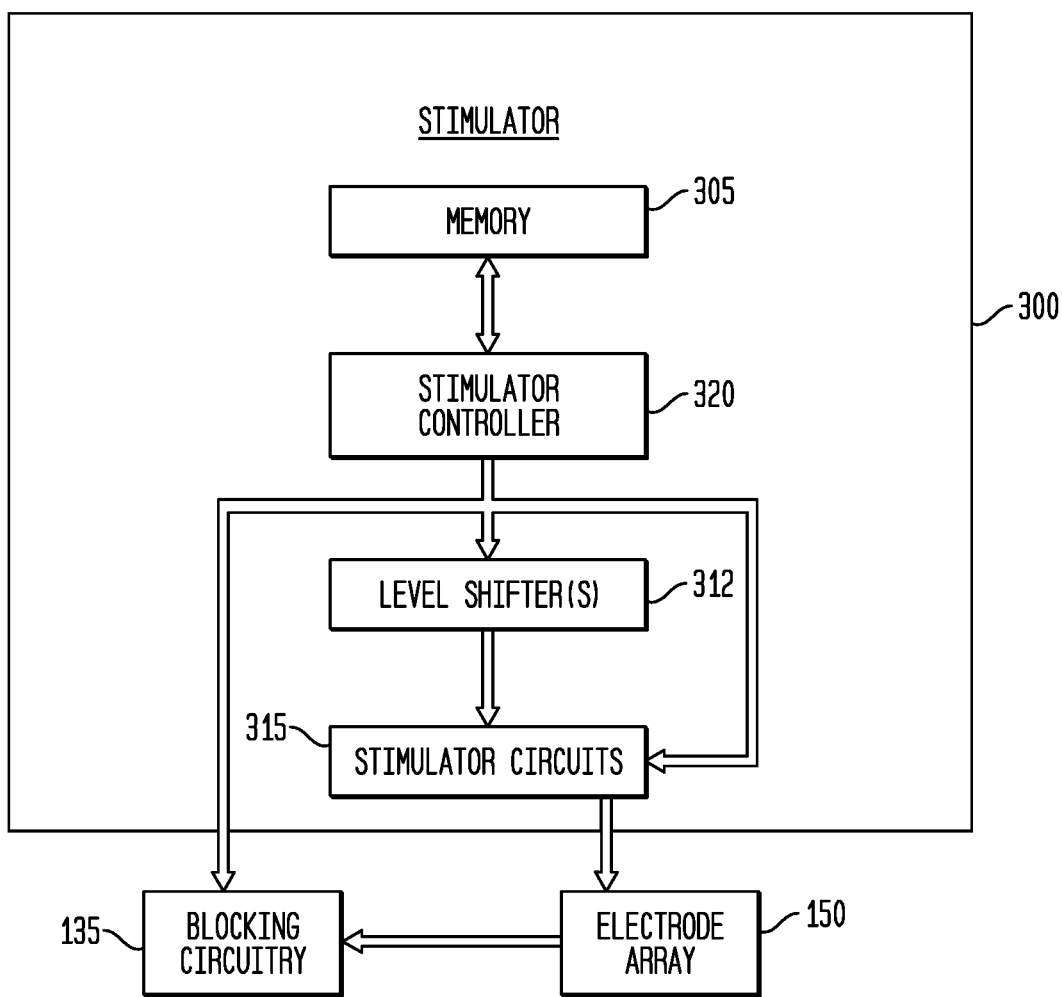
FIG. 7 is a block diagram illustrating representative stimulator and blocking circuitry for a first representative neuromodulator integrated circuit apparatus embodiment.

FIG. 7 is a block diagram illustrating stimulator circuitry 300 and blocking circuitry 135 for a first representative neuromodulator integrated circuit 100 apparatus embodiment. As illustrated in FIG. 6, the stimulator circuitry 300 is coupled to an electrode array 150 and to blocking circuitry (or circuits) 135, and the blocking circuitry 135 is also coupled to the electrode array 150, and more particularly between the electrode array 150 and the recorder (or recorder circuitry) 400. The stimulator circuitry 300 comprises a memory 305 (e.g., registers), a stimulator controller 320, stimulator circuits 315, and optional voltage level shifter(s) circuits 312 (to change the voltage level of the various control signals provided by the stimulator controller 320). Each of these components is discussed in greater detail below.

The stimulator controller 320 is a fully integrated digital controller to generate control signals to control the delivery of stimulation on selected electrodes 150 by the stimulator circuitry 300. Numerous advantages of the stimulator controller 320 will be apparent from the discussion below, including without limitation the enabling of a rapid reconfiguration of stimulation parameters, generating blocking signals to protect low voltage recorder circuitry 400, with coupling to a memory circuit 305 to store the stimulation parameters. As the NMIC 100 is a device designed to be safe and effective when implanted into a human being or any other animal, the stimulator controller 320 ensures the safe and valid operation of the stimulator circuitry 300, checking that the stimulation parameters are valid, and stopping stimulation in the event of any type of compliance error.

Figure 8:
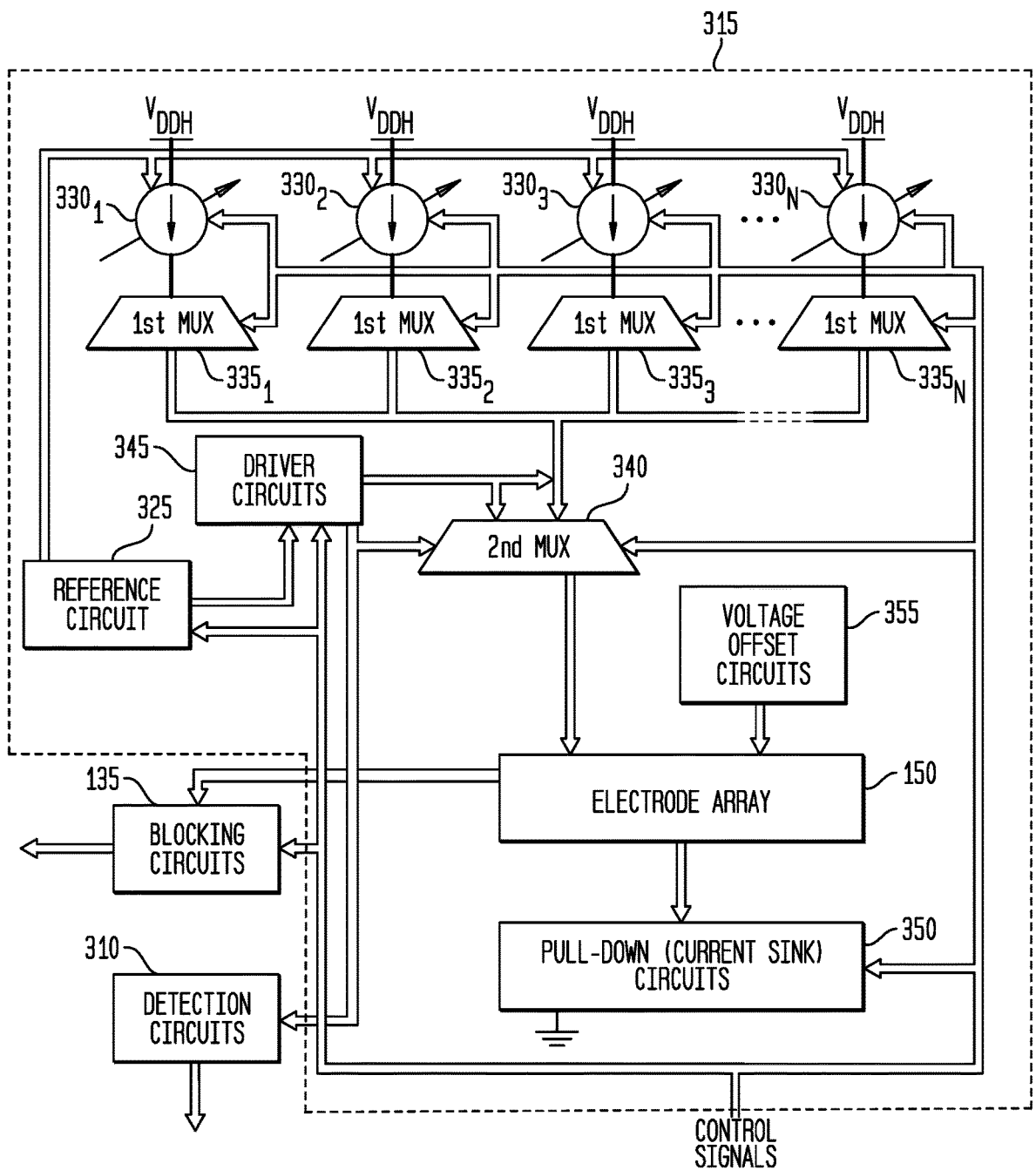
FIG. 8 is a block diagram illustrating representative stimulator circuits, detection and blocking circuitry, coupled to electrodes, for a first representative neuromodulator integrated circuit apparatus embodiment.
Figure 9:
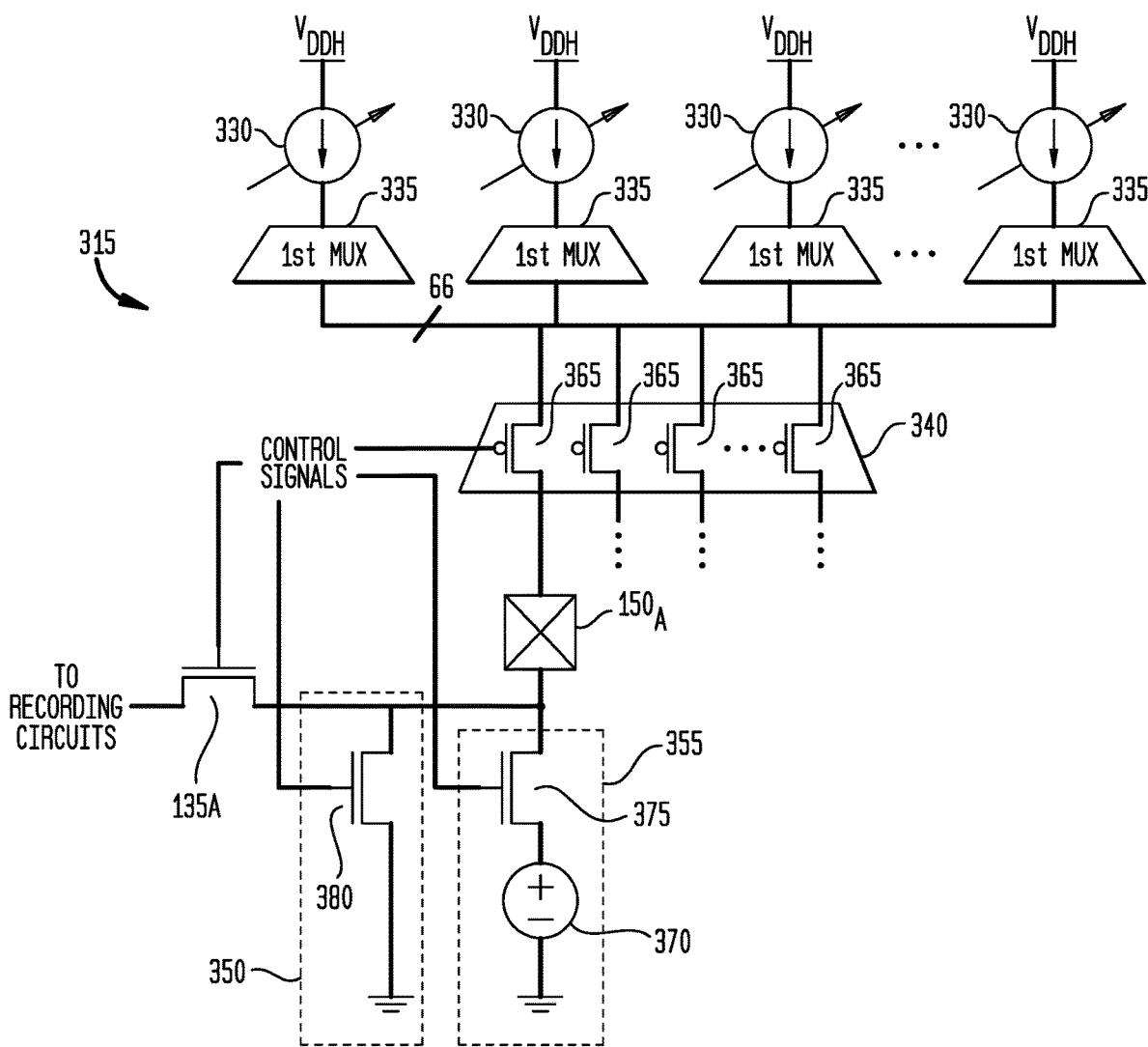
FIG. 9 is a block and circuit diagram illustrating representative stimulator circuits and blocking circuitry, coupled to electrode an electrode, for a first representative neuromodulator integrated circuit apparatus embodiment.

FIG. 8 is a block diagram illustrating representative stimulator circuits 315, detection and blocking circuitry, coupled to electrodes, for a first representative neuromodulator integrated circuit apparatus embodiment. FIG. 9 is a block and circuit diagram illustrating representative stimulator circuits 315 and blocking circuitry 135, coupled to electrode an electrode 150A, for a first representative neuromodulator integrated circuit 100 apparatus embodiment.

Figure 10:
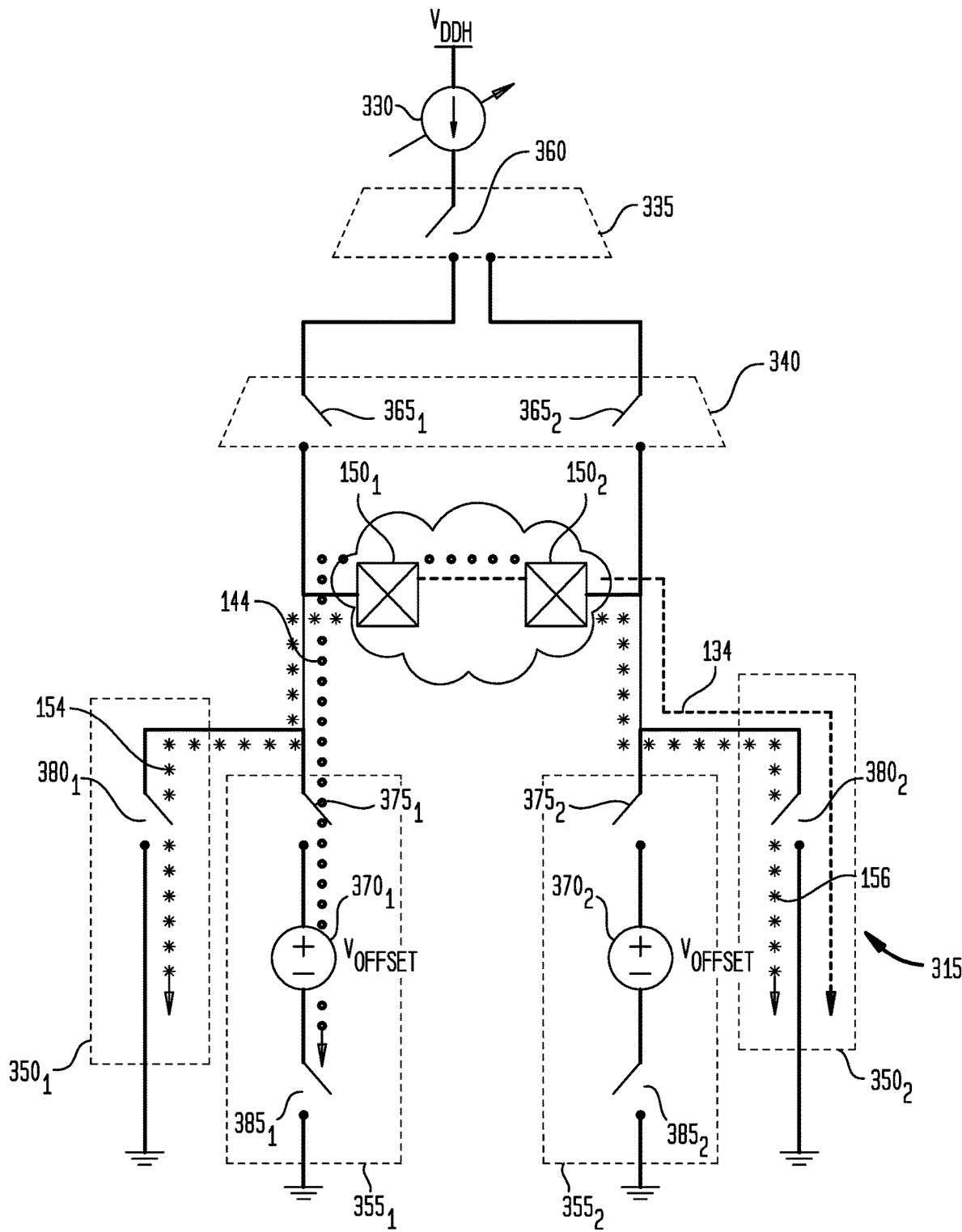
FIG. 10 is a block and circuit diagram illustrating in greater detail representative stimulator circuits, coupled to a selected pair of electrodes, for a first representative neuromodulator integrated circuit apparatus embodiment.
Figure 11:
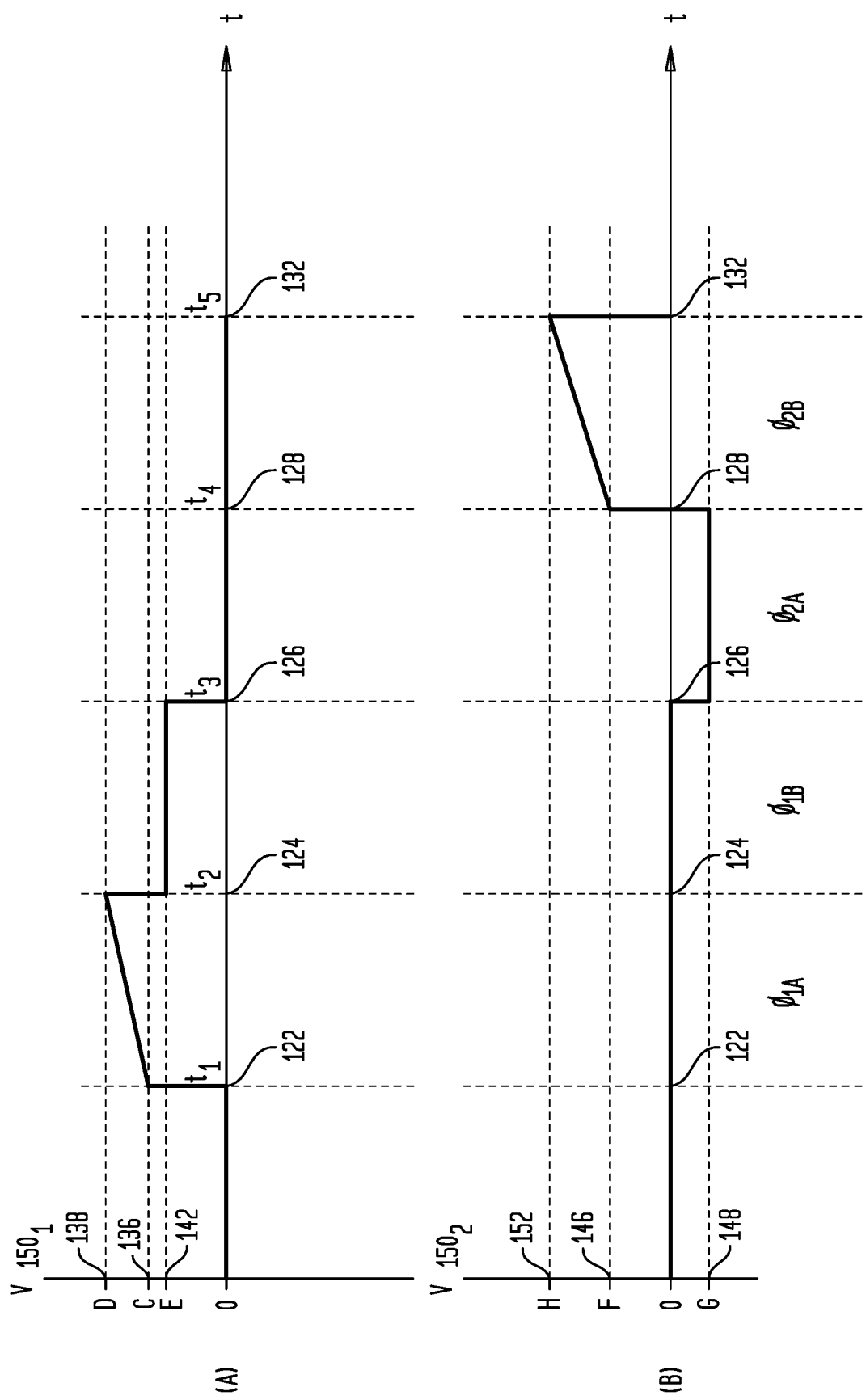
FIG. 11 is a graphical diagram illustrating representative applied voltage levels for stimulation for a first representative neuromodulator integrated circuit apparatus embodiment.

FIG. 10 is a block and circuit diagram illustrating in greater detail representative stimulator circuits 315, coupled to a selected pair of electrodes $150_A$ and $150_B$, for a first representative neuromodulator integrated circuit 100 apparatus embodiment. FIG. 11 is a graphical diagram illustrating representative applied voltage levels for stimulation for a first representative neuromodulator integrated circuit apparatus embodiment.

Referring to FIG. 8, representative stimulator circuits 315 comprise one or more controlled current sources 330, illustrated as a plurality of controlled current sources $330_1$, $330_2$, $330_3$, through $330_N$; one or more first multiplexers 335, illustrated as a plurality of first multiplexers $335_1$, $335_2$, $335_3$, through $335_N$, generally implemented as comparatively low voltage first multiplexers 335; driver circuits 345; a second multiplexer 340, generally implemented as a comparatively higher voltage second multiplexer 340; reference circuits 325; pull-down (grounding or current sink) circuits 350; and voltage offset circuits 355. The various first multiplexers 335 and second multiplexer 340 may also be implemented equivalently as one or more switches, such as the H bridge circuit illustrated in FIG. 10. As illustrated in FIG. 8, the second multiplexer 340, pull-down (grounding or current sink) circuits 350, voltage offset circuits 355, and blocking circuits 135 are coupled to the electrode array 150 or, more particularly, each of the second multiplexer 340, pull-down (grounding or current sink) circuits 350, voltage offset circuits 355, and blocking circuits 135 have components coupled to a respective electrode 150 of the plurality of electrodes 150 forming the array. In a representative embodiment, as illustrated in FIGS. 8 and 9, four controlled current sources 330 and four first multiplexers 335 are implemented, allowing up to four electrodes 150 to be energized simultaneously. A representative embodiment of a voltage offset circuit 355 is discussed below with reference to FIG. 12.

Referring to FIGS. 9 and 10, second multiplexer 340 is illustrated as comprising a plurality of switches 365 (e.g., as an H bridge circuit), typically implemented using comparatively higher voltage transistors 365, illustrated as a p-type MOSFET in FIG. 9 (although other transistors may be utilized equivalently) and illustrated as switches $365_1$ and $365_2$ in FIG. 10. The second multiplexer 340 is coupled to electrodes 150, illustrated in FIG. 10 as electrodes $150_1$ and $150_2$, which in turn are coupled respectively to voltage offset circuits $355_1$ and $355_2$, and pull-down (grounding or current sink) circuits $350_1$ and $350_2$. The second multiplexer 340, pull-down (grounding or current sink) circuits 350, voltage offset circuits 355, and blocking circuits 135 are each coupled (e.g., at respective transistor gates) to receive a corresponding control signal, from stimulator controller 320, as discussed in greater detail below. The voltage offset circuits 355 are switchable or otherwise controllable, each comprising a switch 375 typically implemented using a transistor, illustrated as an n-type MOSFET in FIG. 9 (although other transistors may be utilized equivalently) and illustrated as switches $375_1$ and $375_2$ in FIG. 10, and a voltage source 370, illustrated as voltage sources $370_1$ and $370_2$ in FIG. 10. The voltage offset circuits 355 may further comprise additional switches or transistors, illustrated as switches $385_1$ and $385_2$ in FIG. 10, to provide a comparatively faster return to ground (zero volts) following stimulation. The pull-down (grounding or current sink) circuits 350 each comprises a switch 380, typically implemented using a transistor, illustrated as an n-type MOSFET in FIG. 9 (although other transistors may be utilized equivalently) and illustrated as switches $380_1$ and $380_2$ in FIG. 10. The blocking circuits 135 are switchable or otherwise controllable, each comprising a switch 385 typically implemented using a transistor, illustrated as an n-type MOSFET in FIG. 9 (although other transistors may be utilized equivalently), typically capable of blocking a comparative high voltage level, providing that when an electrode 150 is being energized or providing a current return path (discussed below), those electrodes are blocked or otherwise disconnected from recorder circuitry 400 (i.e., blocking a high voltage on an electrode 150 from reaching any of the recorder circuitry 400).

In a representative embodiment, bipolar and biphasic stimulation is provided, using two paired electrodes (represented as electrodes $150_1$ and $150_2$ in FIG. 10), one as a source and one as a sink, and two phases of stimulation. Any two electrodes 150 may be utilized, and a generally selected based upon how far the clinician would like the electrical fields to spread within the selected tissue, with a greater distance generally requiring a more distant charge return path. Other combinations of polarity and phases are also available using NMIC 100, including bipolar and monophasic, unipolar and biphasic, and unipolar and monophasic (described in greater detail below with reference to FIGS. 16-19). For bipolar stimulation, two electrodes (of electrodes $150_1$ through $150_{N-2}$) are utilized, while for unipolar stimulation, one electrode (of electrodes $150_1$ through $150_{N-2}$) and a counter electrode $150_N$ or NMIC 100 package is typically utilized to provide a distant return path for the stimulation sequence. For biphasic stimulation, two stimulation phases are provided (as discussed in greater detail below), while for uniphasic, a single pulse waveform is provided, followed by providing a discharge path to ground.

In each of the phases of the stimulation waveform in biphasic stimulation, for a given stimulation pulse for a selected pair of electrodes 150, in a representative embodiment, the same controlled current source 330 is utilized, to provide charge balancing, matching the amount of charge between phases, so that any residual charge from a given stimulation pulse is cleared and no net charge from the stimulation accumulates in the tissue over time (which could have undesirable affects, such as hydrolysis and unwanted DC currents), and further to provide a final potential centered around ground, rather than a positive or negative voltage level. In addition, this use of the same controlled current source 330 enables the NMIC 100 to not require a negative voltage rail.

For the selected pair of electrodes, the stimulation electrode is typically one of the electrodes 150, and the other, return current path may be a selected electrode of any of the other electrodes 150, or may be a counter electrode or the device package, for example and without limitation. As is conventional in biphasic stimulation, the first pulse/phase is considered negative, to inhibit neural tissue, and the second pulse/phase is considered positive, to remove or clear residual charge from the electrodes 150. A representative bipolar and biphasic stimulation is discussed in greater detail below with reference to FIGS. 10 and 11, as an example, without limitation.

The plurality of controlled current sources 330 are shared among the electrodes 150 for stimulation. Any of the controlled current sources 330 may be selected for use during stimulation, and may be coupled to any selected electrodes 150 (or to a counter electrode or the device package), as channels, using a first multiplexer 335, and in response to one or more control signals from stimulator controller 320.

Referring to FIGS. 10 and 11, using one or more control signals from stimulator controller 320, a controlled current source 330 and the pair of electrodes 150₁ and 150₂ are selected for the stimulation, using a first multiplexer 335 of the plurality of first multiplexers 335 (illustrated as switch 360 in FIG. 10). A second multiplexer 340 (illustrated as comparatively high voltage, low resistance switches 365₁ and 365₂ in FIG. 10) is also utilized to select electrodes 150 to receive current or block electrodes 150 from receiving current from the selected controlled current source 330. Generally, one controlled current source 330 is providing current to only one electrode 150 during any given time interval. A plurality of controlled current sources 330 are provided in the NMIC 100, to generate generally arbitrary stimulation waveforms and to mix and match waveforms for different stimulation patterns. The controlled current sources 330 may be implemented using one or more transistors (as illustrated and discussed below with reference to FIG. 13), and are coupled to a comparatively high voltage (e.g., 12 V) rail ($V_{DDH}$) or voltage source, but also may be coupled to any of the other selectable voltage rails (e.g., a mid-range voltage $V_{DDM}$, a low voltage $V_{DDL}$), depending upon the selected stimulation parameters and corresponding level of stimulation. Each electrode 150 is coupled to a corresponding or respective pull-down (grounding or current sink) circuit 350 and voltage offset circuit 355, so that any selected electrode 150 may be utilized in either phase of a biphasic stimulation.

Prior to stimulation, a setup phase typically occurs in representative embodiments. For example, a stimulation enable control signal is typically generated by the stimulator controller 320, which turns on stimulation support circuitry. In addition, as mentioned below, a blocking control signal is typically generated by the stimulator controller 320, which turns on blocking circuitry 135. During stimulation, the pulse widths (or durations) and pulse amplitudes, along with electrode selection, are all determined by control signals generated by the stimulator controller 320, based upon parameters stored in configuration registers 455 (of the memory 305, discussed in greater detail below).

A first part of a first stimulation phase begins, illustrated as phase $\phi_{1A}$, using one or more control signals from stimulator controller 320, in which switch 365₁ and switch 380₂ are closed (and conducting) generally simultaneously at time $t_1$ (122), providing a current path between electrodes 150₁ and 150₂ (and to ground), illustrated in FIG. 10 using dashed line 134, and switch 365₂, switch 380₁, and voltage offset switches 375₁ and 375₂ all remain open and not conducting. More particularly, the closure or conducting of switch 380₂ occurs slightly in advance, leading slightly, so that a ground path is in place prior to energizing electrode 150₁. As illustrated in FIG. 11, the voltage on electrode 150₁ has increased initially to a first predetermined (and controllable) level "C" (136) and continues to increase to a second predetermined (and controllable) level "D" (138), typically determined by the amount of current provided through the selected controlled current source 330, and the resistance and capacitance of the tissue and electronics in the current path.

A second (or gap) part of the first stimulation phase begins at time $t_2$ (124), illustrated as phase $\phi_{1B}$, using one or more control signals from stimulator controller 320, in which switch 365₁ is opened and not conducting, and switch 380₂ remains closed and conducting, continuing to provide a current path (part of 134) to ground, and switch 365₂, switch 380₁, and voltage offset switches 375₁ and 375₂ all remain open and not conducting. As illustrated in FIG. 11, a voltage on electrode 150₁ remains but has decreased to a third predetermined (and controllable) level "E" (142) (which may or may not be the same as the voltage level "C" (136)), typically determined by the amount of capacitance and resistance of the tissue and electronics in the current path.

A first part of a second stimulation phase begins at time $t_3$ (126), illustrated as phase $\phi_{2A}$, using one or more control signals from stimulator controller 320, in which switch 375₁ is closed and conducting, and switch 380₂ is opened, all generally simultaneously, and switch 365₁, switch 365₂, switch 380₁, and voltage offset switch 375₂ all remain open and not conducting. As the voltage on electrode 150₂ is now negative with respect to ground (fourth, negative voltage level "G" (148)), a novel voltage offset is provided on electrode 150₁ in this second phase (from voltage source 370₁, such that voltage level "G" is less negative than it otherwise would be without the voltage offset), to avoid any unwanted forward biasing of the various transistors and/or substrates and switches of the NMIC 100, and to improve the matching between the first and second phases. Alternatively, when voltage offset circuits 355 are not implemented, switch 380₁ may be closed instead or in lieu of switch 375₁. For example, for bipolar and monophasic stimulation illustrated in FIG. 16, no voltage offset is provided to the electrode 150₁, and grounding may be continued instead on electrode 150₂ through switch 380₂.

A second part of a second stimulation phase begins at time $t_4$ (128), illustrated as phase $\phi_{2B}$, using one or more control signals from stimulator controller 320, in which switch 365₂ is closed and conducting and switch 375₁ remains closed and conducting, providing a return current path between electrodes 150₂ and 150₁ (and to ground) illustrated in FIG. 10 using dotted line 144, and switch 365₁, switch 365₂, switch 380₁, switch 380₂, and voltage offset switch 375₂ all remain open and not conducting. As illustrated in FIG. 11, the voltage on electrode 150₂ has now increased (from its previously negative level) initially to a fifth predetermined (and controllable) level "F" (146) (with the overall voltage increment from voltage level "G" to voltage level "F" generally substantially equal to voltage level C"), and continues to increase to a sixth predetermined (and controllable) level "H" (152), also typically determined by the amount of current provided through the same selected controlled current source 330, and the resistance and capacitance of the tissue and electronics in the current path.

The second part of the second stimulation phase, and the overall stimulation sequence for this selected stimulation pulse sequence, ends at time $t_5$ (132), also referred to as a shorting interval or "$t_{SHORT}$"), using one or more control signals from stimulator controller 320, in which switch 365₂ and switch 375₁ are opened and not conducting, and switches 380₁ and 380₂ are closed and conducting, providing a return current path between electrodes 150₂ and 150₁ and ground, illustrated in FIG. 10 using asterisk lines 154 and 156, and switch 365₁, switch 365₂, and voltage offset switches 375₁ and 375₂ all remain open and not conducting. As an option, voltage offset switches 385₁ and 385₂ also may be closed and conducting. In this way, the pull-down (grounding or current sink) circuits 350 (illustrated as switches 380₁ and 380₂ in FIG. 10), and any optional voltage offset switches 385₁ and 385₂), enable a rapid return of the electrodes 150₁ and 150₂ to a zero (ground) voltage level, enabling these electrodes 150 to be quickly utilized for recording or for additional stimulation sequences, as may be necessary or desirable.

Not separately illustrated in FIG. 11, following the second part of the second stimulation phase (phase $\phi_{2B}$), but prior to commencement of the shorting interval at time $t_5$ (132), there may be a waiting interval, under the control of the stimulator controller 320, waiting for all second stimulation phases to end for all electrodes 150. For this intervening waiting interval, all stimulation for the selected electrode 150 may stop (e.g., switch $365_2$ and/or switch $375_1$ are opened and not conducting), but pull-down switches $380_1$ and $380_2$ remain open and not conducting. This helps to avoid unwanted interaction between different electrodes 150 which may be providing stimulation while other electrodes 150 have ceased a stimulation cycle.

As mentioned above, while selected electrodes 150 are utilized for stimulation, other electrodes 150 may be utilized simultaneously for recording. This allows, for example, simultaneous recording of responses to the stimulation and the various fields generated by the stimulation, such as voltage transients, in addition to the recording of other tissue (e.g., brain) activity.

As mentioned above and as illustrated in FIGS. 8-11, the stimulator circuitry 300 of the representative NMIC 100 re-uses the same current source (330) for both phases of stimulation in biphasic mode, to improve matching between the phases, across a plurality of channels, as the voltage across the current source 330 is the same for both phases. A highly inventive voltage offset (370) is generated during the second phase, to eliminate negative voltages from charge transfer, improving the charge balancing between the phases, and further providing a better matching with the current source 330 with different voltage levels at the electrodes 150. In addition, the stimulation is centered around a ground potential, starting and returning to zero volts, as illustrated in FIG. 11, without requiring any negative voltage supply or rail, making full use of the voltage headroom, and further being compatible with low-voltage recording circuitry 400.

Figure 12:
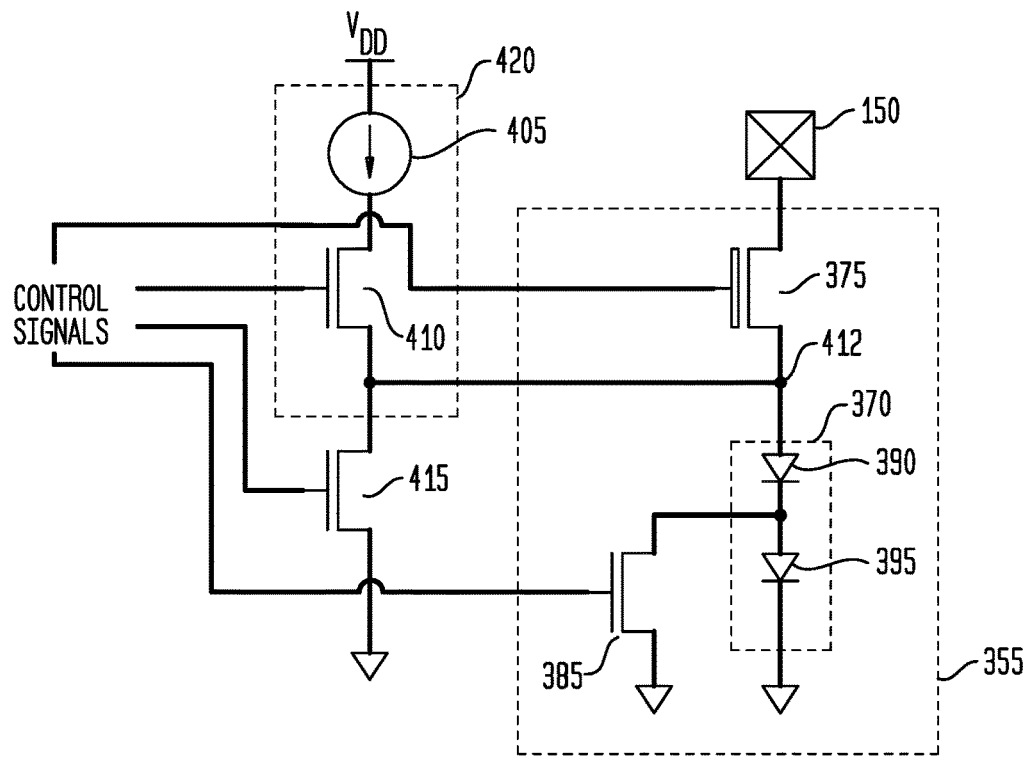
FIG. 12 is a circuit diagram illustrating a representative embodiment of a voltage offset circuit for a first representative neuromodulator integrated circuit apparatus embodiment.

FIG. 12 is a circuit diagram illustrating a representative embodiment of a voltage offset circuit 355 for a first representative neuromodulator integrated circuit 100 apparatus embodiment. As illustrated in FIG. 12, a representative voltage offset circuit 355 may be implemented using one or more diodes 390, 395 to create an offset voltage at node 412, which is pre-charged using pre-charge circuit 420, providing a comparatively small current from current source 405 to diodes 390, 395, when a transistor (or other switch) 410 (e.g., a comparatively low voltage MOSFET) is turned on and is conducting, using one or more control signals from stimulator controller 320. The offset voltage is discharged using transistor (or other switch) 385, as discussed above, and transistor (or other switch) 415 (which may be substituted for transistor (or other switch) 380). As illustrated, the value of the offset voltage may be varied based upon the level of the current from the current source 405 or the number of the one or more diodes 390, 395. Not separately illustrated, additional switches (e.g. transistors) may be utilized to generate multiple offset voltages, which can be switched to the electrodes 150, using one or more control signals from stimulator controller 320.

Figure 13:
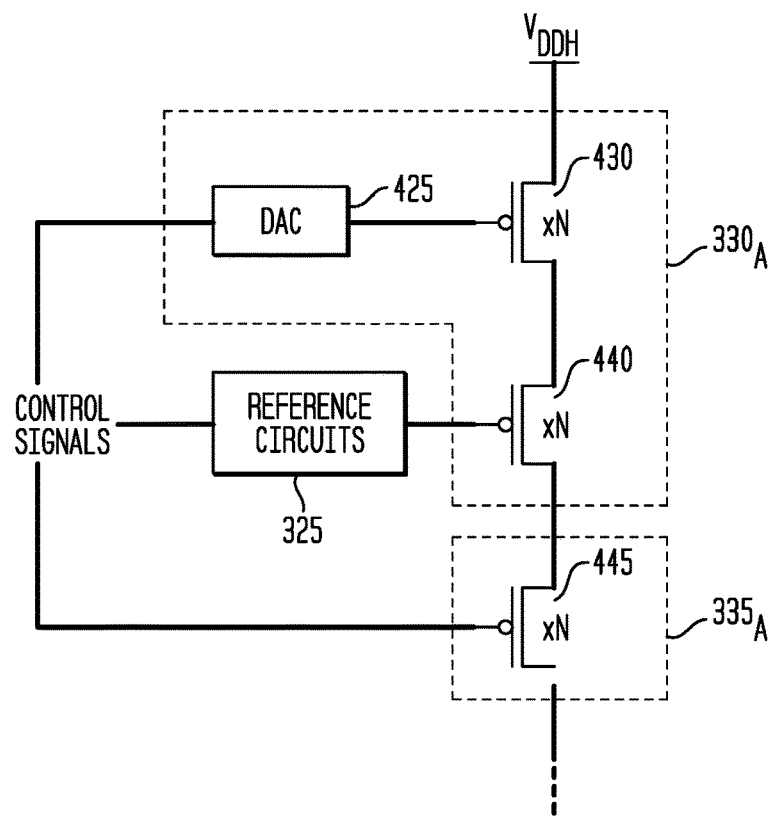
FIG. 13 is a block and circuit diagram illustrating representative embodiments of controlled current source circuitry, reference circuits, and first multiplexer circuitry for a first representative neuromodulator integrated circuit apparatus embodiment.

FIG. 13 is a block and circuit diagram illustrating representative embodiments of controlled current source $330_A$ circuitry, reference circuits 325, and first multiplexer $335_A$ circuitry for a first representative neuromodulator integrated circuit apparatus embodiment. As illustrated in FIG. 13, each controlled current source $330_A$ comprises a transistor (or switch) 430 which provides a variable current based upon its input voltage, which in turn is provided by a digital-to-analog converter ("DAC") 425, under the control of the stimulator controller 320 (i.e., using one or more control signals from stimulator controller 320). The DAC 425 may be implemented as known or becomes known in the electronic arts, and acts as a binary-weighted switch, with an increased voltage output correspondingly generating increased current levels. Each controlled current source $330_A$ further comprises a transistor (or switch) 440 coupled to a reference circuit 325, such as a current mirror reference circuit 325A discussed in greater detail below, which are also controlled using one or more control signals from stimulator controller 320. A plurality of "N" controlled current sources $330_A$ are provided in a representative NMIC 100, such as four controlled current sources $330_A$ (e.g., N=4). A representative first multiplexer $335_A$ is also implemented, using a comparatively low voltage transistor (or switch) 445, also controlled using one or more control signals from stimulator controller 320. A plurality of "N" transistors (or switches) 445 are provided in each first multiplexer $335_A$ in a representative NMIC 100, one for every electrode 150 and for the NMIC 100 package, such as sixty-six transistors (or switches) 445 (e.g., N=66), for an electrode array having 64 electrodes $150_1$ through $150_{N-2}$, one reference electrode $150_{N-1}$, one counter electrode $150_N$, and one NMIC 100 package.

Figure 14:
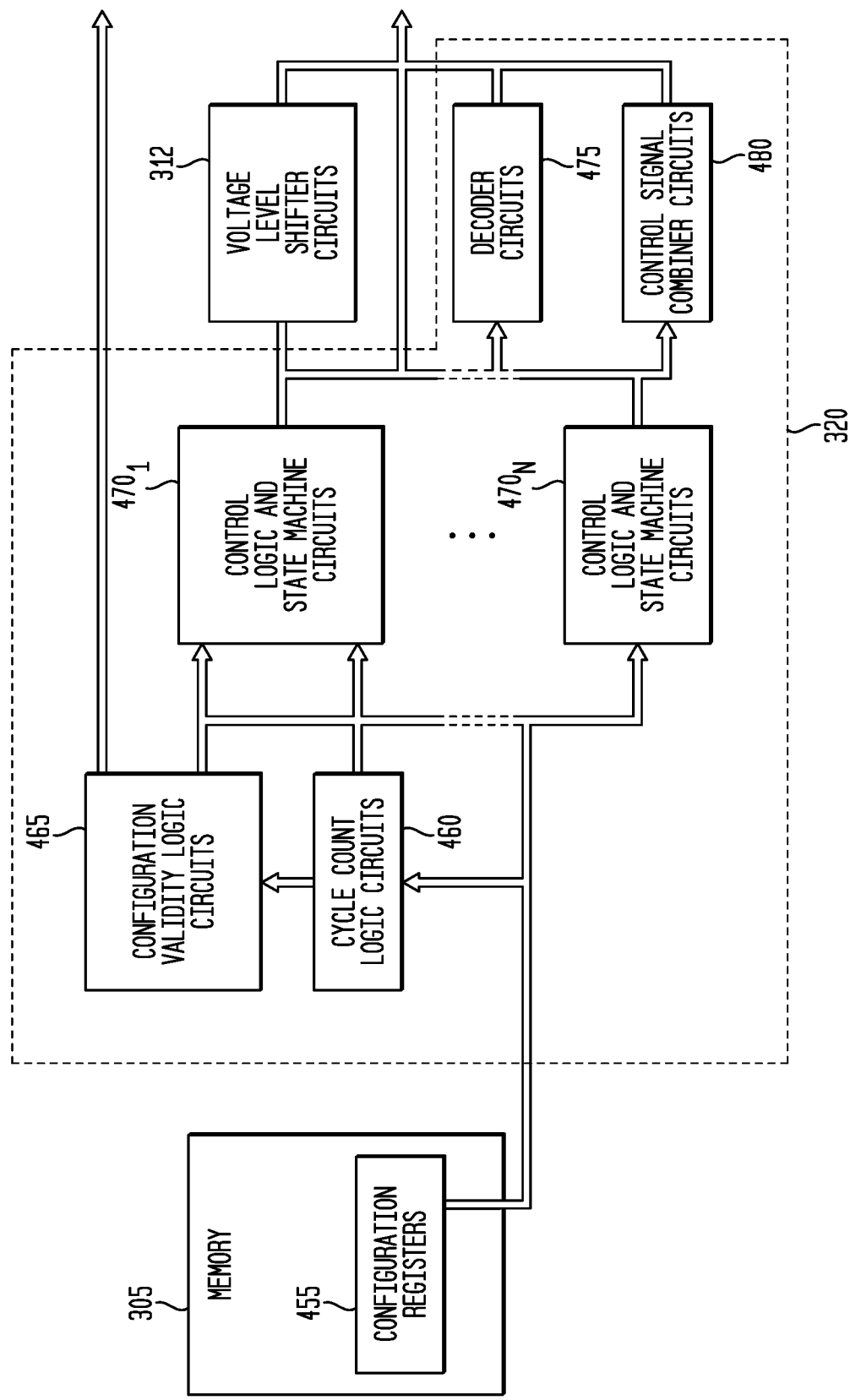
FIG. 14 is a block diagram illustrating a representative embodiment of a stimulator controller 320 for a first representative neuromodulator integrated circuit apparatus embodiment.

FIG. 14 is a block diagram illustrating a representative embodiment of a stimulator controller 320 for a first representative neuromodulator integrated circuit apparatus embodiment. Referring to FIG. 14, a representative stimulator controller 320 is coupled to a memory 305, which comprises one or more configuration registers 455, for example and without limitation. The one or more configuration registers 455 contain information (stored in binary form) for the parameters and/or other settings which will be utilized in a stimulation program for the given individual, typically as established by a clinician, as discussed above, such as which electrodes 150 will be utilized to provide stimulation, in what sequence, at what amplitudes and durations, and other parameters, also for example and without limitation. A representative stimulator controller 320 generally comprises a plurality ("N") of control logic and state machine circuits 470, generally one for each controlled current source 330, illustrated as control logic and state machine circuits $470_1$, $470_2$, through $470_N$, each of which is also coupled to the one or more configuration registers 455 to receive relevant parameters.

The control logic and state machine circuits 470 are generally implemented utilizing a plurality of combinational logic gates, counters, and flip-flops to provide state information for a finite state machine ("FSM"). The control logic and state machine circuits 470 generally count the number of clock cycles to transition between states, using a counter and FSMs, based upon the parameters stored in the configuration registers 455. One such state transition is between an overall idle state, in between stimulation cycles, and an active stimulation state. There are additional states within the active stimulation state, in which the FSMs transition to a next state (or remain in a current state), as follows: an idle state (in between stimulation cycles), which may transition to a setup state, which may transition to a first part of the first stimulation phase (phase $\phi_{1A}$) state, which may transition to a second part of the first stimulation phase (phase $\phi_{1B}$ or gap) state, which may transition to a second stimulation phase (phase $\phi_{2A}$, $\phi_{2B}$), which may transition to any waiting phase state, which may transition to a shorting interval state, which may transition to the idle state.

The representative stimulator controller 320 further comprises cycle count logic circuits 460, configuration validity logic circuits 465, decoder circuits 475, and control signal combiner circuits 480. The cycle count logic circuits 460 are utilized to provide the timing or duration between stimulation pulses or cycles (e.g., a waiting phase), and provides corresponding control signals to the control logic and state machine circuits 470, usually based on a clock signal having a frequency of 128 kHz. The configuration validity logic circuits 465 provide a validity check for the configuration information, and when valid, generate a gated start signal to the control logic and state machine circuits 470 to allow stimulation, and otherwise, when invalid, generate an invalid configuration signal (as one of the control signals which may be utilized to stop stimulation after any stimulation cycle which is currently in process is completed). The decoder circuits 475 are utilized to convert an electrode 150 address (combined with a selection signal) into a level shifted (higher voltage) electrode 150 selection signal ("eSELX_HV<0:63>") provided to the second multiplexer 340 (comprised of comparatively higher voltage switches or transistors 365), to provide electrode 150 selection.

The control logic and state machine circuits 470 generate a plurality of control signals, based upon the stored, valid configuration parameters. The control signals include, for example and without limitation:

(1) A selection control signal for selecting both an electrode 150 ("e" prefix or counter electrode "c" prefix) and controlled current source 330 ("A", "B", "C", or "D" suffix for selection of up to four controlled current source 330) (e.g., "eSELA", "cSELA"). This selection signal is generally combined with the electrode address, as mentioned above, to provide the electrode 150 selection signal ("eSELX_HV<0:63>") provided to the second multiplexer 340, selecting both the controlled current source 330 and the electrode 150 for stimulation.

(2) Pull down control signals (e.g., "cPD" for a counter electrode, "ePD<address or number "N">" for any of the "N" electrodes 150), to activate the various pull-down (grounding or current sink) circuits 350 (e.g., switches or transistors 375, 380, 385).

(3) Blocking control signals (e.g., eBLOCK<address or number "N">) to activate the blocking circuitry 135 (e.g., switches or transistors 385).

(4) Pre-charge control signals ((e.g., pre_ch<address or number "N"> or a global precharge "pre_ch") to pre-charge the voltage level of the voltage offset circuits 355, as discussed above, to activate transistor (or switch) 410.

(5) An electrode address control signal (e.g., "eADDX<address or number "N">") designating the electrode for stimulation or other control.

(6) A stimulation enable control signal (e.g., "stim_en", "en_support_circuitry") as a gating signal to turn on the stimulation circuitry near (i.e., just prior to the planned start of) a stimulation event.

(7) Clocking control signals.

Many of the control signals from any of the various control logic and state machine circuits 470 may also be combined, using control signal combiner circuits 480, such as to combine various pull down, pre-charge, and stimulation enable control signals, for example and without limitation.

The stimulator controller 320 is a fully integrated digital controller to generate control signals to control the delivery of stimulation on selected electrodes 150 by the stimulator circuitry 300. Numerous advantages of the stimulator controller 320 include, for example and without limitation, the enabling of a rapid reconfiguration of stimulation parameters, generating blocking signals to protect low voltage recorder circuitry 400, with coupling to a memory circuit 305 to store the stimulation parameters. The stimulator controller 320 also checks that the stimulation parameters are valid, and stops stimulation in the event of any type of compliance error.

Figure 16:
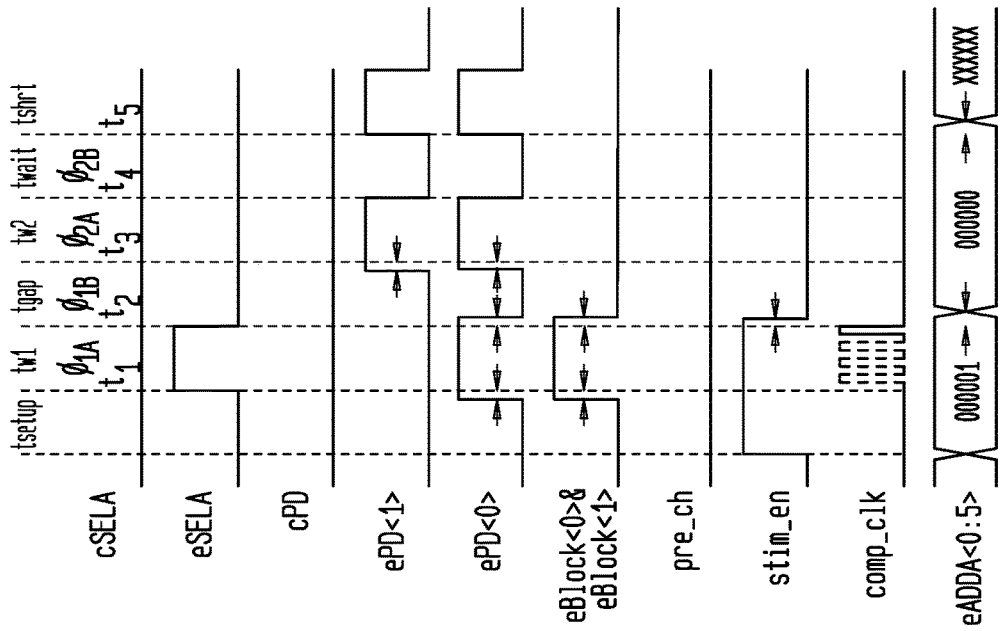
FIG. 16 is a graphical diagram illustrating bipolar and monophasic control signal timing for a first representative neuromodulator integrated circuit apparatus embodiment.
Figure 15:
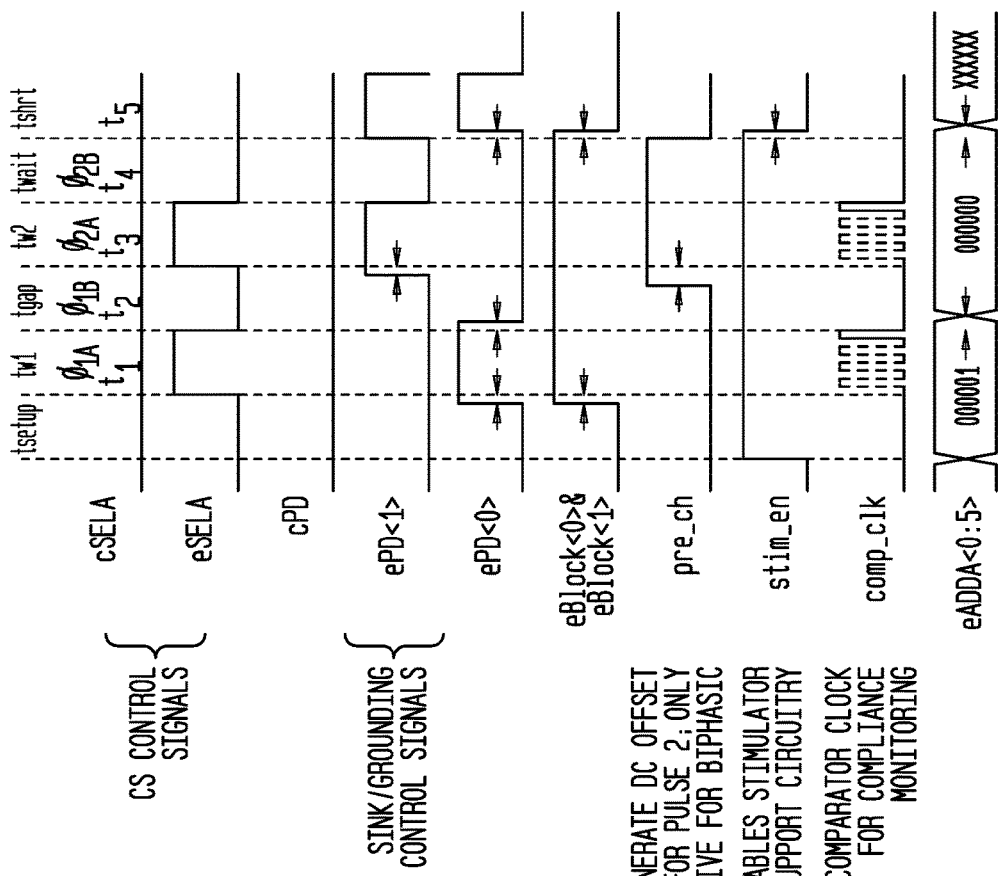
FIG. 15 is a graphical diagram illustrating bipolar and biphasic control signal timing for a first representative neuromodulator integrated circuit apparatus embodiment.

Representative examples of the timing and states of each of these various control signals are illustrated in FIGS. 15-18. FIG. 15 is a graphical diagram illustrating bipolar and biphasic control signal timing for a first representative neuromodulator integrated circuit apparatus embodiment. Such bipolar and biphasic stimulation was discussed above, and is further discussed below with reference to FIG. 28. FIG. 16 is a graphical diagram illustrating bipolar and monophasic control signal timing for a first representative neuromodulator integrated circuit apparatus embodiment. This bipolar and monophasic stimulation and control pattern differs from the bipolar and biphasic stimulation discussed above insofar as no stimulation is provided to a second electrode $150_2$, no voltage offset is provided to the first electrode $150_1$, and instead grounding continues on the second electrode $150_2$, as mentioned above.

Figure 17:
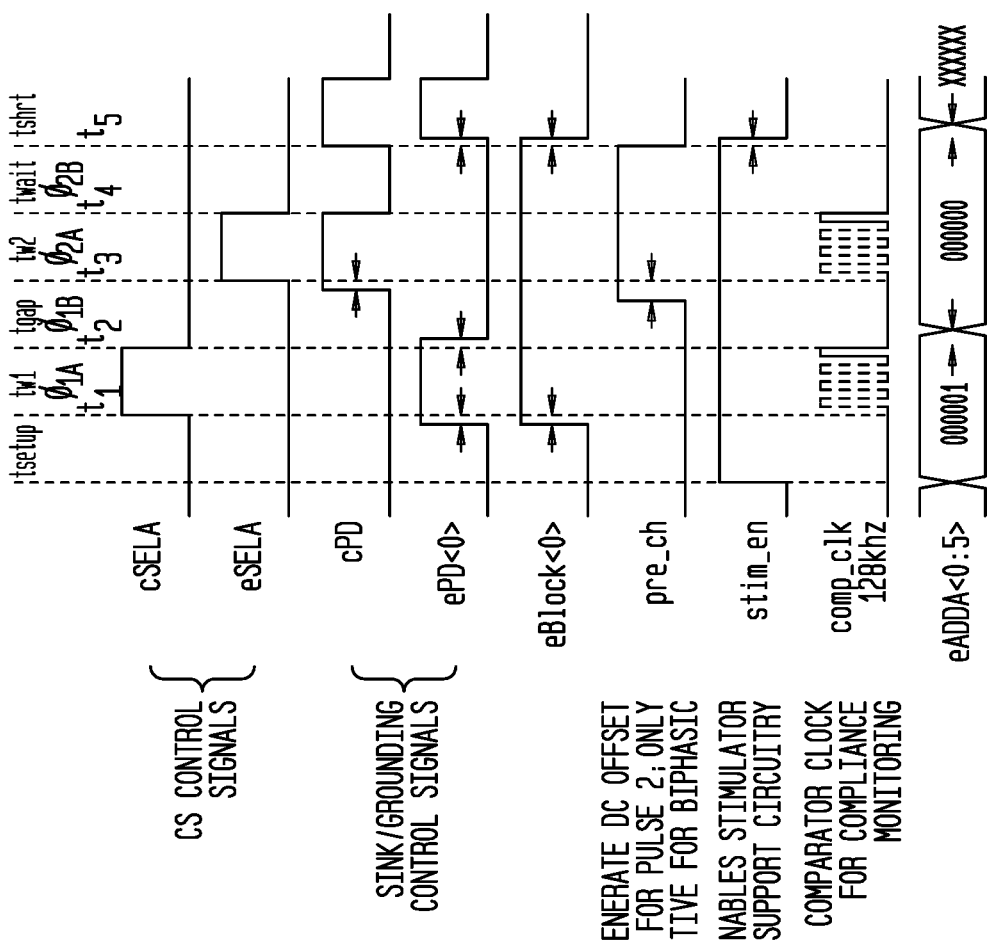
FIG. 17 is a graphical diagram illustrating unipolar and biphasic control signal timing for a first representative neuromodulator integrated circuit apparatus embodiment.

FIG. 17 is a graphical diagram illustrating unipolar and biphasic control signal timing for a first representative neuromodulator integrated circuit apparatus embodiment, and differs from the bipolar and biphasic stimulation discussed above insofar as a counter electrode $150_N$ is utilized as a first electrode instead of another type of electrode 150 (e.g., electrode $150_1$).

Figure 18:
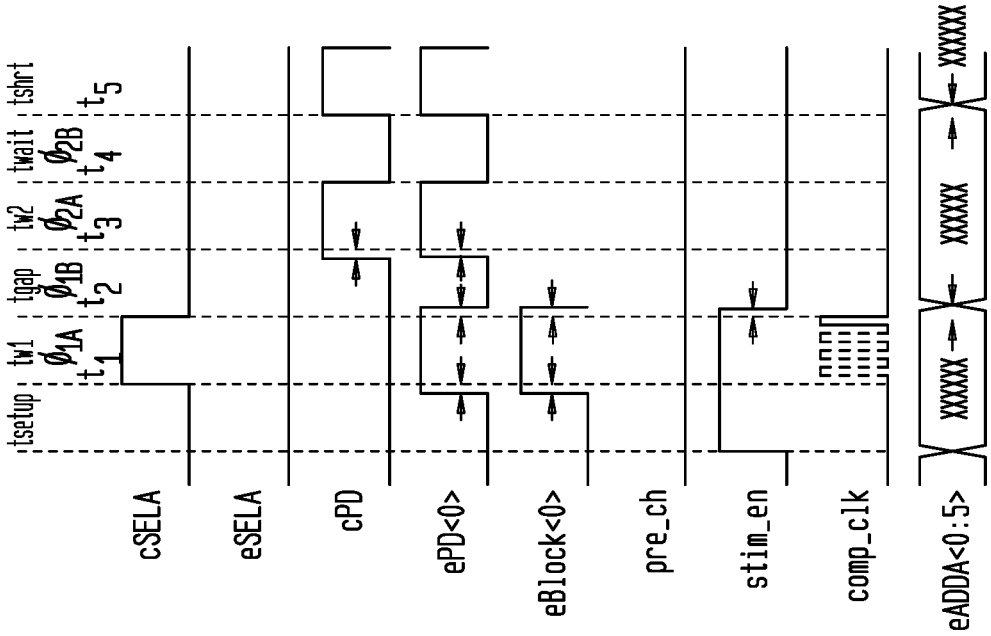
FIG. 18 is a graphical diagram illustrating unipolar and monophasic control signal timing for a first representative neuromodulator integrated circuit apparatus embodiment.

FIG. 18 is a graphical diagram illustrating unipolar and monophasic control signal timing for a first representative neuromodulator integrated circuit apparatus embodiment. This unipolar and monophasic stimulation and control pattern differs from the bipolar and biphasic stimulation discussed above insofar as a counter electrode $150_N$ is utilized instead of another type of electrode 150, and further that no stimulation is provided to a second electrode $150_2$, no voltage offset is provided to the first electrode $150_1$ (or counter electrode $150_N$ in this case), and instead grounding continues on the second electrode $150_2$, as mentioned above.

Figure 19:
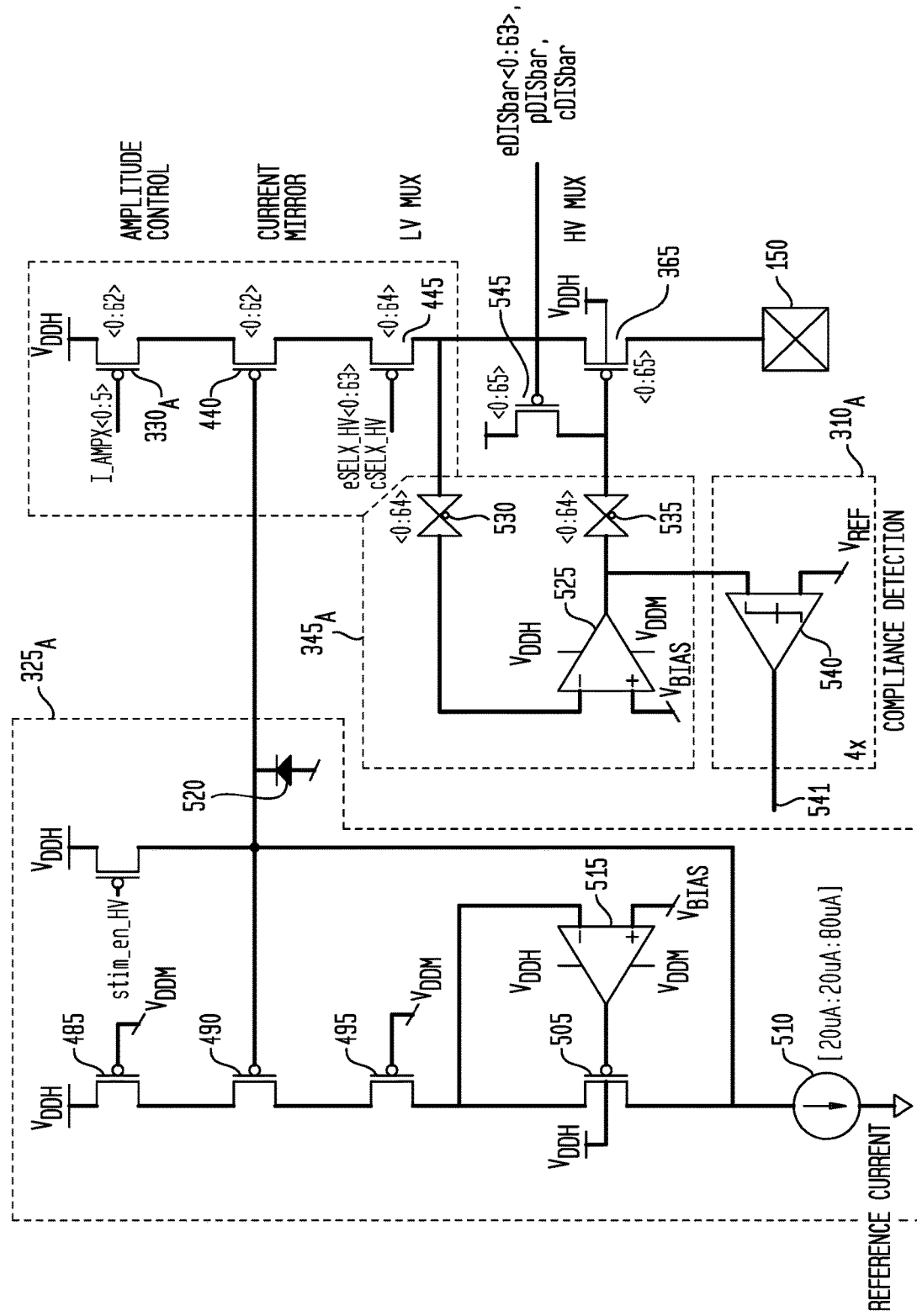
FIG. 19 is a block and circuit diagram illustrating representative embodiments of reference circuits, driver circuits, and detection circuits for a first representative neuromodulator integrated circuit apparatus embodiment.

FIG. 19 is a block and circuit diagram illustrating representative embodiments of a reference circuit 325A, driver circuit 345A, and detection circuit 310A for a first representative neuromodulator integrated circuit apparatus embodiment. A representative embodiment of a reference circuit 325A is implemented as high voltage FET mirror circuitry, using a plurality of series-coupled FETs 485, 490, 495, and 505. FETs 485 and 495 have respective gates coupled to a mid-level voltage rail ($V_{DDM}$), FET 490 is coupled (with diode 520) to the mirror transistor (FET) 440 of a first multiplexer 335, and FET 505 is coupled at its gate to an operation amplifier 515 and at its source to a reference current generator 510 (implemented as a constant Gm circuit using a high voltage FET mirror). Establishing a first reference voltage at the gate of the mirror transistor (FET) 440 of a first multiplexer 335, reference circuit 325A enables use of comparatively low voltage transistors in the first multiplexer 335.

A representative embodiment of a driver circuit 345A comprises an operation amplifier 525, having its negative (or inverting) input coupled through transmission gate 530 to the source of the transistor 445 of the first multiplexer 335, also establishing a second reference voltage at the source of the transistor 445 (also enabling use of comparatively low voltage transistors in the first multiplexer 335). A plurality ("N") of the driver circuits 345A are provided, typically one for every controlled current source 330 (e.g., N=4). Transmission gates 530, 535 are addressable and switchable to any of the electrodes 150, using one or more control signals from stimulator controller 320, to provide electrode 150 selection through the second multiplexer 340. The output of the operation amplifier 525 is coupled through transmission gate 535 to the gate of (comparatively high voltage) transistor 365 of the second multiplexer 340 to provide a predetermined amount of drive current into the transistor 365.

A detection circuit 310A is implemented as a comparator 540 coupled to the output of the operation amplifier 525, and the output 541 of the comparator 540 is coupled to the serial digital interface and system monitor 155 (not separately illustrated), providing a fault signal to the serial digital interface and system monitor 155 if the drive current generated by the operation amplifier 525 is less than a predetermined level, indicative of a fault condition in the NMIC 100.

A disable circuit implemented using transistor (FET) 545 is also illustrated in FIG. 19, which will disable (force to be off and not conducting) transistor 365 of the second multiplexer 340, in response to a control signal from stimulator controller 320.

As mentioned above, the stimulator 300 circuit architecture enables use of both high and low voltage devices, with an adjustable power supply, such as for higher voltage stimulation and lower voltage recording, and even lower voltage rails for operation of the logic gates, flip flops, and state machines, for example. Also for example and without limitation, and as discussed in greater detail below, the first programmable power converter 120 and the second programmable power converter 125 each provide variable voltage levels, for fine-grained control over stimulation, enabling use of both low and high voltage components in the same integrated circuit, with multiple voltage rails, sufficient headroom in the event of a decreased input voltage, and providing significant power savings, especially important in an implantable device having a limited power supply, such as a battery.

Figure 20:
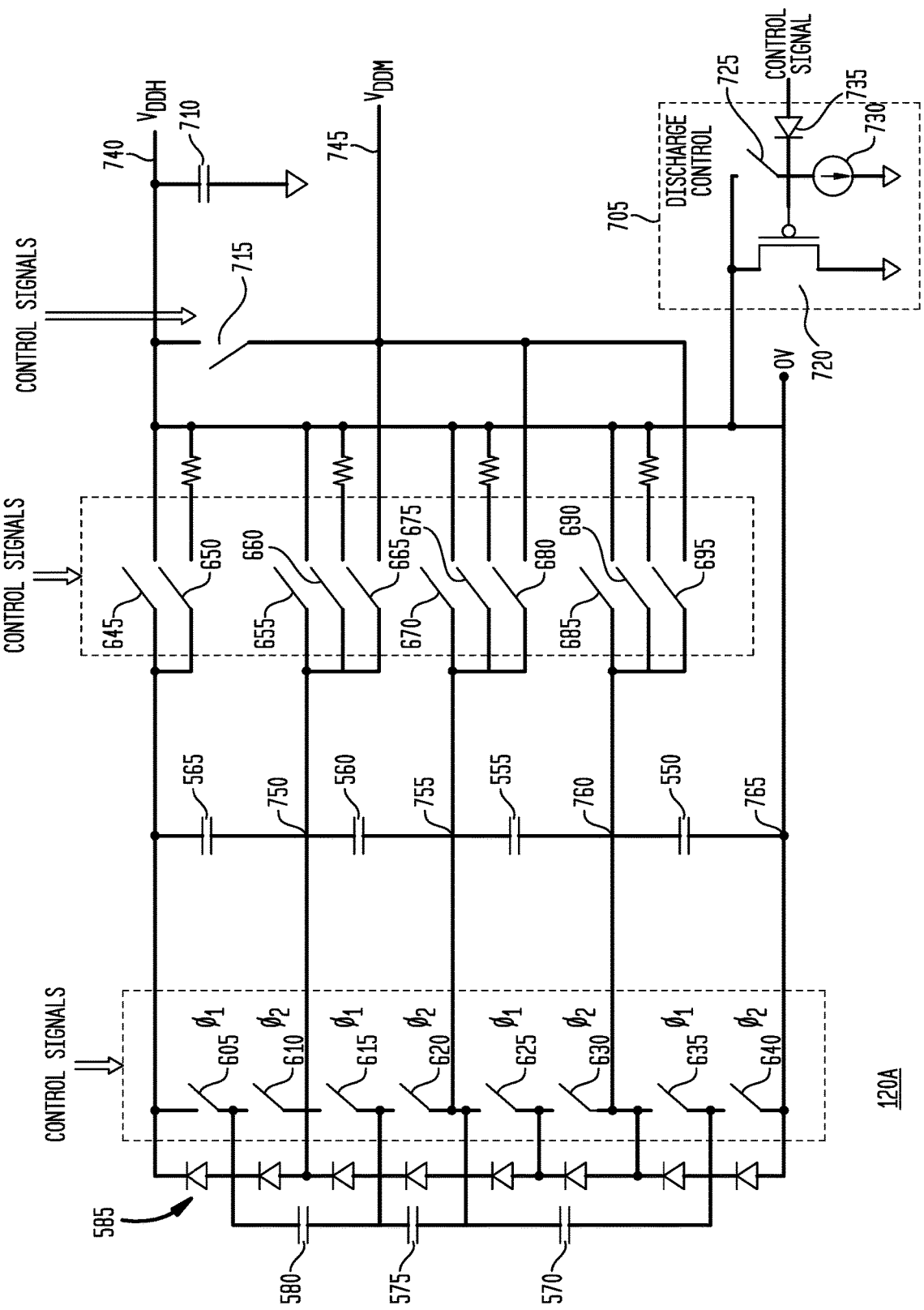
FIG. 20 is a circuit diagram illustrating a representative embodiment of a first programmable power converter for a first representative neuromodulator integrated circuit apparatus embodiment.

FIG. 20 is a circuit diagram illustrating a representative embodiment of a first programmable power converter 120A for a first representative neuromodulator integrated circuit apparatus embodiment. The first programmable power converter 120A utilizes a plurality of switchable stages to generate a plurality of different voltage levels which, in a representative embodiment, are each separated by a predetermined increment, providing a voltage "ladder" having a plurality of switchable voltage rails (nodes 740, 750, 755, 760, 765), such as three volts, providing 12 V ($V_{DDH}$), 9 V, 6 V, and 3 V levels at node 740, and 9 V, 6 V, and 3 V levels at node 745, any one of which may be selected to be a mid-range voltage level ($V_{DDM}$). Those having skill in the art will recognize that any of a plurality of different voltage levels may be generated, in addition to the 12 V ($V_{DDH}$), 9 V, 6 V, and 3 V levels indicated, and any and all such variations are considered equivalent and within the scope of the disclosure.

Discharge control circuitry 705 is also provided, both to generate a lower voltage level from a previous, higher voltage level, such as to change the voltages at nodes 740, 745 from any higher voltage level to a lower voltage level, and to completely discharge any stimulation voltage or current (e.g., $V_{DDH}$ provided to a current source 330). In addition, such lower voltages may also be switched dynamically within the NMIC 100 and used to provide power savings.

In a representative embodiment, capacitor 550 is a comparatively low voltage capacitor, and capacitor 710 is a comparatively high voltage capacitor, both of which are arranged or otherwise located externally to the NMIC 100 (but within the NMIC 100 packaging), while the other capacitors 555, 560, 565, 570, 575, and 580 are typically within the NMIC 100. Diodes 585 may be body diodes of corresponding switches (implemented as transistors such as FETs) or may be separate diodes. Switches 605, 610, 615, 620, 625, 630, 635, 640, 645, 650, 655, 660, 665, 670, 675, 680, 685, 690, 695, 715, 720, 725 are typically implemented as transistors such as FETs (e.g., 3 V junction isolated transistors), and are controlled to be closed and conducting (or open and not conducting) using one or more control signals from the system controller 900, discussed in greater detail below.

During operation, as a phase 1 (ø1), switches 605, 615, 625, and 635 are closed (using the control signals from the system controller 900) and conducting, while switches 610, 620, 630, and 640 remain open and not conducting (also using the control signals from system controller 900), and any charge on capacitor 550 is transferred to capacitor 570, any charge on capacitor 555 is transferred to capacitor 575, and any charge on capacitor 560 is transferred to capacitor 580. During operation, as a phase 2 (ø2), switches 610, 620, 630, and 640 are closed and conducting (using the control signals from the system controller 900), while switches 605, 615, 625, and 635 are opened and not conducting (also using the control signals from the system controller 900), and any charge on capacitor 570 is transferred to capacitor 555, any charge on capacitor 575 is transferred to capacitor 560, and any charge on capacitor 580 is transferred to capacitor 565. After a number of repetitions of phases 1 and 2, a first predetermined voltage level is at node 740 (e.g., 12 V), a second predetermined voltage level is at node 750 (e.g., 9 V), a third predetermined voltage level is at node 755 (e.g., 6 V), a fourth predetermined voltage level is at node 760 (e.g., 3 V), while node 765 remains at zero volts. Using any of switches (typically implemented as a multiplexer) 645, 650, 655, 660, 670, 675, 685, or 690, selected using the control signals from the system controller 900), any of these corresponding voltages may be provided as outputs to node 740 (e.g., as a predetermined high voltage level $V_{DDH}$ for the stimulation circuitry). Similarly, using any of switches (also typically implemented as a multiplexer) 715, 665, 680, or 695, selected using the control signals from the system controller 900), any of these corresponding voltages may be provided as outputs to to node 745 (e.g., as a selectable, predetermined mid-range voltage level $V_{DDM}$ for lower voltage logic applications, as a floating rail), such as 9 V, 6 V, or 3 V, for example and without limitation.

When a lower voltage (i.e., lower than the current voltage) is to be selected for any of these voltage rails (nodes 740 and 745), discharge control circuit 705 is utilized, also using one or more control signals from the system controller 900, and which discharges external capacitor 710 until it has reached the desired voltage level of the selected voltage rail of the voltage ladder. In sequence, all of the switches 605, 610, 615, 620, 625, 630, 635, 640, 645, 650, 655, 660, 665, 670, 675, 680, 685, 690, and 695 are opened, and switch 715 is closed, shorting $V_{DDH}$ at node 740 to the mid-voltage rail $V_{DDM}$ at node 745. The discharge control circuit 705 is then activated until the external capacitor 710 is discharged. To provide the next selected voltage level, using one or more control signals from the system controller 900, one of the (equalizing) switches 650, 660, 675, or 690 is selected and closed, to be on and conducting, slowly recharging the external capacitor 710 to the desired voltage level of the corresponding voltage rail. To maintain another, lower voltage at node 745 (VDDM), using one or more control signals from the system controller 900, the switch 715 is then opened and one of the switches 655, 670, or 685 is selected and closed, to be on and conducting, providing the next selected lower voltage level at node 745.

The first programmable power converter 120A provides significant flexibility, managing the comparatively high voltage external capacitor 710 while avoiding overvoltage conditions and disrupting the converter 120A, along with having the capability to selectively increase and decrease voltage levels on corresponding voltage rails. No voltage sensing is required, and RC time constants may be utilized instead, with a selected switching frequency and output impedances of the various capacitors.

In a representative embodiment, a plurality of first programmable power converters 120A are implemented, operating at a comparatively small phase shift (e.g., 90 degrees) from each other, for smoother power delivery with decreased ripple.

The discharge control circuit 705, as illustrated in a representative embodiment, is implemented as a large PMOS source-follower circuit. The control signals from system controller 900 may be input via a multiplexer (not separately illustrated), and when operative (switch 725 is on and conducting), discharges until a matching voltage is provided at the gate of transistor 720.

Figure 21:
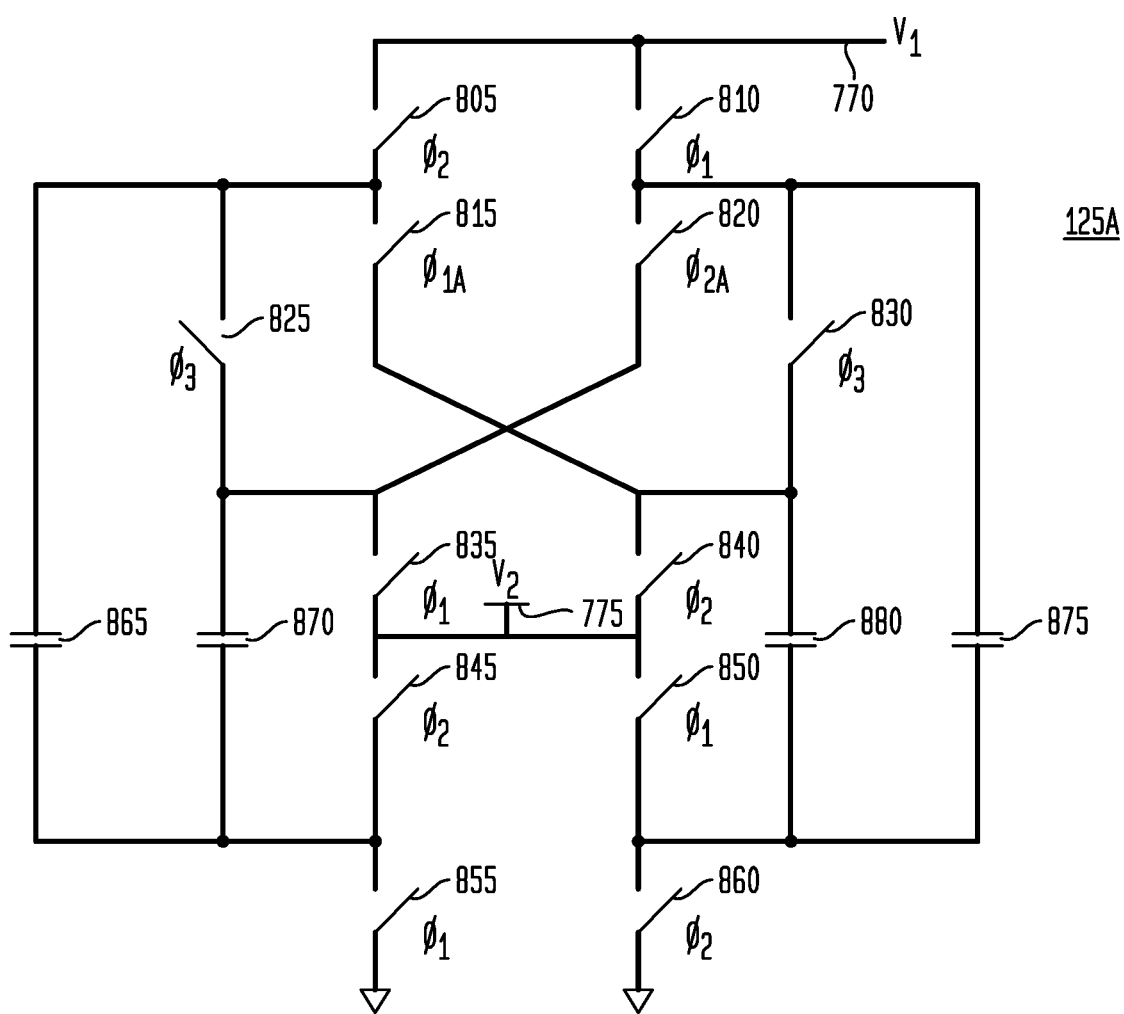
FIG. 21 is a circuit diagram illustrating a representative embodiment of a second programmable power converter for a first representative neuromodulator integrated circuit apparatus embodiment.

FIG. 21 is a circuit diagram illustrating a representative embodiment of a second programmable power converter 125A for a first representative neuromodulator integrated circuit apparatus embodiment. The second programmable power converter 125A is utilized in the NMIC 100 to selectively provide a 1:2 and 1:3 voltage level conversion, such as to generate one or more comparatively lower voltage rails (V2, at node 775), such as 1 V or 1.5 V rails, selectable using one or more control signals from the system controller 900, from an input 3 V rail (V1, at node 770), for example and without limitation. In addition, such voltage rails may also be switched dynamically within the NMIC 100 and used to provide power savings, and also to provide enough voltage headroom in the event of a decreased input voltage. Those having skill in the art will recognize that any of a plurality of different voltage levels may be generated, in addition to the 1 V and 1.5 V levels indicated, and any and all such variations are considered equivalent and within the scope of the disclosure.

The second programmable power converter 125A comprises a plurality of capacitors 865, 870, 875, and 880. Capacitors 865 and 875 typically have a first capacitance which is the same for both capacitors, such as 2 V or 1.5 V, and capacitors 870 and 880 typically have a second capacitance which is the same for both capacitors, such as 1 V or 1.5 V. The second programmable power converter 125A further comprises a plurality of switches (805, 810, 815, 820, 825, 830, 835, 840, 845, 850, 855, and 860), typically implemented using transistors such as FETs, which are controlled using one or more control signals from system controller 900, and also are operated in several phases, $\phi 1$, $\phi 2$, and $\phi 3$. Phases one and two are utilized to provide a first conversion ratio of, for example, 3:1, providing a 1 V rail at node 775 from an input 3 V voltage rail at node 770. Phase three is utilized to provide a second conversion ratio of, for example, 2:1, providing a 1.5 V rail at node 775 from an input 3 V voltage rail at node 770.

During a first part of phase one, $\phi 1$, switches 810, 835, 850, and 855 are closed and conducting, using one or more control signals from the system controller 900, and the remaining switches are open and not conducting. This connects capacitor 875 in series between V1 (at node 770) with capacitor 870 and ground, charging capacitors 875 (e.g., to 2 V) and 870 (e.g., to 1 V). During a first part of phase two, $\phi 2$, this is done symmetrically, with switches 805, 845, 840, and 860 being closed and conducting, using one or more control signals from the system controller 900, and the remaining switches are open and not conducting. This connects capacitor 865 in series between V1 (at node 770) with capacitor 880 and ground, charging capacitors 865 (e.g., to 2 V) and 880 (e.g., to 1 V).

In a second part of phase two, $\phi 2A$, switches 820, 845, 840, and 860 are closed and conducting, using one or more control signals from the system controller 900, and the remaining switches are open and not conducting. This allows capacitor 875 to discharge into the series-connected capacitors 870 and 880, effectively splitting or equally dividing the voltage on capacitor 875 across the capacitors 870 and 880. Depending upon the selected capacitance values, the voltage across capacitor 880 is provided as V2 at node 775, e.g., 1 V.

In a second part of phase one, $\phi 1A$, this is done symmetrically, with switches 815, 850, 835, and 855 being closed and conducting, using one or more control signals from the system controller 900, and the remaining switches are open and not conducting. This allows capacitor 865 to discharge into the series-connected capacitors 880 and 870, effectively splitting or equally dividing the voltage on capacitor 865 across the capacitors 870 and 880. Depending upon the selected capacitance values, the voltage across capacitor 870 is provided as V2 at node 775, e.g., 1 V.

To switch to a different voltage level (or conversion ratio), a phase three is utilized, following the first parts of phases one and two (not utilizing phases $\phi 1A$ and $\phi 2A$). With the capacitors having been charged in the first parts of phases one and two, $\phi 1$ and $\phi 2$, during a phase three, $\phi 3$, switches 815 and 820 are opened and not conducting, and switches 825, 830, 835, 840, 855 and 860 are closed and conducting, and the remaining switches are open and not conducting, using one or more control signals from the system controller 900. This puts capacitors 865 and 870 in parallel, and puts capacitors 875 and 880 in parallel, so that the total capacitance for each pair of capacitors is the sum of their individual capacitances. Depending upon the selected capacitance values, the voltage across capacitors 865 and 870, and across capacitors 880 and 875, is provided as V2 at node 775, e.g., 1.5 V.

Figure 22:
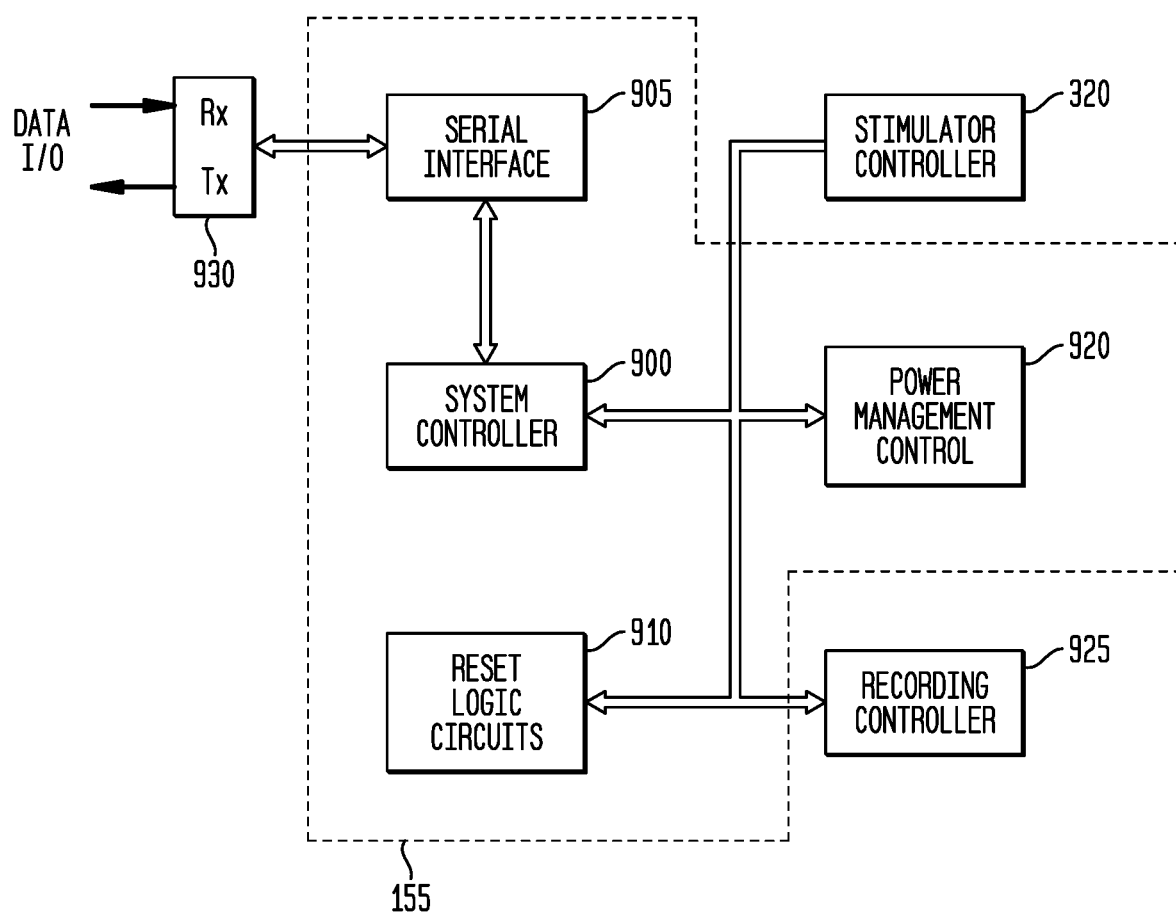
FIG. 22 is a block diagram illustrating a representative embodiment of a serial digital interface and system monitor for a first representative neuromodulator integrated circuit apparatus embodiment.

FIG. 22 is a block diagram illustrating a representative embodiment of a serial digital interface and system monitor 155 for a first representative neuromodulator integrated circuit 100 apparatus embodiment. As illustrated in FIG. 22, a representative serial digital interface and system monitor 155 comprises a serial interface 905 (coupled to transceiver 930), a system controller 900, reset logic circuits 910, and power management controller 920. Depending upon the selected embodiment, the power management controller 920 may be included within the system controller 900. The system controller 900 is also coupled to the stimulator controller 320 and typically also to a recording controller 925. A representative system controller 900 may be implemented or embodied as a state machine, combinational logic gates, or otherwise as described in greater detail below.

The serial interface 905 provides for data communication to and from the NMIC 100. The system controller 900 is adapted to determine if an error condition or other potentially detrimental condition exists, and if so, to put the NMIC 100 into a safe mode, either inhibiting any additional stimulation or shutting the NMIC 100 down altogether.

When data is received from the serial interface 905, the system controller 900 will check for errors in the data, such as errors in the stimulation program or parameters, typically using a cyclic redundancy check ("CRC"). In addition, the stimulator controller 320 may also generate error conditions, including compliance errors (as mentioned above) and also parameter errors, which are provided to the system controller 900. The reset logic circuits 910 typically provide for a power on reset signal to the system controller 900.

For certain kinds of errors or other conditions, the system controller 900 will issue a stimulation inhibition command, effectively shutting down or otherwise disabling stimulation circuits, until the inhibition is lifted, such as through correction of the error condition. Either a CRC error or a power on reset signal will cause the system controller 900 to generate such an inhibition command and disable stimulation, typically after the current stimulation cycle has been completed. This inhibition is typically temporary for the power on reset signal, and is lifted once the NMIC 100 has fully initialized.

Other errors, such as compliance errors (electrical problems, insufficient current) and parameter errors, will shut down selected circuitry altogether, including the stimulation circuitry, and some of the power management circuitry, including the first programmable power converter 120, the second programmable power converter 125, and will further cause the various capacitors to discharge.

The system controller 900 also monitors the derived clock signal, determining if clock edges exist, and if not, generates a system reset, which stops all circuitry and discharges capacitors. A reset timer may also be initiated, which is asserted for a predetermined number of clock cycles, so that the NMIC 100 remains reset until appropriate clocking has returned and the clock cycle count has been achieved.

Errors are also generally latched into a status register of the serial interface 905. This allows the system controller and power supply 180 and/or the programming device 190 to interrogate the NMIC 100 to determine the error.

As discussed in greater detail below, among other measurements and parameters which may be determined, the recorder circuitry 400 is also capable of measuring the electrical impedance of the electrodes 150 once implanted. The system controller and power supply 180 typically issues a command to the NMIC 100 during system 200, 210, 220, 230, 240 initialization to perform these various measurements. This data is transmitted through the serial interface 905 via transceiver 930 to the system controller and power supply 180, and also generally stored in the various memories and registers of the NMIC 100. In turn, the system controller and power supply 180 utilizes these various measurements to determine which electrodes 150 may be stimulated and at what levels (pulse duration and amplitude, for example). As part of system 200, 210, 220, 230, 240 initialization, various biomarkers are typically computed from the various recordings, by the system controller and power supply 180, which then configures the NMIC 100 for the various therapy parameters, as mentioned above. For example, depending upon the amount and level of stimulation, the NMIC 100 will select any of the plurality of voltage levels which may be provided by the first and second programmable power converters 120, 125. Typically, the system controller and power supply 180 generates and transmits commands for recording (by recorder circuitry 400) on a regular basis, and receives the corresponding data, providing for generally continuous closed-loop monitoring of the relevant activity of the subject activity.

Figure 23:
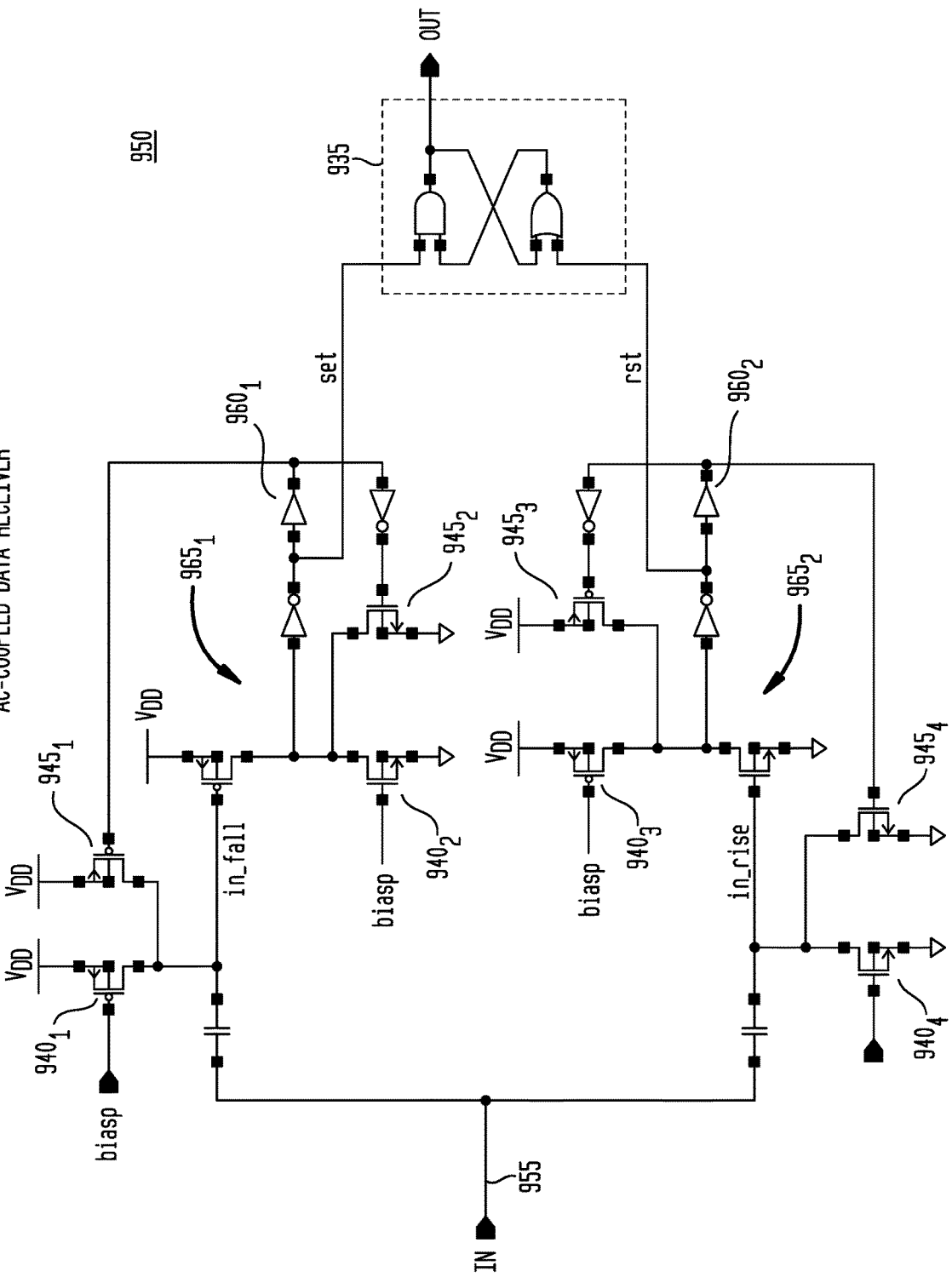
FIG. 23 is a circuit diagram illustrating a representative embodiment of an AC-coupled data receiver for a first representative neuromodulator integrated circuit apparatus embodiment.

As mentioned above, the data communication to and from the NMIC 100 is digital, packet-based communication, via the serial interface 905, which is typically synchronous. Any communication protocol may be utilized equivalently. In various selected embodiments of the NMIC 100 and system 200, 210, 220, 230, 240 representative data communication packets will have a header (such as an address header designating the selected NMIC 100 and a packet type, such as a command packet or a data read or write request packet, including read and write acknowledgements). Depending upon the type of packet, such as for a data read or data write, the data packet will also typically have a register address and a data payload, or a command code, and also error correction data, such as a plurality of bits for a cyclic redundancy check. Other types of data packets may also provide various alarm codes (or bits) or error codes (or bits), such as for alarm conditions on the NMIC 100 or data transmission (CRC) errors, respectively, as mentioned above The transmission circuitry of the transceiver 930 may be implemented as known in the electronic arts, such as using one or more buffer circuits. FIG. 23 is a circuit diagram illustrating a representative embodiment of an AC-coupled data receiver 950 (of transceiver 930) for a first representative neuromodulator integrated circuit apparatus embodiment. As mentioned above, differential signaling is implemented in a representative NMIC 100, so first and second AC-coupled data receivers 950 are respectively coupled to a corresponding pair of differential inputs (955). Each AC-coupled data receiver 950 provides rising and falling edge detection, from which the transmitted data is reconstructed. FIG. 23 illustrates a representative AC-coupled data receiver 950, using one-shot circuitry 965 (illustrated as one-shot circuitry $965_1$ and $965_2$), coupled to delay circuits 960 (illustrated as delay circuits $960_1$ and $960_2$), which in turn provide corresponding signals to the SR latch 935. Current sources 940 (illustrated as current sources $940_1$, $940_2$, $940_3$, and $940_4$) and reset switches 945 (illustrated as reset switches $945_1$, $945_2$, $945_3$, and $945_4$) are also provided in the AC-coupled data receiver 950.

Figure 24:
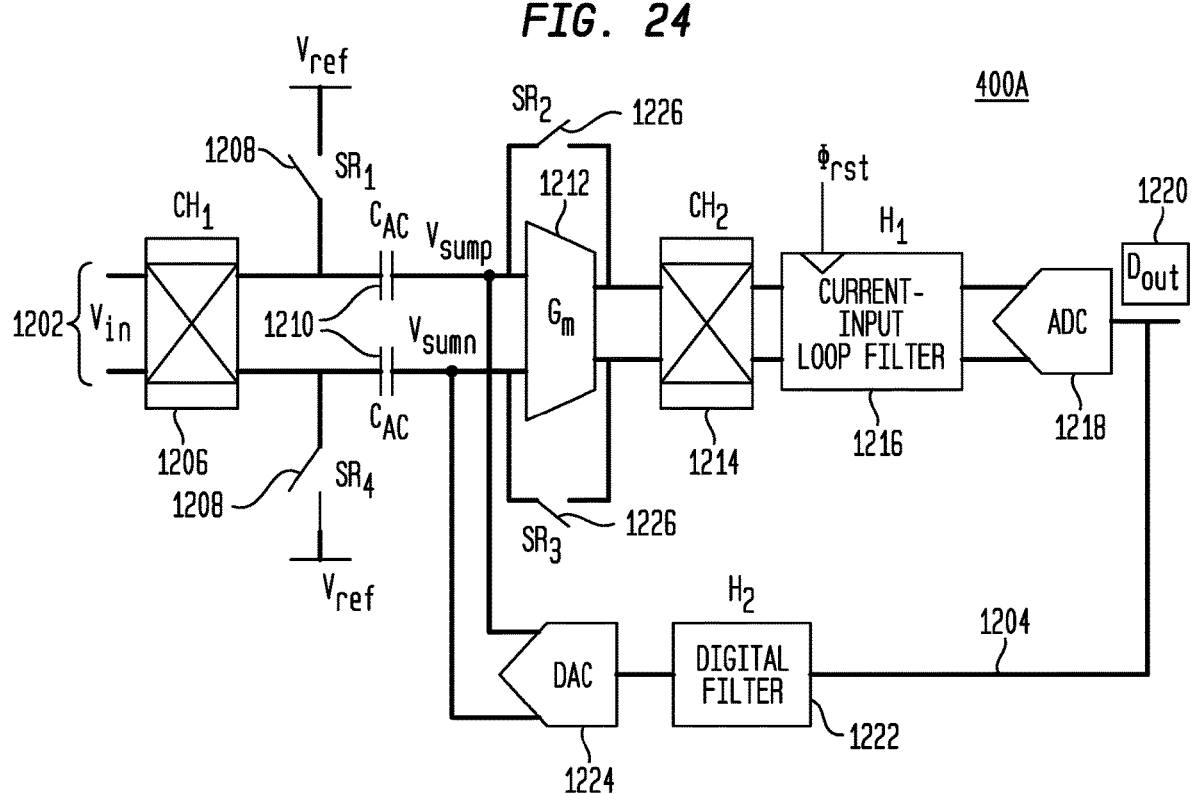
FIG. 24 is a block diagram providing a schematic view of a first embodiment of neural recording circuitry with a feedback loop.
Figure 25:
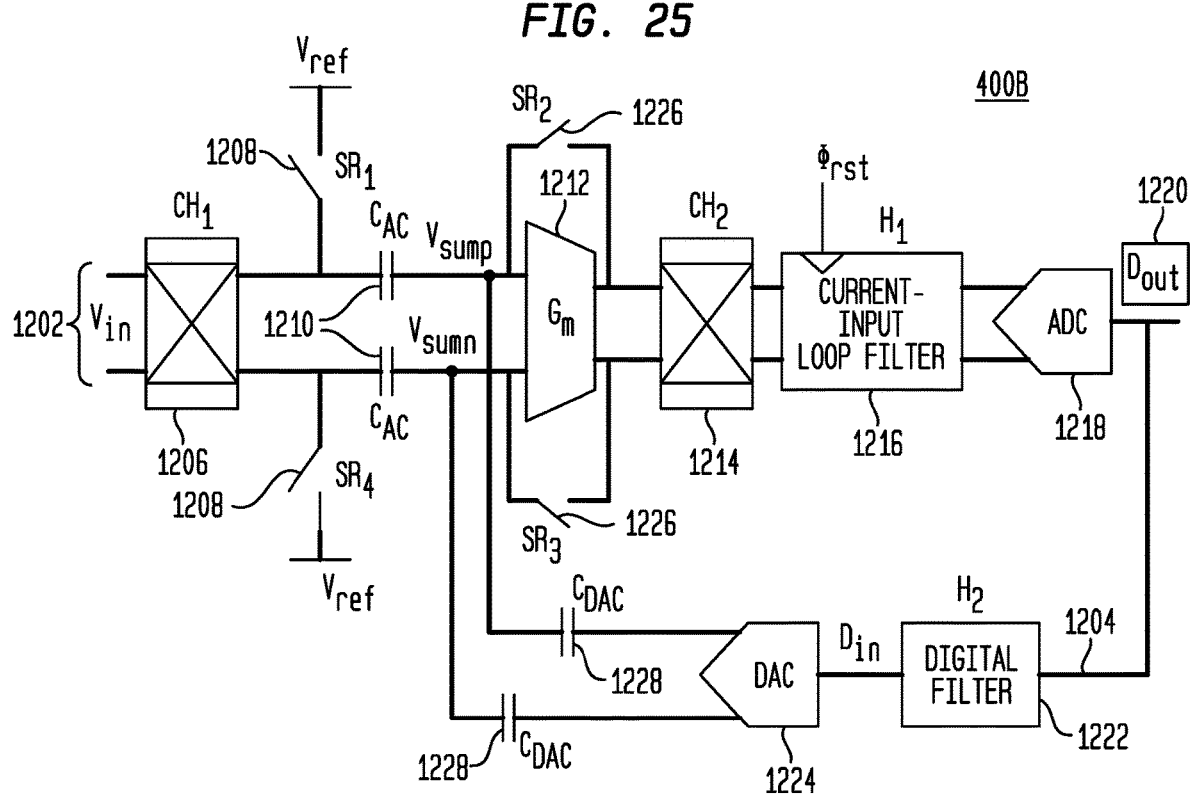
FIG. 25 is a block diagram providing a schematic view of a second embodiment of a neural recording circuitry incorporating a continuous time voltage-to-current converter, switched capacitor, and mixed-signal feedback path.
Figure 26:
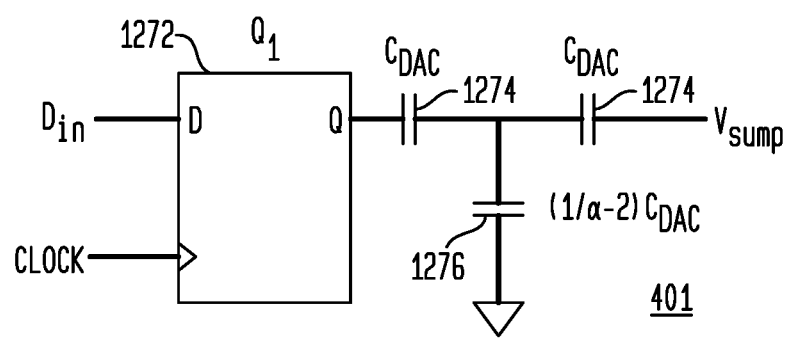
FIG. 26 is a block diagram providing a schematic diagram of a third embodiment of neural recording circuitry using a capacitive T-network.

FIG. 24 through FIG. 26 are block diagrams illustrating representative embodiments of recorder circuitry 400 with extended linear range, precise gain and increased input impedance in accordance with the present description. In a representative embodiment, recorder circuitry 400 comprises a plurality of separate recording circuits (e.g., 400A, 400B, 400C and/or 400D), one for each channel, namely, one for each electrode 150 (except the counter electrode $150_N$ and reference electrode $150_{N-1}$), e.g., in a representative NMIC 100 embodiment, 64 separate recording circuits (e.g., 400A, 400B, and/or 400C) are provided for a corresponding 64 electrodes $150_1$ through $150_{N-2}$.

Referring to FIG. 24 recorder circuitry 400A includes a feedback loop. The forward path 1202 of the feedback loop comprises a chopper-stabilized voltage-to-current converter, where the chopper down-modulation is applied to the output current, followed by a current-input loop filter 1216 and an analog-to-digital converter (ADC) 1218.

The feedback path 1204 comprises a digital filter 1222 and a D/A converter (DAC) 1224. In recorder circuitry 400A, transconductor Gm 1212 performs a voltage-to-current conversion and drives the current input loop filter $H_1$ 1216. The current input loop filter 1216 is preferably (but not exclusively) an integrator, and provides low-frequency gain. The transconductor Gm 1212 is chopper-stabilized by analog multipliers CH1 1206 and CH2 1214, and driven by frequency $f_{CHOP}$. Since the transconductor Gm 1212 is embedded in a feedback loop, recorder circuitry 400A directly digitizes the electrode signal plus an offset, and can achieve very large linear range at low power consumption. The combination of the transconductor Gm 1212 and the current-driven loop filter 1216 realize boxcar sampling of the input signal Vin, which suppresses noise at harmonics of the sample rate.

The output of the current-input filter 1216 is digitized via ADC 1218, and the digital output 1220 is fed back into the forward path 1202 after being processed by an optional digital filter $H_2$ 1222, which can be used to further increase low-frequency loop gain. Switches SR1/SR4 1208 and SR2/SR3 1226 are closed during a reset phase to store the offset of the transconductor Gm 1212 on input capacitors $C_{AC}$ 1210, minimizing the chopper ripple due to transconductor offset. At the same time, all the capacitors in the loop filter are discharged by other switches. They are then left open for the remainder of each conversion so that sampled $KT/C_{AC}$ noise is converted into a much smaller chopper ripple. This enables using small values of $C_{AC}$. Since $Zin=1/(4 C_{AC} f_{CHOP})$, the use of small values of $C_{AC}$ enables higher input impedance than was previously possible.

FIG. 25 shows a second embodiment of the recorder circuitry 400B, wherein a continuous-time voltage-to-current converter and a switched capacitor, mixed-signal feedback path are used in conjunction. In recorder circuitry 400B, the feedback DAC 1224 is implemented with a charge redistribution structure comprising DAC capacitors $C_{DAC}$ 1228. As a result of the feedback and the use of the charge redistribution, the gain of the recorder circuitry 400B with the bandwidth of the feedback loop becomes $C_{AC}/(C_{DAC} V_{fsDAC})$, which is independent of the input signal, and can be made independent of temperature and manufacturing fluctuations. This enables precise gain matching and increased linear range compared to previously achievable values.

FIG. 26 is a circuit diagram illustrating a capacitive T-network 401 for use in recorder circuitry 400B, wherein capacitor $C_{DAC}$ 1228 of FIG. 25 is replaced by a capacitive T-network comprising a pair of $C_{DAC}$ capacitors 1274 and $(1/\alpha-2)$ $C_{DAC}$ capacitor 1276. The use of the capacitive T-network allows the realization of a smaller effective $C_{DAC}$ using large unit capacitors. As a result, the gain of the system can now be written as $C_{AC}/(C_{DAC} V_{REF})$. Flip-flop Q1 1272 re-aligns the feedback signal to the system clock to prevent glitches. Compared to the previous case shown in FIG. 25, for the same full-scale voltage and $C_{DAC}$ value, a smaller $C_{AC}$ value can be used, which results in even higher input impedance.

Figure 27:
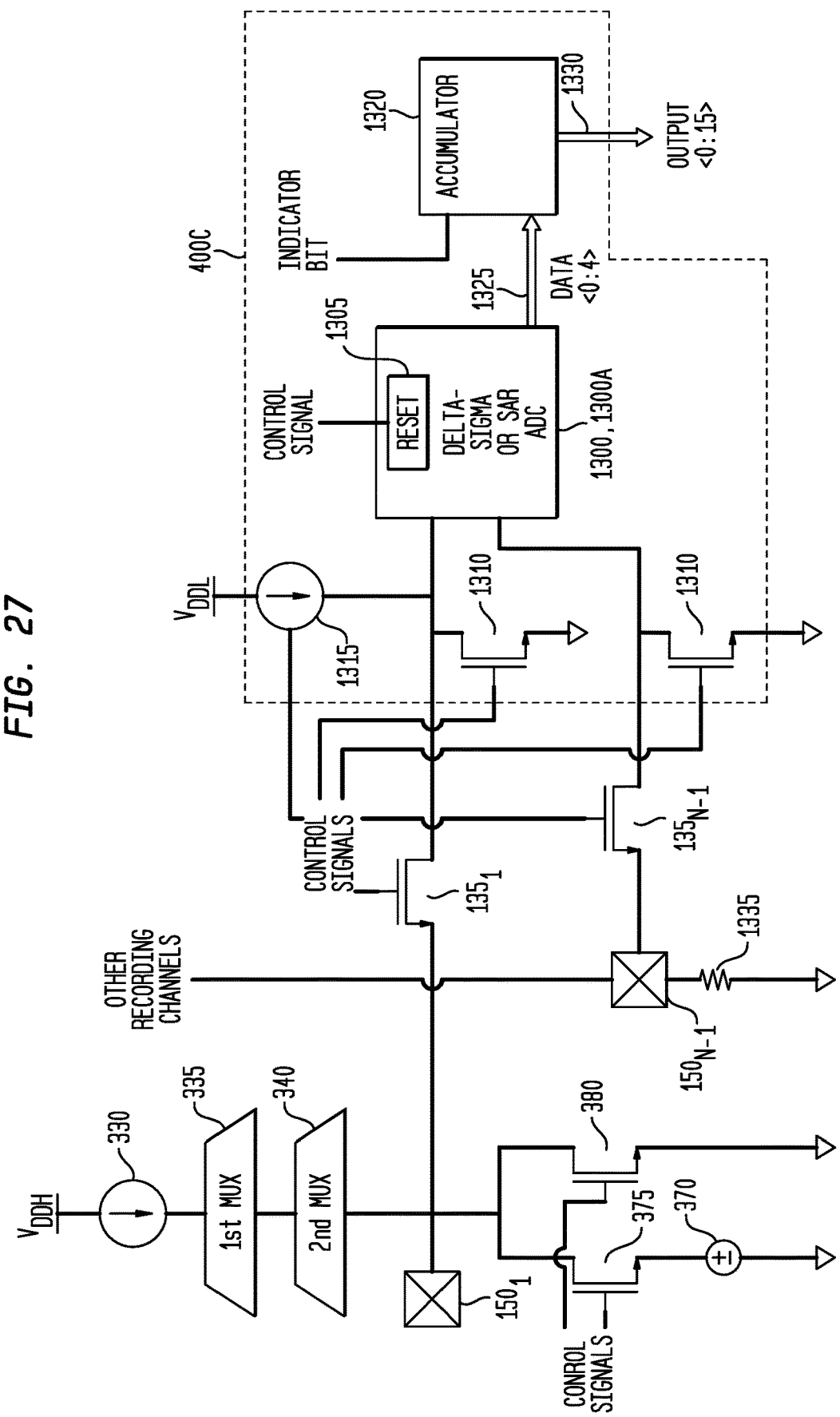
FIG. 27 is a circuit diagram illustrating the integration of the neural recording circuitry and stimulation circuitry.

FIG. 27 is a circuit diagram illustrating the integration of the neural recording circuitry 400 and stimulation circuitry 300. As mentioned above, the NMIC 100 also provides a tight coupling and significant integration between the stimulator circuitry 300 and the recorder circuitry 400, enabling simultaneous recording and stimulation, with a large dynamic range provided in recording to accommodate stimulation artifacts, along with integrated impedance measurements. In addition, the recorder circuitry 400 uses incremental, delta-sigma or SAR ADC 1300, 1300A recording to support concurrent stimulation, with a resettable interface for rapid recovery from saturation and greater stability, and compatibility with receiving a blocking signal from the stimulator controller 320. The recorder circuitry 400 is DC-coupled to provide charge monitoring at the electrode 150 interface, with different gain modes to accommodate larger artifacts from stimulation events, and with a digital output also indicating a stimulation event or an impedance measurement during a sample.

Referring to FIG. 27, only those salient aspects of recording circuitry 400C are illustrated which are directly relevant to simultaneous recording with stimulation. Those having skill in the art will recognize that any and all of the addition components illustrated in FIGS. 24-26 may also be utilized with recording circuitry 400C.

As illustrated in FIG. 27, control signals are provided, which generally are from the stimulation controller 320, such as control signals to blocking circuitry 135 (illustrated as FET transistors $135_1$ and $135_{N-1}$), but also may be from the serial digital interface and system monitor 155. As discussed above, during a stimulation event on a selected electrode, a control signal is provided to the corresponding blocking circuit 135, such as to turn off a switch or transistor 135 and prevent a comparatively high voltage on an electrode 150 from reaching the comparatively lower voltage recording circuitry 400C.

The reference electrode $150_{N-1}$ is coupled through a comparatively large resistance (resistor 1335) to ground, setting the DC potential to ground, and appearing as a comparatively high impedance to any stimulation current.

The reference electrode $150_{N-1}$ is coupled through a corresponding blocking circuit (e.g., switch or transistor) 135 to each recording circuit 400C, and during recording from a selected electrode 150, the reference electrode $150_{N-1}$ is not blocked from the corresponding recording circuit 400C. While a delta-sigma ADC 1300 or SAR ADC 1300A is utilized to provide recording from the corresponding electrode 150, in a differential mode, with voltages received from both the corresponding electrode 150 and the reference electrode $150_{N-1}$, those having skill in the art will recognize that any type of recording circuitry 400 may be utilized, any and all of which are considered equivalent and within the scope of the disclosure.

During recording on a selected electrode 150, any voltage on the selected electrode 150, as an analog voltage level, is compared to the voltage level on the reference electrode $150_{N-1}$ (e.g., as a voltage level indicative of baseline neural activity), by the delta-sigma ADC 1300 or SAR ADC 1300A, to provide a differential voltage level value which is also converted to a digital value and, output on bus 1325 (e.g., a 5 bit value <0:4>) (e.g., each voltage level is converted to a digital value, with the digital value from the reference electrode $150_{N-1}$ then subtracted from the digital value from the selected electrode 150, for example and without limitation). As a plurality of such samples are recorded (as a "delta"), they are provided to the accumulator 1320, which adds successive samples (as a "sigma" or Σ) and accumulates the result, providing time-averaged recording data which is output on bus 1330 (e.g., a 16 bit value <0:15> to the serial digital interface and system monitor 155 for transmission to the system controller and power supply 180). The time-averaged recording data also includes an indicator bit, appended to this output data, indicating whether the recorded data is from an impedance measurement on the selected electrode 150 or from a stimulation event on one or more other electrodes 150, providing for synchronization of recording with the timing of the stimulation events.

A control signal is also provided to the current source 1315, which is generally a comparatively small current source (μA, rather than mA), for an impedance measurement of the selected electrode 150. A small current is provided to charge the electrode 150 capacitance (as an RC circuit) providing a voltage on the electrode 150, followed by the differential recording by delta-sigma ADC 1300 or SAR ADC 1300A discussed above, generating multiple samples (e.g., 2-16 samples, as digital values, with the number of samples programmable as an input parameter). As the selected electrode is charged and the voltage increases (ramps up), the slope (rate of increase) of the sampled voltage levels provides a measure of the capacitance of the electrode), and the DC voltage level (as an IR drop) provides a measure of the resistance of the selected electrode 150.

Control signals are also provided to the switches 1310, which during blocking or during a reset, ground both of the inputs of the delta-sigma ADC 1300 or SAR ADC 1300A. A control signal is also provided to the delta-sigma ADC 1300 or SAR ADC 1300A, as a reset signal. For example, in the event of transient voltage from stimulation events occurring nearby to the selected electrode 150, saturation may occur, which is cleared by the reset, thereby allowing recording to resume promptly following any stimulation event.

As mentioned above, recording may occur on any of the electrodes $150_1$ through $150_{N-2}$, as separate channels, including simultaneous recording on selected electrodes 150 while stimulation events are occurring on other selected electrodes 150. A stimulation event on a given electrode 150, however, will typically generate voltages on the other electrodes 150 (as a "voltage artifact") in the vicinity of the given electrode 150, with these voltage artifact levels varying based upon the magnitude of the stimulation, the voltage drop across the given electrode 150, and the spatial location of the given electrode 150, with the other electrodes which are further away from the given electrode 150 generally receiving a comparatively smaller voltage artifact, and those electrodes spatially closer to the given electrode receiving a comparatively larger voltage artifact.

As the given electrodes 150 having a stimulation event is known in advance, and as comparatively large voltage artifacts would be expected for other nearby electrodes 150, blocking control signals are provided to these nearby electrodes 150. Similarly, for those electrodes 150 which will receive a comparatively less large voltage artifact, but enough to saturate various circuits as mentioned above, reset control signals are provided to the corresponding recording circuits 400C.

Not separately illustrated, the delta-sigma ADC 1300 (or SAR ADC 1300A) also includes different gain modes, for each channel, a high gain mode and a low gain mode. A low gain mode is used when there is some, comparatively low voltage artifact, e.g., +/−200 mV, on the selected electrode 150, while a high gain mode (providing a high dynamic range) is used when there is a comparatively small or negligible voltage artifact, e.g., +/−50 mV, on the selected electrode 150.

Figure 28A:
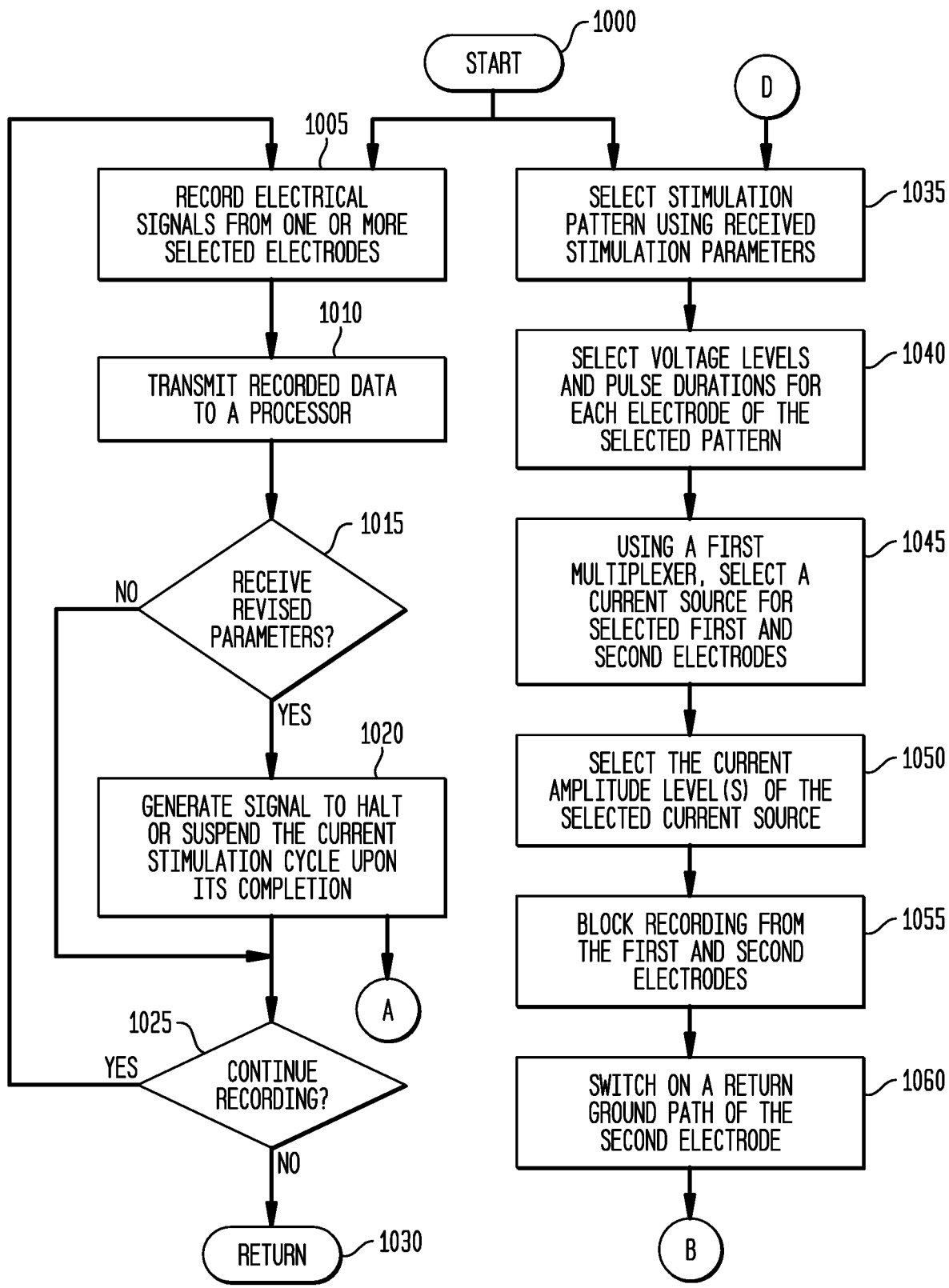
FIGS. 28A, 28B, and 28C (collectively referred to as "FIG. 28") are a flow chart illustrating a representative stimulation and recordation method embodiment.
Figure 28B:
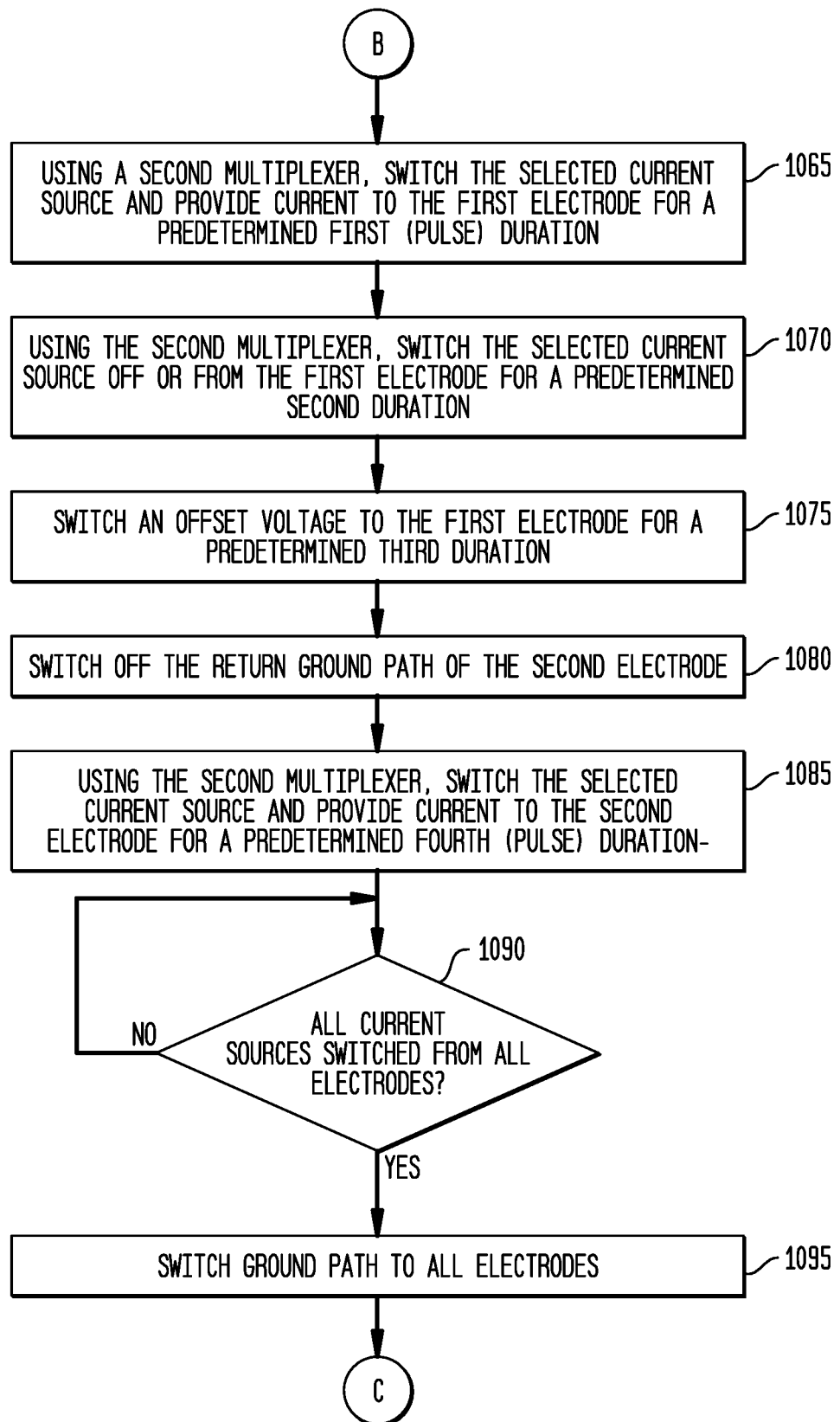
Figure 28C:
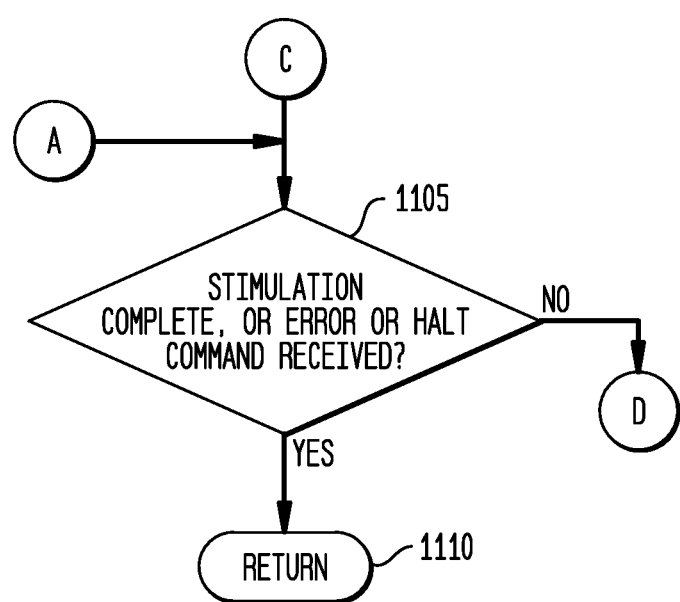

FIG. 28 is a flow chart illustrating a representative stimulation method with concurrent recording embodiment, and provides a useful summary, for biphasic and bipolar stimulation, of the various types of stimulation which may be provided. Those having skill in the art will recognize that not all of these steps will be performed for other types of stimulation and may be omitted, such as for monopolar and/or monophasic stimulation, in any combination. As discussed above, the representative apparatus, system and method provide simultaneous stimulation and recording using different electrodes 150 of the electrode array. The method begins, start step 1000, with the recordation of electrical signals from one or more selected electrodes, step 1005, using recorder circuitry 400. The recorded data is transmitted to a processor, such as a processor within the system controller and power supply 180, using the serial interface 905 and the transceiver 930, step 1010. When revised parameters have been received, step 1015, such as from the system controller and power supply 180 in response to the transmitted data, a control signal is generated to halt or suspend the current stimulation cycle upon its completion, step 1020. When no revised parameters have been received in step 1015, and following step 1020, and when recording is to be continued, step 1025, the method iterates and returns to step 1005, and otherwise the recording may end, return step 1030.

Concurrently with the recordation of steps 1005-1025 (but using electrodes 150 which are not being used for concurrent recordation), also beginning with start step 1000, the stimulation methodology begins with the selection (by the stimulation controller 320) of a stimulation pattern, step 1035, typically using the received stimulation parameters stored in the memory 305. The voltage levels and pulse durations are selected for each electrode 150 of the selected stimulation pattern, step 1040, also typically by the stimulation controller 320, using the first programmable power converter 120 to select $V_{DD}$, DAC 425, and memory 305, and typically based upon received stimulation parameters stored in the memory 305 which, in turn, were based upon recorded measurements (e.g., impedance) transmitted to the system controller and power supply 180.

Using a first multiplexer 335, a current source 330 is selected for selected first and second electrodes 150, step 1045, also using control signals from the stimulation controller 320. As mentioned above, for unipolar stimulation, a counter electrode $150_N$ may be selected as the first electrode. The stimulation controller 320 also selects the current amplitude levels for the selected current source 330 for the selected first and second electrodes 150, step 1050, using DAC 425 and received stimulation parameters stored in the memory 305. Recording is blocked from the selected first and second electrodes 150, step 1055, using blocking circuits 135 and also using control signals from the stimulation controller 320. Also as part of step 1055, as discussed above, recording may be blocked from other electrodes 150 (which would have voltage artifacts expected to be comparatively high), and reset control signals may also be provided to recording circuits 400C (which would have voltage artifacts expected to be saturating), while recording is allowed on other electrodes 150, in a high or low gain mode. A return ground path is switched on for the second electrode 150, step 1060, using a switch 380 and also using control signals from the stimulation controller 320.

Using a second multiplexer 340, and using control signals from the stimulation controller 320, the selected current source 330 is switched to provide current to the first electrode 150 for a predetermined first (pulse) duration, step 1065, such as illustrated in FIG. 11 for the $\phi_{1A}$ interval. Following the predetermined first (pulse) duration, and using the second multiplexer 340 and control signals from the stimulation controller 320, the selected current source 330 is switched off or from the first electrode 150 for a predetermined second duration, step 1070, such as illustrated in FIG. 11 for the $\phi_{1B}$ interval. An offset voltage is switched on for the first electrode 150 for a predetermined third duration, step 1075, using a switch 375 and an offset voltage generator 370, and also using control signals from the stimulation controller 320, such as illustrated in FIG. 11 for the $\phi_{2A}$ interval. The return ground path is also switched off for the second electrode 150, step 1080, using a switch 380 and also using control signals from the stimulation controller 320. As mentioned above, for bipolar and monophasic stimulation, as no stimulation is provided to a second electrode $150_2$, no voltage offset is provided to the first electrode 150$_1$, and instead grounding continues on the second electrode 150$_2$, as mentioned above.

Using the second multiplexer 340, and using control signals from the stimulation controller 320, the selected current source 330 is switched to provide current to the second electrode 150 for a predetermined fourth (pulse) duration, step 1085, such as illustrated in FIG. 11 for the $\phi_{2B}$ interval. This step is omitted for monophasic stimulation. When all the current sources 330 for the selected stimulation pattern have been switched off, step 1090, a return ground path is switched on for all of the selected electrodes 150 of the stimulation pattern, step 1095, using switches 380 and also using control signals from the stimulation controller 320, ending the current stimulation cycle. When stimulation is complete, or when an error or halt command has been received (e.g., from step 1020), the stimulation part of the method may end, return step 1110, and otherwise the simultaneous stimulation and recording continues, returning to step 1035 (and to step 1005, following step 1025).

It should be noted that steps 1035-1105 are implemented for every pair of electrodes involved in a biphasic and bipolar stimulation. Those having skill in the art will recognize that not all of these steps will be performed for other types of stimulation and may be omitted, such as for monopolar and/or monophasic stimulation, in any combination, and as discussed above. Those having skill in the art will also recognize that the stimulation methodology illustrated in FIG. 28 may be readily modified for these other types of stimulation using the control and timing diagrams as illustrated in FIGS. 16-18, in which no stimulation is provided to a second electrode 150, or a counter electrode 150$_N$ is utilized, or no voltage offset is provided to the first electrode 150 as no second phase of stimulation is provided to a second electrode 150, and grounding is provided instead to the second electrode 150. For example, for unipolar and monophasic stimulation as discussed above, a counter electrode 150$_N$ is utilized instead of another type of electrode 150, and further that no stimulation is provided to a second electrode 150$_2$, no voltage offset is provided to the first electrode 150$_1$ (or counter electrode 150$_N$ in this case), and instead grounding continues on the second electrode 150$_2$, as mentioned above.

Figure 29:
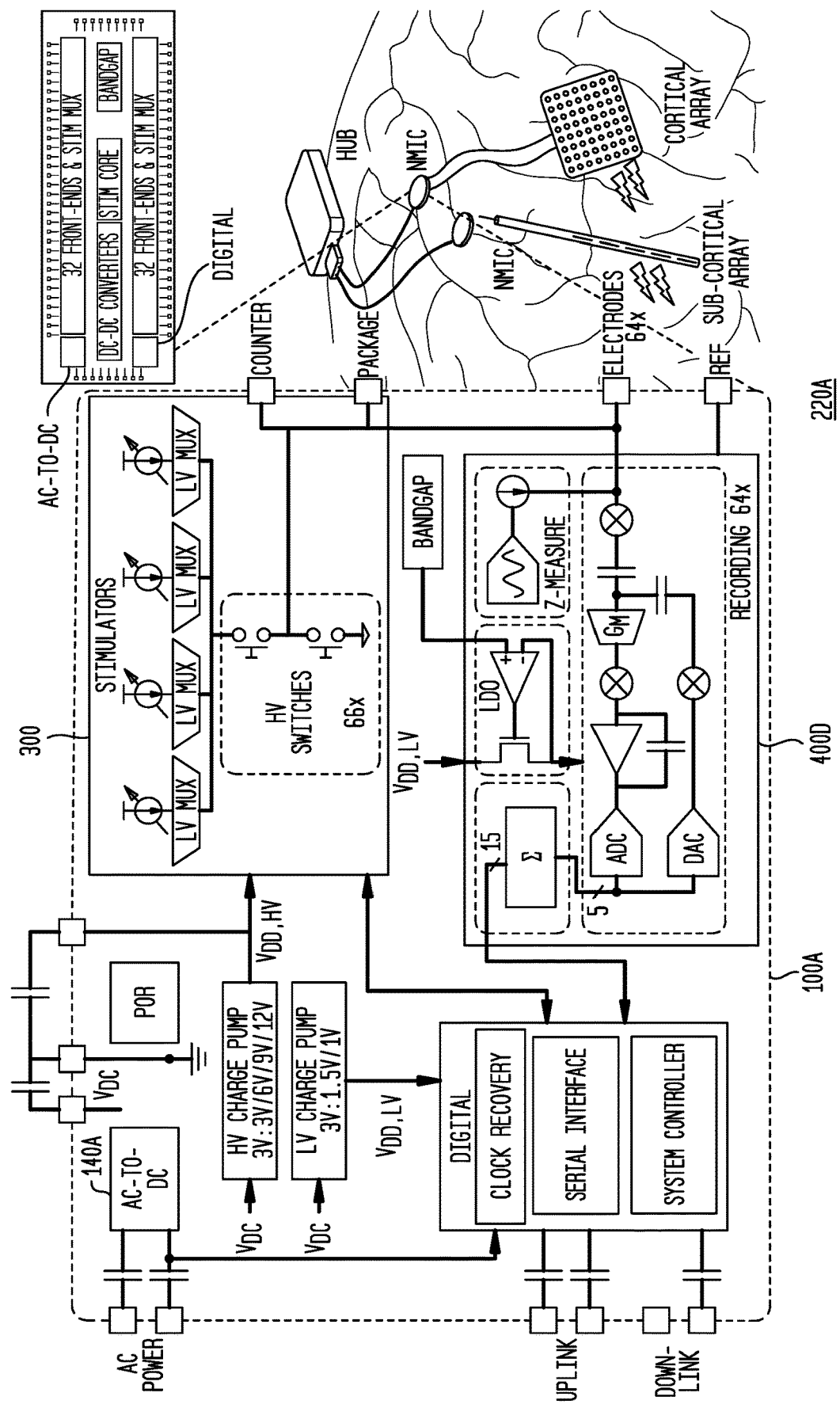
FIG. 29 is a block diagram illustrating a second representative neuromodulator integrated circuit apparatus embodiment and a representative sixth system embodiment.
Figure 31A:
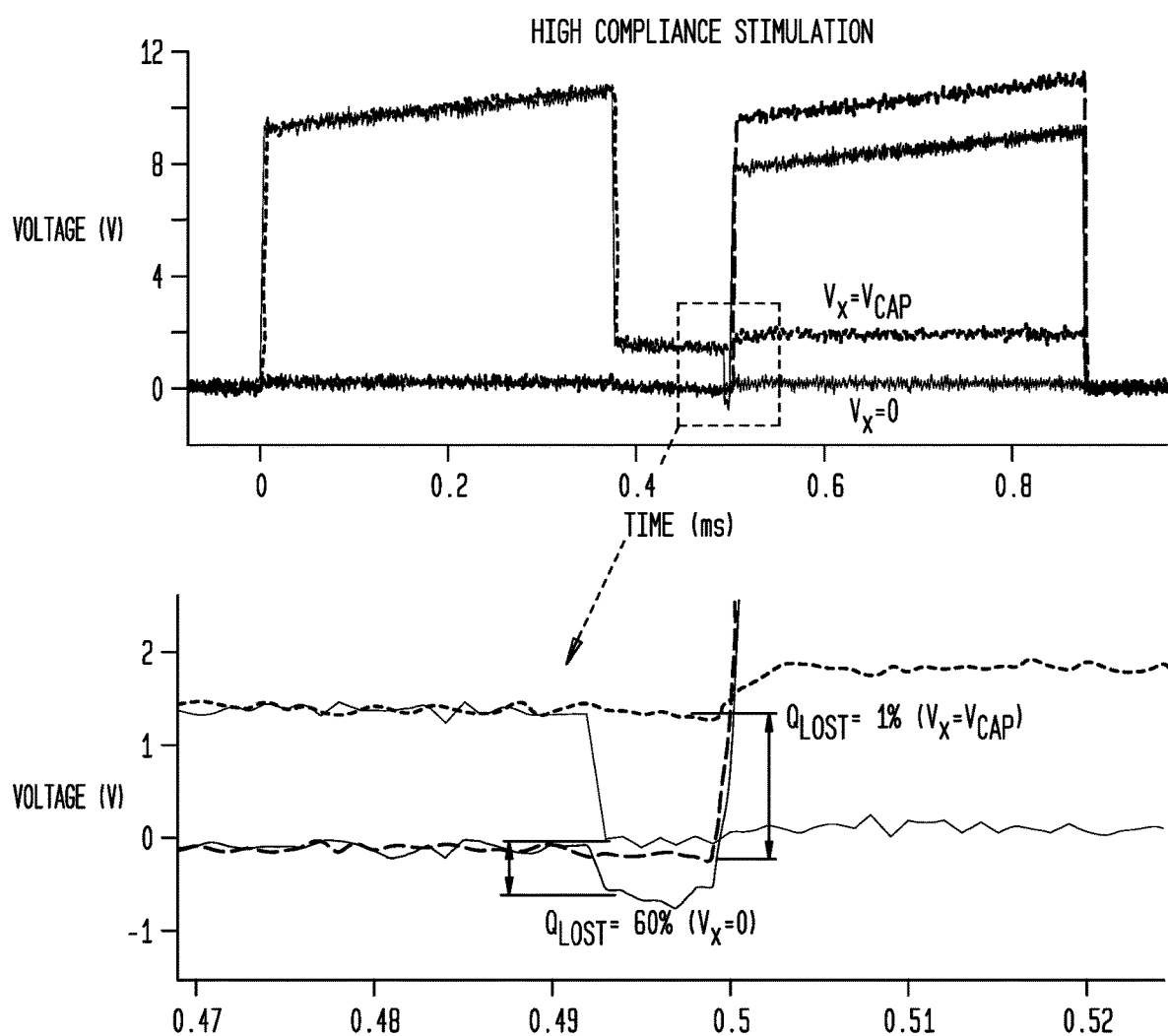
FIGS. 31A and 31B (collectively FIG. 31) are graphical diagrams illustrating stimulation waveforms and demonstrating rapid reconfiguration of arbitrary stimulation waveforms and high compliance stimulation.
Figure 31B:
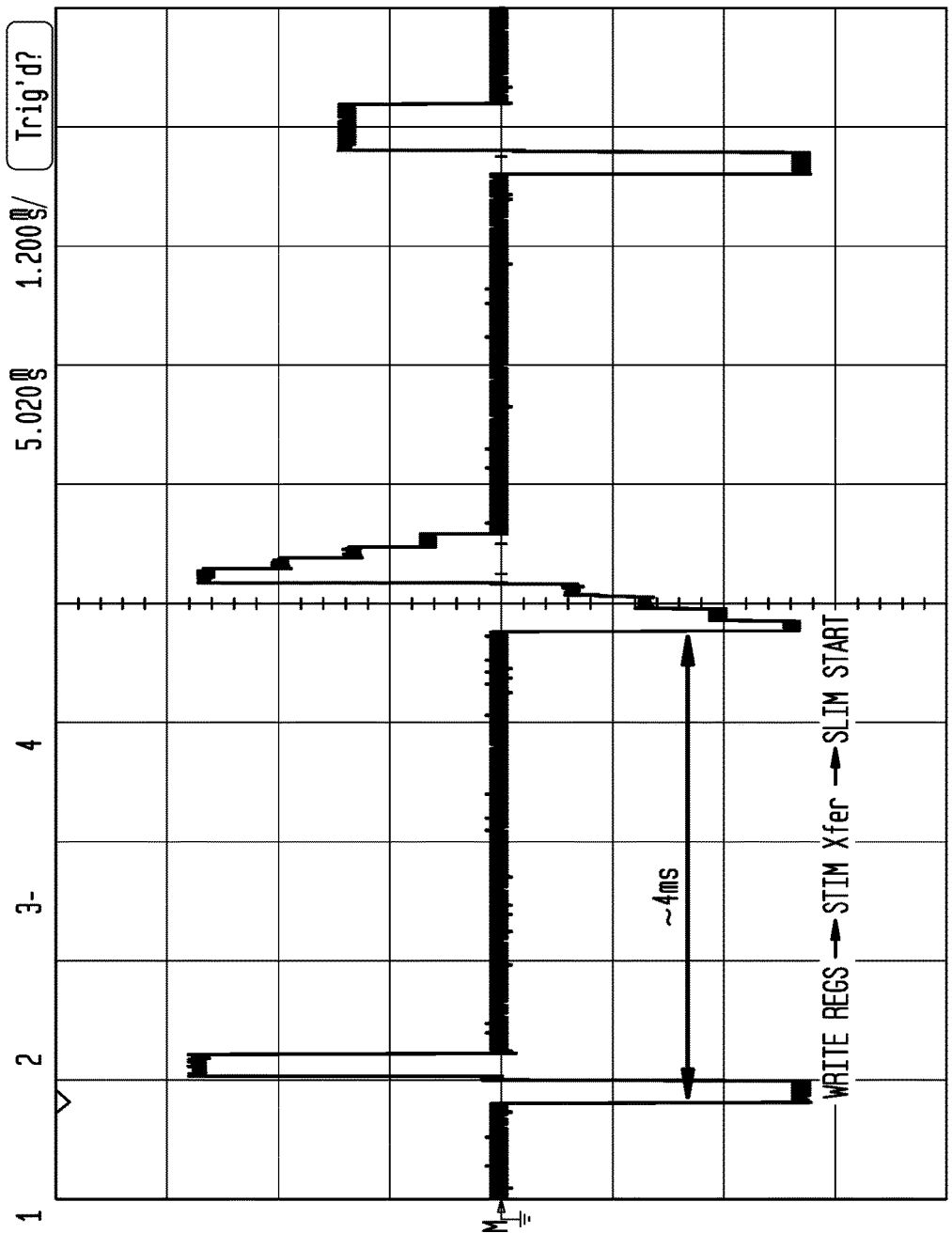
Figure 32:
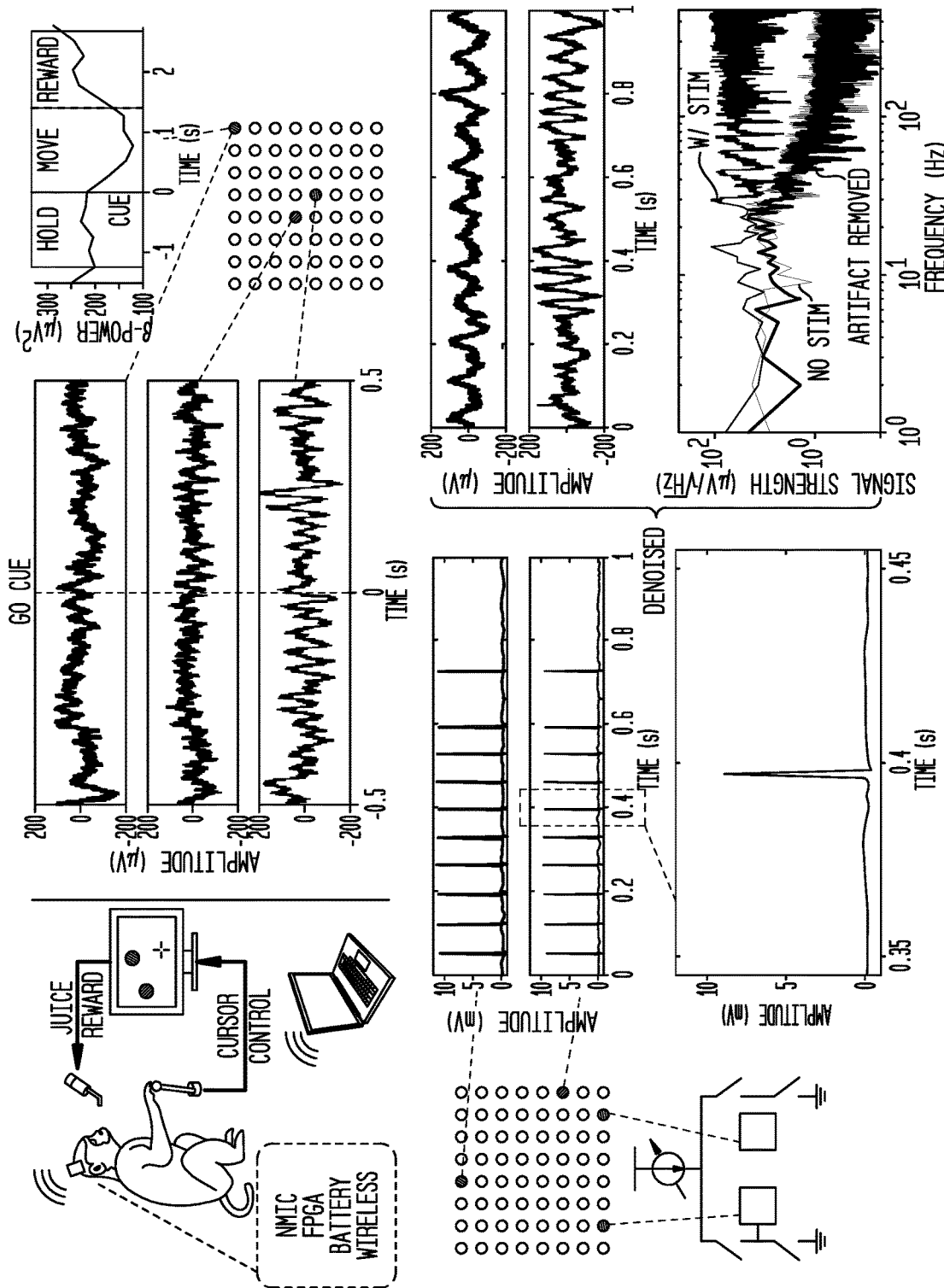
FIG. 32 are illustrations of experimental setup and graphical diagrams illustrating spectrum recovery from about an 8 mV stimulation artifact.

FIG. 29 is a block diagram illustrating a second representative neuromodulator integrated circuit apparatus 100A embodiment and a representative sixth system embodiment 220A. FIG. 30 is a block diagram illustrating representative recording circuitry 400D of a second representative neuromodulator integrated circuit apparatus embodiment 100A and measurements, with the noise spectrum being input-referred and SFDR spectrum normalized to full scale input. FIG. 31 are graphical diagrams illustrating stimulation waveforms and demonstrating rapid reconfiguration of arbitrary stimulation waveforms and high compliance stimulation. FIG. 32 are illustrations of experimental setup and graphical diagrams illustrating spectrum recovery from about an 8 mV stimulation artifact. All in vivo experiments were performed in compliance with the NIH Guide for the Care and Use of Laboratory Animals. FIG. 33 is a table illustrating comparative results, comparing the NMIC 100A with [3] H. Rhew, IEEE JSSC, October 2014; [4] R. Shulyzki, IEEE TBioCAS, February 2015; and [5] Y. Lo, IEEE ISSCC 2016.

Referring to FIGS. 29-33, providing a useful summary and also introducing additional variations, the neuromodulation IC (NMIC) 100A shown in FIG. 29 enables simultaneous 64-channel neural recording and stimulation, and meets all the requirements described above. The NMIC 100A features 64 low-noise and high dynamic range neural recording front-ends and 4 high-compliance stimulators with rapidly reconfigurable locations (any of 64 electrodes 150), amplitudes, pulse timing, and frequencies. Stimulation and recording hardware are reused to perform impedance measurement on all electrodes 150. It incorporates a 6-wire power and data transfer architecture, simplifying cabling, as mentioned above. A 2 Mbps bidirectional data interface enables constant recording, rapid reprogramming, and system monitoring to ensure safe operation. Power and clock are derived from a 20 MHz, 3 VAC input voltage and rectified to a 3 VDC supply voltage, or supplied from a 3V battery. Programmable DC-DC converters with >80% measured power efficiency provide a 1V supply to the recording and digital subsystems as well as a 3/6/9/12V supply to the stimulator, adjusting the compliance for different stimulation regimes to increase efficiency.

Recording and stimulation compatibility is achieved through common referencing at ground, charge balancing of the stimulation, and a front-end with rapid overload recovery and a large linear input range. The recording subsystem 400D (FIG. 30) is comprised of 64 mixed-signal 1 kS/s 15-bit front-ends. Each front-end has a separate LDO to minimize power supply coupling. The front-ends have a programmable full-scale input voltage ($V_{fsDAC}$) of 50 mV-±200 mV allowing simultaneous amplification and digitization of the electrode offset, neural signal, and stimulation artifact within the linear range. A higher linear input range than state of the art is achieved by bringing the ADC 1300A inside the capacitive feedback loop 1305, reducing the needed signal swing at internal nodes. Low noise is achieved through chopper-stabilization (1206, 1214) of the Gm stage 1212 and a current-input loop filter that suppresses noise at harmonics of the sample rate. A 5-bit, 1024×-oversampled SAR ADC 1300A results in a 15-bit output and a charge-redistribution DAC 1312 provides feedback at the Gm 1212 input, creating a virtual ground. The front-end gain is $C_{AC}/(C_{DAC}V_{fsDAC})$, independent of temperature and manufacturing variations. $S_{RST}$ switches (1226) are closed during a brief reset phase to store the offset of the Gm on $C_{AC}$, minimizing chopper ripple and aiding in rapid recovery by clearing the memory of the previous sample. The sampled kT/$C_{AC}$ noise is converted into out-of-band chopper ripple, enabling small values of $C_{AC}$ and high input impedance since $Z_{in}=1/(4C_{AC}f_{CHOP})$. The measured front-end linear input range is about 100× greater than state-of-the-art with a 55 dB higher dynamic range, a lower THD, a 1.8× lower VDD, and lowest PEF.

The precise current matching between phases accommodates both the high peak currents of the stimulators and the need for rapid artifact recovery. The stimulator architecture discussed above reuses the same current source for the cathodic and anodic stimulation phases to minimize charge error. This implementation does not require the stimulator electrodes to be referenced at a large $V_{REF}$ or $V_{DD}$, making it easier to combine with low-voltage recording circuits. To maximize compliance and compatibility with recording, a ground-referenced architecture is utilized. The need for a negative supply is eliminated by adding a DC offset generated by an adjustable diode string ($V_X$) in the second phase to prevent a negative voltage at the beginning of the anodic phase resulting in a measured 0.016% mismatch for low compliance, and <1% mismatch for high compliance stimulation. A programmable passive recharge phase further reduces residual charge and DC offsets on the electrodes. The stimulator can produce monophasic, biphasic, and other arbitrary waveforms, can store patterns and be reprogrammed up to every 4 ms for closed-loop applications. Multiple stimulators can be combined on a single electrode to produce complex waveforms (FIG. 31) or high currents up to 20 mA.

The NMIC 100A was assembled with a Pt—Ir and W electrode microdrive and implanted in the motor cortex of an adult macaque monkey (FIG. 32). Recordings were taken during a motor task with a juice reward upon task completion. Readout on all channels was performed and shows β-band (13-30 Hz) power decrease during movement and increase during a hold period and reward, consistent with neuroscientific results. Simultaneous biphasic stimulation (15 Hz, 150 µA) and recording in the motor cortex resulted in a 1 ms (single-sample) stimulation artifact. Multi-channel PCA denoising was used to remove the stimulation artifact and recover the underlying biological signal spectrum. All in vivo experiments were performed in compliance with the NIH Guide for the Care and Use of Laboratory Animals.

The NMIC 100A was fabricated in an 180 nm 1P6M HV CMOS process and occupies 11.52 mm$^2$. The total power dissipation of the chip is stimulation protocol dependent, and is 700 µW in typical configuration, including power management circuits. We compared against recently published bidirectional neural interface ICs in the table of FIG. 33. The NMIC integrates the highest degree of stimulator programmability and highest peak current with the highest dynamic range recording, while achieving state-of-the-art noise and power performance. Co-design of the recording and stimulation subsystems enables saturation-free recording during stimulation with a 1 ms (single sample) artifact, and with the potential to enable true closed-loop neuromodulation.

As used herein, a "controller" 320, 900 or "processor" may be any type of controller or processor, and may be embodied as one or more controller(s) 320, 900 (or processor(s)), configured, designed, programmed or otherwise adapted to perform the functionality discussed herein. As the term controller or processor is used herein, a controller 320, 900 or processor may include use of a single integrated circuit ("IC"), or may include use of a plurality of integrated circuits or other components connected, arranged or grouped together, such as controllers, microprocessors, digital signal processors ("DSPs"), array processors, graphics or image processors, parallel processors, multiple core processors, custom ICs, application specific integrated circuits ("ASICs"), field programmable gate arrays ("FPGAs"), adaptive computing ICs, associated memory (such as RAM, DRAM and ROM), and other ICs and components, whether analog or digital. As a consequence, as used herein, the term processor (or controller) should be understood to equivalently mean and include a single IC, or arrangement of custom ICs, ASICs, processors, microprocessors, controllers, FPGAs, adaptive computing ICs, or some other grouping of integrated circuits which perform the functions discussed below, with associated memory, such as microprocessor memory or additional RAM, DRAM, SDRAM, SRAM, MRAM, ROM, FLASH, EPROM or E$^2$PROM. A controller 320, 900 or processor, with associated memory, may be adapted or configured (via programming, FPGA interconnection, or hard-wiring) to perform the methodology of the invention, as discussed herein. For example, the methodology may be programmed and stored, in a controller 320, 900 or processor with its associated memory (and/or memory 305) and other equivalent components, as a set of program instructions or other code (or equivalent configuration or other program) for subsequent execution when the processor or controller is operative (i.e., powered on and functioning). Equivalently, when the controller 320, 900 or processor may implemented in whole or part as FPGAs, custom ICs and/or ASICs, the FPGAs, custom ICs or ASICs also may be designed, configured and/or hard-wired to implement the methodology of the invention. For example, the controller 320, 900 or processor may be implemented as an arrangement of analog and/or digital circuits, controllers, microprocessors, DSPs and/or ASICs, collectively referred to as a "processor" or "controller", which are respectively hard-wired, programmed, designed, adapted or configured to implement the methodology of the invention, including possibly in conjunction with a memory 305.

The memory 305, which may include a data repository (or database), may be embodied in any number of forms, including within any computer or other machine-readable data storage medium, memory device or other storage or communication device for storage or communication of information, currently known or which becomes available in the future, including, but not limited to, a memory integrated circuit ("IC"), or memory portion of an integrated circuit (such as the resident memory within a controller 320 or processor), whether volatile or non-volatile, whether removable or non-removable, including without limitation RAM, FLASH, DRAM, SDRAM, SRAM, MRAM, FeRAM, ROM, EPROM or E$^2$PROM, or any other form of memory device or other machine-readable storage or memory media, or any other type of memory, storage medium, or data storage apparatus or circuit, which is known or which becomes known, depending upon the selected embodiment. The memory 305 may be adapted to store various look up tables, parameters, coefficients, other information and data, programs or instructions (of the software of the present invention), and other types of tables such as database tables.

As indicated above, the controller 320, 900 or processor is hard-wired or programmed, using software and data structures of the invention, for example, to perform the methodology of the present invention. As a consequence, the system and method of the present invention may be embodied as software which provides such programming or other instructions, such as a set of instructions and/or metadata embodied within a non-transitory computer readable medium, discussed above. In addition, metadata may also be utilized to define the various data structures of a look up table or a database. Such software may be in the form of source or object code, by way of example and without limitation. Source code further may be compiled into some form of instructions or object code (including assembly language instructions or configuration information). The software, source code or metadata of the present invention may be embodied as any type of code, such as C, C++, Matlab, SystemC, LISA, XML, Java, Brew, SQL and its variations (e.g., SQL 99 or proprietary versions of SQL), DB2, Oracle, or any other type of programming language which performs the functionality discussed herein, including various hardware definition or hardware modeling languages (e.g., Verilog, VHDL, RTL) and resulting database files (e.g., GDSII). As a consequence, a "construct", "program construct", "software construct" or "software", as used equivalently herein, means and refers to any programming language, of any kind, with any syntax or signatures, which provides or can be interpreted to provide the associated functionality or methodology specified (when instantiated or loaded into a processor or computer and executed, including the controller 320 or processor, for example).

The software, metadata, or other source code of the present invention and any resulting bit file (object code, database, or look up table) may be embodied within any tangible, non-transitory storage medium, such as any of the computer or other machine-readable data storage media, as computer-readable instructions, data structures, program modules or other data, such as discussed above with respect to the memory 305, or any other type of data storage apparatus or medium, as mentioned above.

The serial digital interface circuit(s) (905) are utilized for appropriate connection to a relevant channel, network or bus; for example, the serial digital interface circuit(s) (905) may provide impedance matching, drivers and other functions for a wireline interface, may provide demodulation and analog to digital conversion for a wireless interface, and may provide a physical interface for the controller 320, 900 or processor and/or memory 305 with other devices. In general, the serial digital interface circuit(s) (905) are used to receive and transmit data, depending upon the selected embodiment, such as program instructions, parameters, configuration information, control messages, data and other pertinent information.

Numerous advantages of the representative embodiments are readily apparent. The representative apparatus, method and/or system embodiments not only provide electrical sensing to record various electrical patterns (such as cortical signals) in real time, but also provide concurrent or nearly concurrent stimulation to selected areas in response to these sensed signals and further based upon selected stimulation programs, along with the amount and type of stimulation, determined by medical and other clinical professionals, enabling closed-looped feedback in a singular device and/or system. The representative apparatus, system and method provide for comparatively rapid feedback, to provide increased control in real-time over stimulation and changes in stimulation based upon the recorded data of changing patient or subject conditions, such as real-time neural electrical stimulation immediately following data acquisition from real-time neural electrical recording. In addition, representative apparatus, system and method embodiments enable rapid configuration and reconfiguration of stimulation waveforms.

Additional features and advantages of the representative apparatus, system and method are also apparent. For example, the representative apparatus, system and method are compatible with multiple types of electrodes, a variable number of electrodes, and electrodes in multiple different locations, further enabling a plurality of different spatial patterns of stimulation, each of which may have a different amount, type and pattern of stimulation. For example and without limitation, the representative apparatus, system and method may detect and record a cortical electrical pattern indicative of a likelihood of seizure activity, transmit this information for data processing, receive corresponding commands and stimulation parameters, and in response, generate corresponding cortical stimulations which prevent an otherwise ensuing seizure in an individual.

The representative apparatus and system are also modular and distributed, providing communication through a central hub (or router) which enable stimulation and recording in multiple, different and distributed locations throughout the body of a subject individual, while enabling centralized control over such stimulation. The representative apparatus and system are also scalable, capable of adding (or removing) modules (such as neuromodulation integrated circuits) within the same system. The representative apparatus, system and method embodiments further provide for digital communication between and among the various components, enabling a significant number of communication channels with error correction and various other monitoring and safety protocols.

The representative apparatus, system and method embodiments also enable significant flexibility in stimulation. For example, representative embodiments provide for a wide variety of available voltage levels, e.g., ranging from 1 V to 12 V, enabling selection of and combining or mixing of comparatively high-voltage (HV) and low-voltage (LV) devices for stimulation of selected electrodes using a plurality of current sources coupled to the selected voltage level. An adaptive voltage supply also enables power conservation and provides additional voltage headroom. An AC-coupled interface further enables implantable operation.

Other notable advantages include the generation of an offset voltage during a second phase of a biphasic stimulation, eliminating comparatively large negative voltages from charge transfer, and further improving the matching between phases.

The present disclosure is to be considered as an exemplification of the principles of the invention and is not intended to limit the invention to the specific embodiments illustrated. In this respect, it is to be understood that the invention is not limited in its application to the details of construction and to the arrangements of components set forth above and below, illustrated in the drawings, or as described in the examples. Systems, methods and apparatuses consistent with the present invention are capable of other embodiments and of being practiced and carried out in various ways.

Although the invention has been described with respect to specific embodiments thereof, these embodiments are merely illustrative and not restrictive of the invention. In the description herein, numerous specific details are provided, such as examples of electronic components, electronic and structural connections, materials, and structural variations, to provide a thorough understanding of embodiments of the present invention. One skilled in the relevant art will recognize, however, that an embodiment of the invention can be practiced without one or more of the specific details, or with other apparatus, systems, assemblies, components, materials, parts, etc. In other instances, well-known structures, materials, or operations are not specifically shown or described in detail to avoid obscuring aspects of embodiments of the present invention. In addition, the various Figures are not drawn to scale and should not be regarded as limiting.

Reference throughout this specification to "one embodiment", "an embodiment", or a specific "embodiment" means that a particular feature, structure, or characteristic described in connection with the embodiment is included in at least one embodiment of the present invention and not necessarily in all embodiments, and further, are not necessarily referring to the same embodiment. Furthermore, the particular features, structures, or characteristics of any specific embodiment of the present invention may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention.

It will also be appreciated that one or more of the elements depicted in the Figures can also be implemented in a more separate or integrated manner, or even removed or rendered inoperable in certain cases, as may be useful in accordance with a particular application. Integrally formed combinations of components are also within the scope of the invention, particularly for embodiments in which a separation or combination of discrete components is unclear or indiscernible. In addition, use of the term "coupled" herein, including in its various forms such as "coupling" or "coupleable", means and includes any direct or indirect electrical, structural or magnetic coupling, connection or attachment, or adaptation or capability for such a direct or indirect electrical, structural or magnetic coupling, connection or attachment, including integrally formed components and components which are coupled via or through another component.

With respect to signals, we refer herein to parameters that "represent" a given metric or are "representative" of a given metric, where a metric is a measure of a state of at least part of the regulator or its inputs or outputs. A parameter is considered to represent a metric if it is related to the metric directly enough that regulating the parameter will satisfactorily regulate the metric. A parameter may be considered to be an acceptable representation of a metric if it represents a multiple or fraction of the metric.

Furthermore, any signal arrows in the drawings/Figures should be considered only exemplary, and not limiting, unless otherwise specifically noted. Combinations of components of steps will also be considered within the scope of the present invention, particularly where the ability to separate or combine is unclear or foreseeable. The disjunctive term "or", as used herein and throughout the claims that follow, is generally intended to mean "and/or", having both conjunctive and disjunctive meanings (and is not confined to an "exclusive or" meaning), unless otherwise indicated. As used in the description herein and throughout the claims that follow, "a", "an", and "the" include plural references unless the context clearly dictates otherwise. Also as used in the description herein and throughout the claims that follow, the meaning of "in" includes "in" and "on" unless the context clearly dictates otherwise.

The foregoing description of illustrated embodiments of the present invention, including what is described in the summary or in the abstract, is not intended to be exhaustive or to limit the invention to the precise forms disclosed herein. From the foregoing, it will be observed that numerous variations, modifications and substitutions are intended and may be effected without departing from the spirit and scope of the novel concept of the invention. It is to be understood that no limitation with respect to the specific methods and apparatus illustrated herein is intended or should be inferred. It is, of course, intended to cover by the appended claims all such modifications as fall within the scope of the claims.

It is claimed:

1. A system for electrical stimulation and electrical recording in human or non-human subject, the system comprising:
   one or more implantable electrode arrays;
   a first system controller configured to provide a plurality of stimulation parameters and a plurality of commands in response to received recorded data; and
   one or more implantable apparatuses electromagnetically or wirelessly coupleable to the first system controller, each implantable apparatus coupled to a corresponding implantable electrode array comprising a plurality of electrodes, each implantable apparatus comprising:
   a plurality of stimulation circuits selectively coupleable to the plurality of electrodes, each stimulation circuit configured, in response to a control signal of a first plurality of control signals, to provide a stimulation current on a selected electrode of the plurality of electrodes, each stimulation circuit comprising: a variable current source configured to generate a selectable, variable current to provide the stimulation current on the selected electrode; a first multiplexer coupled to each variable current source, the first multiplexer comprising a first plurality of switches; and a second multiplexer coupled to the first multiplexer, the second multiplexer comprising a second plurality of switches, each switch of the second multiplexer coupleable to a corresponding electrode of the plurality of electrodes;
   a plurality of recording circuits, one or more recording circuits of the plurality of recording circuits configured to generate corresponding recorded data concurrently with the stimulation current;
   a transceiver circuit coupled to the plurality of stimulation circuits and to the plurality of recording circuits, the transceiver circuit configured to transmit the corresponding recorded data to the first system controller and to receive the plurality of stimulation parameters and the plurality of commands from the first system controller for closed-loop feedback; and
   a plurality of blocking circuits, each blocking circuit coupled to a corresponding recording circuit of the plurality of recording circuits and further coupleable to a corresponding electrode of the plurality of electrodes, each blocking circuit configured, in response to a corresponding control signal of a second plurality of control signals, to block the stimulation current on the selected electrode from the corresponding recording circuit.

2. The system of claim 1, wherein each recording circuit further comprises:
   a reset circuit configured, in response to a corresponding control signal of a third plurality of control signals, to provide a ground potential to an input of the corresponding recording circuit.

3. The system of claim 1, wherein when a stimulation circuit is providing a stimulation current to one or more selected electrodes of a first plurality of electrodes of a selected electrode array of the one or more implantable electrode arrays, each recording circuit is coupled to a corresponding electrode of a second plurality of electrodes of the selected electrode array to concurrently generate the corresponding recorded data, wherein the second plurality of electrodes is different from the first plurality of electrodes.

4. The system of claim 1, wherein each recording circuit comprises:
   an amplifier; and
   an analog-to-digital converter having a digitally-controlled reset circuit.

5. The system of claim 4, wherein when a stimulation circuit is providing a stimulation current to one or more selected electrodes of a first plurality of electrodes, each amplifier and analog-to-digital converter of each recording circuit is configured to simultaneously receive a first voltage level from a corresponding electrode of a second plurality of electrodes of the electrode array and receive a second voltage level from a reference electrode of the electrode array, and to convert a difference of the first and second voltage levels to digital, differential voltage data, wherein the second plurality of electrodes is different from the first plurality of electrodes.

6. The system of claim 5, further comprising:
an accumulator coupled to the analog-to-digital converter, the accumulator configured to accumulate a plurality of samples of the differential digital voltage data, and to output the accumulated differential digital voltage data as the corresponding recorded data, the corresponding recorded data further having an indicator bit indicating whether the corresponding recorded data is from a stimulation event or not from a stimulation event.

7. The system of claim 5, wherein each recording circuit further comprises:
a current source coupled to the corresponding electrode of the plurality of electrodes, the current source configured to provide a current to the corresponding electrode to generate the first voltage level for an impedance measurement.

8. The system of claim 1, wherein each stimulation circuit further comprises:
a switchable voltage offset circuit coupleable to the corresponding electrode of the plurality of electrodes; and
a switchable grounding circuit coupleable to the corresponding electrode of the plurality of electrodes.

9. The system of claim 1, wherein each stimulation circuit further comprises:
a stimulation controller configured to generate the first and second pluralities of control signals to implement at least one type of stimulation selected from the group consisting of: bipolar and biphasic, bipolar and monophasic, unipolar and biphasic, unipolar and monophasic, and combinations thereof; and
an H bridge circuit configured to control the direction of current flow between a plurality of electrodes to facilitate at least one type of stimulation using a single current source or plurality of current sources.

10. The system of claim 1, wherein each stimulation circuit further comprises:
a memory circuit configured to store one or more stimulation parameters of the plurality of stimulation parameters, wherein the plurality of stimulation parameters comprise one or more parameters selected from the group consisting of: a pulse amplitude, a pulse duration, a pulse sequence, one or more selected electrodes, a stimulation pattern, and combinations thereof.

11. The system of claim 10, wherein each stimulation circuit further comprises:
a stimulation controller configured to determine a validity of the plurality of stimulation parameters.

12. The system of claim 1, wherein the implantable apparatus further comprises:
a plurality of programmable power converters to generate a corresponding plurality of voltage levels.

13. The system of claim 12, wherein the implantable apparatus further comprises:
a second system controller coupled to the plurality of programmable power converters, the system controller configured to generate a third plurality of control signals to select one or more voltage level of the plurality of voltage levels and to provide the selected one or more voltage levels to the stimulation circuit and to the recording circuit.

14. The system of claim 1, wherein the implantable apparatus further comprises:
one or more circuits configured to detect at least one fault or error condition, the at least one fault or error condition selected from the group consisting of: a loss of a clock signal, an insufficient stimulation current level, a data error, a parameter error, a compliance error, and combinations thereof.

15. The system of claim 1, wherein the implantable apparatus further comprises:
an alternating current (AC) to direct current (DC) power converter wirelessly coupleable to receive an AC differential power input and configured to convert the AC differential power input to a direct voltage or direct current.

16. The system of claim 15, wherein the implantable apparatus further comprises:
a clock recovery circuit coupled to receive the AC differential power input and configured to convert the AC differential power input to a clock signal.

17. The system of claim 1, wherein the first system controller is coupleable externally to the human or non-human subject and wherein the transceiver circuit is further configured to wirelessly transmit the corresponding recorded data to the first system controller and to wirelessly receive the plurality of stimulation parameters and the plurality of commands from the first system controller.

18. A system for electrical stimulation and electrical recording in human or non-human subject, the system comprising:
one or more implantable electrode arrays;
a system controller coupleable externally to the human or non-human subject, the system controller configured to wirelessly transmit a plurality of stimulation parameters and a plurality of commands in response to received recorded data; and
one or more implantable apparatuses wirelessly coupleable to the system controller, each implantable apparatus coupleable to a corresponding implantable electrode array comprising a plurality of electrodes, each implantable apparatus comprising:
a stimulation controller configured to generate a first plurality of control signals and a second plurality of control signals to implement at least one type of stimulation selected from the group consisting of: bipolar and biphasic, bipolar and monophasic, unipolar and biphasic, unipolar and monophasic, and combinations thereof;
a plurality of stimulation circuits selectively coupleable to the plurality of electrodes, each stimulation circuit configured, in response to a control signal of a first plurality of control signals, to provide a stimulation current on a selected electrode of the plurality of electrodes, each stimulation circuit comprising: a variable current source configured to generate a selectable, variable current to provide the stimulation current on the selected electrode; a first multiplexer coupled to each variable current source, the first multiplexer comprising a first plurality of switches; and a second multiplexer coupled to the first multiplexer, the second multiplexer comprising a second plurality of switches, each switch of the second multiplexer coupleable to a corresponding electrode of the plurality of electrodes;
a plurality of recording circuits, one or more recording circuits of the plurality of recording circuits configured to generate corresponding recorded data concurrently with the stimulation current;
a transceiver circuit coupled to the plurality of stimulation circuits and to the plurality of recording circuits, the transceiver circuit configured to wirelessly transmit the corresponding recorded data to the first system controller and to wirelessly receive the plurality of stimulation parameters and the plurality of commands from the system controller for closed-loop feedback; and a plurality of blocking circuits, each blocking circuit coupled to a corresponding recording circuit of the plurality of recording circuits and further coupleable to a corresponding electrode of the plurality of electrodes, each blocking circuit configured, in response to a corresponding control signal of the second plurality of control signals, to block the stimulation current on the selected electrode from the corresponding recording circuit.

19. A system for electrical stimulation and electrical recording in human or non-human subject, the system comprising:

one or more implantable electrode arrays;

a system controller coupleable externally to the human or non-human subject, the system controller configured to wirelessly transmit a plurality of stimulation parameters and a plurality of commands in response to received recorded data; and one or more implantable apparatuses wirelessly coupleable to the system controller, each implantable apparatus coupleable to a corresponding implantable electrode array comprising a plurality of electrodes, each implantable apparatus comprising:

a stimulation controller configured to generate a first plurality of control signals and a second plurality of control signals;

a plurality of stimulation circuits selectively coupleable to the plurality of electrodes, each stimulation circuit configured, in response to a control signal of a first plurality of control signals, to provide a stimulation current on a selected electrode of the plurality of electrodes, each stimulation circuit comprising:

a variable current source configured to generate a selectable, variable current to provide the stimulation current on the selected electrode;

a first multiplexer coupled to each variable current source, the first multiplexer comprising a first plurality of switches;

a second multiplexer coupled to the first multiplexer, the second multiplexer comprising a second plurality of switches, each switch of the second multiplexer coupleable to a corresponding electrode of the plurality of electrodes a switchable voltage offset circuit coupleable to the selected electrode; and a switchable grounding circuit coupleable to the selected electrode;

a plurality of recording circuits, one or more recording circuits of the plurality of recording circuits configured to generate corresponding recorded data concurrently with the stimulation current;

a transceiver circuit coupled to the plurality of stimulation circuits and to the plurality of recording circuits, the transceiver circuit configured to wirelessly transmit the corresponding recorded data to the system controller and to wirelessly receive the plurality of stimulation parameters and the plurality of commands from the system controller for closed-loop feedback; and a plurality of blocking circuits, each blocking circuit coupled to a corresponding recording circuit of the plurality of recording circuits and further coupleable to a corresponding electrode of the plurality of electrodes, each blocking circuit configured, in response to a corresponding control signal of the second plurality of control signals, to block the stimulation current on the selected electrode from the corresponding recording circuit.

* * * * *